United States Patent
Wagner et al.

(10) Patent No.: US 9,403,815 B2
(45) Date of Patent: Aug. 2, 2016

(54) COMPOUNDS AND USES THEREOF IN MODULATING LEVELS OF VARIOUS AMYLOID BETA PEPTIDE ALLOFORMS

(75) Inventors: Steven L. Wagner, San Diego, CA (US); Soan Cheng, San Diego, CA (US); William C. Mobley, La Jolla, CA (US); Rudolph E. Tanzi, Charlestown, MA (US)

(73) Assignees: The Regents of the University of California, Oakland, CA (US); The General Hospital Corporation, Boston, MA (US)

( * ) Notice: Subject to any disclaimer, the term of this patent is extended or adjusted under 35 U.S.C. 154(b) by 380 days.

(21) Appl. No.: 13/806,692

(22) PCT Filed: Jun. 24, 2011

(86) PCT No.: PCT/US2011/041905
§ 371 (c)(1),
(2), (4) Date: Mar. 13, 2013

(87) PCT Pub. No.: WO2011/163636
PCT Pub. Date: Dec. 29, 2011

(65) Prior Publication Data
US 2013/0165416 A1   Jun. 27, 2013

Related U.S. Application Data

(60) Provisional application No. 61/358,284, filed on Jun. 24, 2010.

(51) Int. Cl.
*C07D 417/14* (2006.01)
*C07F 9/6558* (2006.01)

(52) U.S. Cl.
CPC .......... *C07D 417/14* (2013.01); *C07F 9/65583* (2013.01)

(58) Field of Classification Search
CPC .................. C07D 417/14; C07F 9/65583
See application file for complete search history.

(56) References Cited

U.S. PATENT DOCUMENTS

| | | | |
|---|---|---|---|
| RE28,819 E | 5/1976 | Thompson | |
| 4,044,126 A | 8/1977 | Cook et al. | |
| 4,328,245 A | 5/1982 | Yu et al. | |
| 4,358,603 A | 11/1982 | Yu | |
| 4,364,923 A | 12/1982 | Cook et al. | |
| 4,409,239 A | 10/1983 | Yu | |
| 4,410,545 A | 10/1983 | Yu et al. | |
| 4,414,209 A | 11/1983 | Cook et al. | |
| 4,522,811 A | 6/1985 | Eppstein et al. | |
| 5,033,252 A | 7/1991 | Carter | |
| 5,052,558 A | 10/1991 | Carter | |
| 5,323,907 A | 6/1994 | Kalvelage | |
| 5,709,874 A | 1/1998 | Hanson et al. | |
| 5,860,957 A | 1/1999 | Jacobsen et al. | |
| 6,267,983 B1 | 7/2001 | Fujii et al. | |
| 6,316,652 B1 | 11/2001 | Steliou | |
| 7,244,739 B2 | 7/2007 | Cheng et al. | |
| 7,781,442 B2 | 8/2010 | Cheng et al. | |
| 7,799,808 B2 | 9/2010 | Cheng et al. | |
| 8,017,629 B2 | 9/2011 | Cheng et al. | |
| 8,119,680 B2 | 2/2012 | Cheng et al. | |
| 2005/0070538 A1 | 3/2005 | Cheng et al. | |
| 2006/0128712 A1 | 6/2006 | Jolidon et al. | |
| 2009/0028787 A1 | 1/2009 | Gravenfors et al. | |
| 2010/0063056 A1 | 3/2010 | Coleman et al. | |
| 2011/0118236 A1 | 5/2011 | Mochizuki et al. | |
| 2013/0023534 A1 | 1/2013 | Casillas et al. | |
| 2013/0143862 A1 | 6/2013 | Ashcraft et al. | |
| 2013/0165416 A1 | 6/2013 | Wagner et al. | |
| 2014/0213570 A1 | 7/2014 | Cheung et al. | |
| 2016/0024073 A1 | 1/2016 | Tanzi et al. | |

FOREIGN PATENT DOCUMENTS

| | | |
|---|---|---|
| EP | 2585455 | 5/2013 |
| EP | 2968296 | 1/2016 |
| JP | 2013530987 | 8/2013 |
| WO | WO 2004/018997 | 3/2004 |
| WO | WO 2004/110350 | 12/2004 |
| WO | WO 2004110350 A2 * | 12/2004 |
| WO | WO 2007/111904 | 10/2007 |
| WO | WO 2008/088881 | 7/2008 |
| WO | WO 2009/050227 | 4/2009 |
| WO | WO 2010/098487 | 9/2010 |
| WO | WO 2010/098488 | 9/2010 |
| WO | WO 2011/059048 | 5/2011 |
| WO | WO 2011/133882 | 10/2011 |
| WO | 2011/163636 | 12/2011 |
| WO | WO 2014/028459 | 2/2014 |
| WO | WO 2014/165263 | 10/2014 |

OTHER PUBLICATIONS

Imbimbo, Journal of Alzheimer's Disease, 2009, IOS Press, vol. 17, pp. 757-760.*
Bonnelli et. al., Expert Opinion in Pharmacotherapy, 2007, Informa UK Ltd, vol. 8, No. 2, pp. 141-153.*
Graziano et. al., Current Neurology and Neuroscience Reports, 2009, Current Medicine Group LLC, vol. 9, pp. 423-429.*
Abramowski, Dorothee et al., "Dynamics of Ab Turnover and Deposition in Different b-Amyloid Precursor Protein Transgenic Mouse Models Following g-Secretase Inhibition," *The Journal of Pharmacology and Experimental Therapeutics*, 2008, 327:411-24 (Exhibit 22).
Imbimbo, Bruno P., "Therapeutic Potential of g-Secretase Inhibitors and Modulators," *Current Topics in Medicinal Chemistry*, 2008, 8:54-61 (Exhibit 23).
Lanz, Thomas A. et al., "Concentration-Dependent Modulation of Amyloid-b in Vivo and in Vitro Using the g-Secretase Inhibitor, LY-450139," *The Journal of Pharmacology and Experimental Therapeutics*, 2006, 319:924-33 (Exhibit 24).

(Continued)

*Primary Examiner* — Sarah Pihonak
(74) *Attorney, Agent, or Firm* — Fish & Richardson P.C.; Vasily Ignatenko

(57) ABSTRACT

The invention provides a novel compound having a structure corresponding to Formula (I):

(A)-(B)-(C)-(D)   (I)

or a pharmaceutically acceptable salt or prodrug thereof and methods for using them.

20 Claims, 4 Drawing Sheets

(56) References Cited

OTHER PUBLICATIONS

Netzer, William J. et al., "Gleevec inhibitors b-amyloid production but not Notch cleavage," PNAS, 2003, 100:12444-9 (Exhibit 25).
Selkoe, Dennis J., "Alzheimer's Disease: Genes, Proteins, and Therapy," Physiological Reviews, 2001, 81:741-66 (Exhibit 26).
Taylor, Edward C. and J. W. Barton, "Synthesis of 2-Aminonicotinamides by Raney Nickel Cleavage of Pyrazolo [3,4-b]-pyridines," J. Am. Chem. Soc., 1959, 81:2448-52 (Exhibit 27).
Japanese Office Action in Japanese Application No. 2013/516839, dated May 20, 2015, with English translation, total of 10 pages.
Fleisher et al., "Phase II safety trial targeting amyloid beta production with a gamma-secretase inhibitor in Alzheimer's disease," Arch. Neurol., Aug. 2008, 65:1031-1038.
Gilman et al., "Clinical effects of a beta immunization (AN1792) in patients with AD in an interrupted trial," Neurology, 2005, 64:1553-1562.
Green et al., "Effect of Tarenflurbil on Cognitive Decline and Activities of Daily Living in Patients With Mild Alzheimer Disease," J. Amer. Med. Asso., 2009, 302:2557-2564.
Hardy and Selkoe, "The Amyloid Hypothesis of Alzheimer's Disease: Progress and Problems on the Road to Therapeutics," Science, Jul. 2002, 297:353-356.
International Preliminary Report on Patentability in International Application No. PCT/US2011/041905, dated Dec. 28, 2012, 5 pages.
International Preliminary Report on Patentability in International Application No. PCT/US2014/025016, dated Sep. 15, 2015, 6 pages.
International Search Report and Written Opinion in International Application No. PCT/US2011/041905, dated Feb. 17, 2012, 8 pages.
International Search Report and Written Opinion in International Application No. PCT/US2014/025016, dated Aug. 27, 2014, 10 pages.
International Search Report and Written Opinion in International Application No. PCT/US2015/058429, dated Jan. 19, 2016, 8 pages.
Kounnas et al., "Modulation of γ-Secretase Reduces β-Amyloid Deposition in a Transgenic Mouse Model of Alzheimer's Disease," Neuron, Sep. 2010, 67:769-780.
Kukar et al., "Substrate-targeting γ-secretase modulators," Nature, Jun. 2008, 453:925-929.
Miles et al., "Bapineuzumab captures the N-terminus of the Alzheimer's disease amyloid-beta peptide in a helical conformation," Sci. Rep., Feb. 2013, 3:1302.
Page et al., "Generation of Aβ38 and Aβ42 Is Independently and Differentially Affected by Familial Alzheimer Disease-associated Presenilin Mutations and γ-Secretase Modulation," J. Bio. Chem., Jan. 2008, 283(2):677-683.
Potter et al., "Increased in vivo amyloid-β42 production, exchange and loss in presenilin mutation carriers," Sci Transl Med., Jun. 2013, 5:189ra77.
Qiu et al., "Epidemiology of Alzheimer's disease: occurrence, determinants, and strategies toward intervention," Dialogues Clin Neurosci., 2009, 11:111-28.
Restriction Requirement issued in U.S. Appl. No. 14/775,483 on Feb. 18, 2016 (8 pages).
Sabbagh and Cummings, "Progressive cholinergic decline in Alzheimer's Disease: consideration for treatment with donepezil 23 mg in patients with moderate to severe symptomology," BMC Neurology, 2011, 11:21.
Salloway et al., "Two phase 3 trials of bapineuzimab in mild-to-moderate Alzheimer's disease," N. Engl. J. Med., Jan. 2014, 370:322-333.
Supplementary European Search Report in European Application No. EP 11799023, dated Oct. 24, 2013, 4 pages.
Tanzi and Bertram, "Twenty years of the Alzheimer's disease amyloid hypothesis: A genetic perspective," Cell, Feb. 2005, 120:545-555.
Uetrecht and Naisbitt, "Idiosyncratic adverse drug reactions: current concepts," Pharmacol. Rev., 2013, 65:779-808.
Wagner et al., "Potential of gamma-secretase modulators in the treatment of Alzheimer's disease," Arch. Neurol., Oct. 2013, 69:1255-1258.
Wagner et al., "Soluble γ-Secretase Modulators Selectively Inhibit Production of the 42-Amino Acid Amyloid β Peptide Variant and Augment the Production of Multiple Carboxy-Truncated Amyloid β Species," Biochemistry, 2014, doi.org/10.1021/bi401537v (PMID 24401146).
Wakabayashi and De Strooper, "Presenilins. Members of the γ-Secretase Quartets, But Part-Time Soloists Too," Physiology, Aug. 2008, 23:194-204.
Anderson et al., "Reductions in beta-amyloid concentrations in vivo by the gamma-secretase inhibitors BMS-289948 and BMS-299897," Biochem. Pharmacol., 2005, 69: 689-698.
Burbach et al., "Vessel ultrastructure in APP23 transgenic mice after passive anti-Aβimmunotherapy and subsequent intracerebral hemorrhage," Neurobiol Aging, 2007, 28: 202-212.
Coric et al., "Safety and Tolerability of the γ-Secretase Inhibitor Avagacestat in a Phase 2 Study of Mild to Moderate Alzheimer Disease," Arch. Neurol., Nov. 2012, 69:1430-1440.
Iwatsubo et al., "Visualization of Aβ 42(43) and Aβ 40 in senile plaques with end-specific Aβ monoclonals: evidence that an initially deposited species is Aβ 42(43)," Neuron., Jul. 1994 13:45-53.
Kopan and Ilagan, "γ-Secretase: proteasome of the membrane?" Nat. Rev. Mol. Cell. Biol., 2004, 5:486-488.
Kumar-Singh et al., "Mean age-of-onset of familial Alzheimer disease caused by presenilin mutations correlates with both increased Aβ42 and decreased Aβ40," Hum. Mutat., Jul. 2006, 27:686-695.
Search Report dated Nov. 5, 2014, 26 pages.
Smith et al., "The effect of plasma protein binding on in vivo efficacy: misconceptions in drug discovery," Nat. Rev. Drug Discov., 2010, 9:929-939.

\* cited by examiner

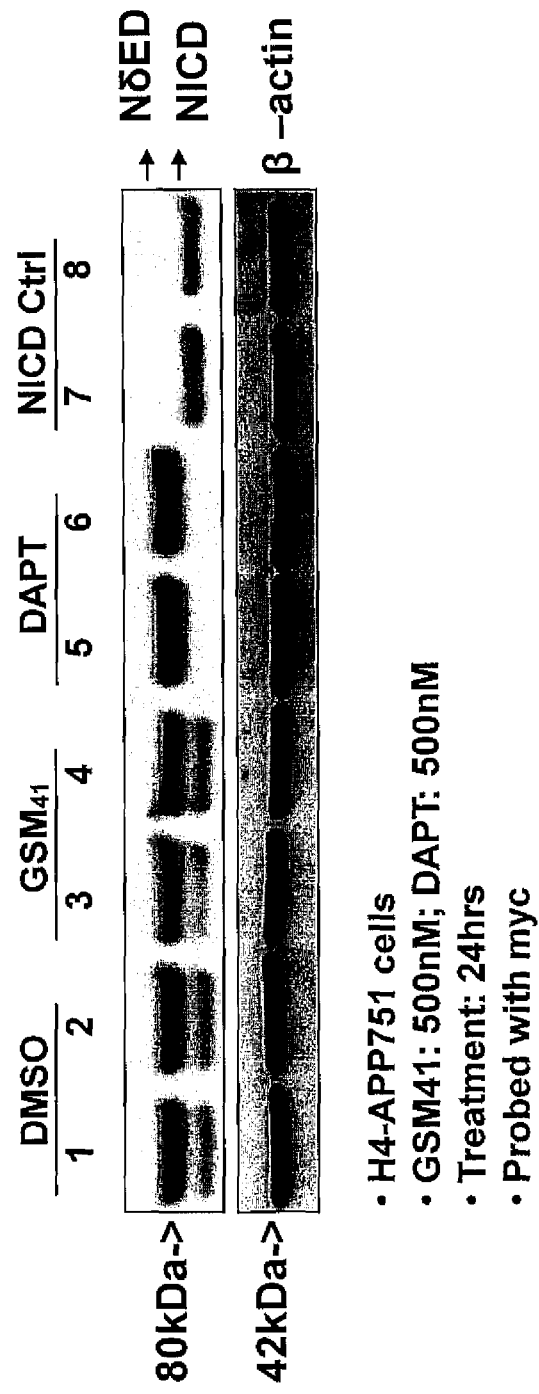
Figure 3 - GSM 41 does not inhibit Notch Proteolysis

COMPOUNDS AND USES THEREOF IN MODULATING LEVELS OF VARIOUS AMYLOID BETA PEPTIDE ALLOFORMS

This application is a 371 application of PCT application No. PCT/US2011/041905, filed Jun. 24, 2011, which claims the priority of U.S. Ser. No. 61/358,284, filed Jun. 24, 2010, the contents of all of which are hereby incorporated by reference in their entirety into the present application.

Throughout this application various publications are referenced. The disclosures of these publications in their entireties are hereby incorporated by reference into this application in order to more fully describe the state of the art to which this invention pertains.

This invention was made with government support under Grant No. CAF-NEU15SW awarded by Cure Alzheimer's Fund. The government has certain rights in the invention.

FIELD OF THE INVENTION

The present invention relates to compounds, prodrugs of such compounds, pharmaceutical compositions containing such compounds and prodrugs of such compounds, and methods of using them. In one aspect, compounds of the invention are useful in modulating the levels certain amyloid-β (Aβ) peptide alloforms such as $A\beta_{42}$. In another aspect, compounds of the invention are useful for treatment of diseases associated with altered levels of certain Aβ peptide alloforms, including various neurodegenerative disorders such as Alzheimer's disease and hemorrhagic stroke associated with cerebrovascular amyloidosis or cerebral amyloid angiopathy (CAA), such as hereditary cerebral hemorrhage with amyloidosis, Dutch type (HCHWA-D).

BACKGROUND OF THE INVENTION

Alzheimer's disease (AD) is a progressive neurodegenerative disorder that is the predominant cause of dementia in people over 65 years of age. AD is characterized neuropathologically by significant neuronal cell loss in certain brain areas, an abundance of structures resembling neurons containing intracellular paired helical filaments (referred to as neurofibrillary tangles), and by the extracellular deposition of a proteinacious material in the brains of AD patients referred to as either neuritic/Aβ plaques or diffuse/Aβ deposits. The major protein component of neuritic/Aβ plaques and diffuse/Aβ deposits is a specific peptide alloform of Aβ known as $A\beta_{42}$. Increased accumulation of $A\beta_{42}$ has been postulated to significantly contribute to the pathogenesis of AD, and is also associated with various other cerebral amyloidoses and neurological disorders such as Down's syndrome (DS), Hereditary Cerebral Hemorrhage with Amyloidosis-Dutch Type (HCHWA-D), cerebral amyloid angiopathy (CAA), and mild cognitive impairment (MCI).

One of the most important lines of evidence implicating the accumulation of the $A\beta_{42}$ peptide in AD comes from the identification of various mutations that result in increased formation of $A\beta_{42}$ and account for certain types of inherited AD (familial AD, or FAD). FAD individuals comprise <10% of all AD cases and generally exhibit symptoms of the disease much earlier than sporadic AD patients.

All Aβ peptides are derived from proteolytic processing of an amyloid precursor protein (APP). mRNA generated from the APP gene on chromosome 21 undergoes alternative splicing to yield several isoforms, three of which (APP695, 751, and 770 amino acid isoforms) predominate in the brain and the cerebrovasculature. The major APP isoforms are single-transmembrane proteins, composed of an extracellular amino-terminal domain (596-687 amino acids) and cytoplasmic tail containing an intracellular trafficking signal (approximately 80-99 amino acids). Within APP, the Aβ peptide sequence is located partially on the extracellular side of the membrane and extends partially into the transmembrane region.

APP is trafficked through the constitutive secretory pathway, where it undergoes post-translational processing, including proteolysis via either of two distinct processing pathways, an amyloidogenic pathway or an alternate pathway. In the amyloidogenic pathway, APP is cleaved by either β-secretase-1 (BACE-1) or Cathepsin D at the beginning of the Aβ domain that defines the amino terminus of all full length Aβ peptides. These Aβ peptides vary in length from approximately 34-42 amino acids. Cleavage of APP by either BACE-1 or Cathepsin D generates a soluble amino-terminal fragment, sAPPβ, as well as an amyloidogenic carboxyl-terminal fragment approximately 99 amino acids long referred to as (C99). Additional proteolysis of C99 by γ-secretase, a presenilin-dependent proteolytic complex, produces an intracellular domain referred to as AICD and number of different Aβ peptides of various lengths (e.g., $A\beta_{34}$, $A\beta_{37}$, $A\beta_{38}$, $A\beta_{39}$, $A\beta_{40}$ and $A\beta_{42}$). In another processing pathway, APP is cleaved by α-secretase within the Aβ domain, yielding a soluble amino-terminal fragment, sAPPα, and a carboxyl-terminal fragment approximately 83 amino acids long referred to as C83. This α-secretase-mediated proteolysis of APP precludes the formation of the intact full length Aβ peptides (e.g., $A\beta_{34}$, $A\beta_{37}$, $A\beta_{38}$, $A\beta_{39}$, $A\beta_{40}$ and $A\beta_{42}$) which specifically require the combination of either BACE-1 or Cathepsin D and γ-secretase activities on APP and C99, respectfully.

The predominant Aβ peptide alloform found in neuritic/Aβ plaques and diffuse/Aβ deposits from AD brains is the $A\beta_{42}$ peptide. $A\beta_{42}$ is the species initially deposited in AD brains and is highly prone to aggregate in vitro. Therefore, enzymes responsible for generating the $A\beta_{42}$ species in particular, may be a viable target in the development of therapeutics for the treatment of disease or disorders characterized by excessive $A\beta_{42}$ generation and/or accumulation (Selkoe, D J Alzheimer's disease: genes, proteins and therapy [review] *Physiol. Rev.* 2001; 81:741-766).

Currently, there is no cure or effective treatment for preventing or retarding the progression of AD pathogenesis, and the few FDA-approved drugs, including Aricept, Exelon, Cognex, Reminyl and Memantine, are palliative treatments at best. Based on the well established correlation between cerebral $A\beta_{42}$ accumulation and neuronal cell loss in AD; attenuating $A\beta_{42}$ levels relative to the levels of shorter Aβ peptide species, and thereby preferentially reducing the levels of the putatively pathogenic $A\beta_{42}$ species, represents a rational approach for decreasing extracellular $A\beta_{42}$ deposition (thereby attenuating formation of diffuse Aβ deposits as well as neuritic/Aβ plaques) and minimizing neuronal cell death in AD.

There exists a medical need for compounds that modulate levels of Aβ peptides, including $A\beta_{42}$. Such compounds should be useful for the treatment of a variety of degenerative disorders, including neurodegenerative diseases such as AD (Imbimbo, B P Therapeutic potential of gamma-secretase inhibitors and modulators *Curr Top Med Chem* 2008; 8:54-61).

Compounds of the invention are especially advantageous because they are expected to display an improved facility to achieve beneficial levels in the brain of a subject administered the compound compared to previously described compounds of this general class (U.S. Pat. No. 7,244,739—Compounds and uses thereof in modulating amyloid beta 2007 US Patent Office). The novel compounds described herein, especially those containing the cleavable phosphonomethoxy moiety, should be much more amenable to preclinical and clinical development protocols as a result of their significant solubilities in aqueous solvents.

SUMMARY OF THE INVENTION

In accordance with the present invention, novel compounds have been discovered that are useful for a variety of therapeutic applications.

In one aspect of the present invention, there are provided compounds which have activity in modulating the relative levels of specific Aβ peptide alloforms. As a result, such compounds are applicable for treating diseases associated with aberrant levels of $A\beta_{42}$ and/or any condition in which modulation of the relative levels specific Aβ peptide alloforms provides a therapeutic effect. In one aspect of the invention, compounds herein are useful in the treatment of neurodegenerative disorders, such as AD.

In one aspect, the invention also provides a compound having a structure corresponding to Formula (I):

(A)-(B)-(C)-(D)     (I)

or a pharmaceutically acceptable salt or prodrug thereof:
Wherein A is:

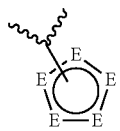

Wherein each E is independently N, NR, C, or $CR^1$, provided that two or three E's are N or NR; N is nitrogen; C is carbon; R is hydrogen, substituted or unsubstituted alkyl, substituted or unsubstituted alkenyl, substituted or unsubstituted alkynyl, substituted or unsubstituted alkoxy, substituted or unsubstituted alkylamino, substituted or unsubstituted cycloalkyl, or substituted or unsubstituted aryl;

Each $R^1$ is independently hydrogen, substituted or unsubstituted alkyl, substituted or unsubstituted alkenyl, substituted or unsubstituted alkynyl, substituted or unsubstituted alkoxy, substituted or unsubstituted alkylamino, substituted or unsubstituted cycloalkyl, or substituted or unsubstituted aryl;

Wherein B is:

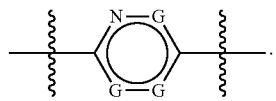

Wherein each G is independently $CR^2$;
Each $R^2$ is independently a hydrogen, halogen, substituted or unsubstituted alkyl, substituted or unsubstituted alkenyl, substituted or unsubstituted alkynyl, substituted or unsubstituted alkoxy, substituted or unsubstituted alkylamido, substituted or unsubstituted alkylamino, substituted or unsubstituted amino, substituted or unsubstituted alkylsulfide, substituted or unsubstituted alkyl sulfinyl group, or substituted or unsubstituted alkyl sulfonyl group;

Wherein B is:

Wherein each G is independently $CR^{3a}$;
Each $R^{3a}$ is independently a hydrogen, halogen, substituted or unsubstituted alkyl, substituted or unsubstituted alkenyl, substituted or unsubstituted alkynyl, substituted or unsubstituted alkoxy, substituted or unsubstituted alkylamido, substituted or unsubstituted alkylamino, substituted or unsubstituted amino, substituted or unsubstituted alkylsulfide, substituted or unsubstituted alkyl sulfinyl group, or substituted or unsubstituted alkyl sulfonyl group;

Wherein each G is independently $CR^{3b}$;
Each $R^{3b}$ is independently a hydrogen, halogen, substituted or unsubstituted alkyl, substituted or unsubstituted alkenyl, substituted or unsubstituted alkynyl, substituted or unsubstituted alkoxy, substituted or unsubstituted alkylamido, substituted or unsubstituted alkylamino, substituted or unsubstituted amino, substituted or unsubstituted alkylsulfide, substituted or unsubstituted alkyl sulfinyl group, or substituted or unsubstituted alkyl sulfonyl group; or

Wherein each G is independently $CR^{3c}$;
Each $R^{3c}$ is independently a hydrogen, halogen, substituted or unsubstituted alkyl, substituted or unsubstituted alkenyl, substituted or unsubstituted alkynyl, substituted or unsubstituted alkoxy, substituted or unsubstituted alkylamido, substituted or unsubstituted alkylamino, substituted or unsubstituted amino, substituted or unsubstituted alkylsulfide, substituted or unsubstituted alkyl sulfinyl group, or substituted or unsubstituted alkyl sulfonyl group; and Wherein C is:

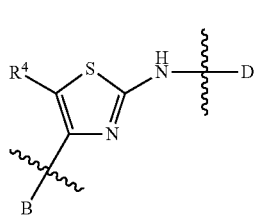

Wherein $R^4$ is hydrogen, halogen, substituted or unsubstituted alkyl, substituted or unsubstituted cycloalkyl, substituted or unsubstituted aryl, or substituted or unsubstituted alkoxy; and Wherein D is:

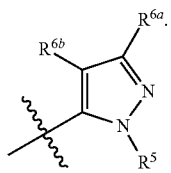

a

Wherein R⁵ is a hydrogen, substituted or unsubstituted alkyl, or substituted or unsubstituted cycloalkyl;
R$^{6a}$ and R$^{6b}$ are independently a hydrogen, substituted or unsubstituted alkyl, or substituted or unsubstituted cycloalkyl;

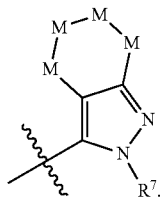

b

Wherein R⁷ is a hydrogen, substituted or unsubstituted alkyl, or substituted or unsubstituted cycloalkyl;
M is independently CHR⁸;
Each R⁸ is independently a hydrogen, halogen, substituted or unsubstituted alkyl, substituted or unsubstituted alkenyl, substituted or unsubstituted alkynyl, or substituted or unsubstituted alkoxy; or

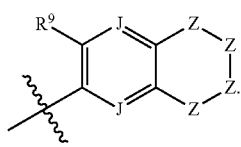

c

Where R⁹ is a hydrogen, halogen, or a substituted or unsubstituted alkyl;
J is independently CH or N;
Z is independently CHR¹⁰;
Each R¹⁰ is independently a hydrogen, halogen, substituted or unsubstituted alkyl, substituted or unsubstituted alkenyl, substituted or unsubstituted alkynyl, or substituted or unsubstituted alkoxy.

The invention also provides a method of modulating levels of a highly fibrillogenic amyloid-beta (Aβ) peptide comprising contacting a protease which proteolyzes an amyloid precursor protein (AAP) carboxyl-terminal fragment (CTF) or fragment thereof with an effective amount of a compound of the invention so as to modulate the levels of fibrillogenic amyloid-beta (Aβ) peptides.

The invention also provides a method of promoting production of Aβ$_{38}$ or Aβ$_{37}$ comprising contacting a protease which proteolyzes an amyloid precursor protein (APP) carboxyl-terminal fragment (CTF) or fragment thereof with an effective amount of a compound of the invention so as to promote production of Aβ$_{38}$ or Aβ$_{37}$.

BRIEF DESCRIPTION OF THE FIGURES

FIG. 3 is a Western Blot analysis showing that GSM41 does not inhibit NOTCH proteolysis. Stable H4 human neuroglioma cells over-expressing human APP751 (H4-APP751 cells), were transfected with the NδED construct (Lanes 1-6), and then treated with vehicle (DMSO; Lanes 1-2 Control), 500 nM GSM41 (test compound), or 500 nM DAPT (Lanes 5-6 inhibitor of gamma secretase) for another 24 hrs. Additionally H4-APP751 cells were transfected with the NICD construct (as a reference of NICD; Lanes 7-8). Cells were harvested 48 hrs post transfection and subjected to Western blotting analysis. Myc antibody was utilized to assess the NδED and NICD tagged with Myc on their N-termini. β-Actin was utilized as the loading control. DAPT decreased NICD levels; however, the GSM41 did not change NICD levels, compared to control (Lanes 1-2). Results indicate NICD production is not inhibited by the GSM compound 41.

DETAILED DESCRIPTION OF THE INVENTION

Figure 1:
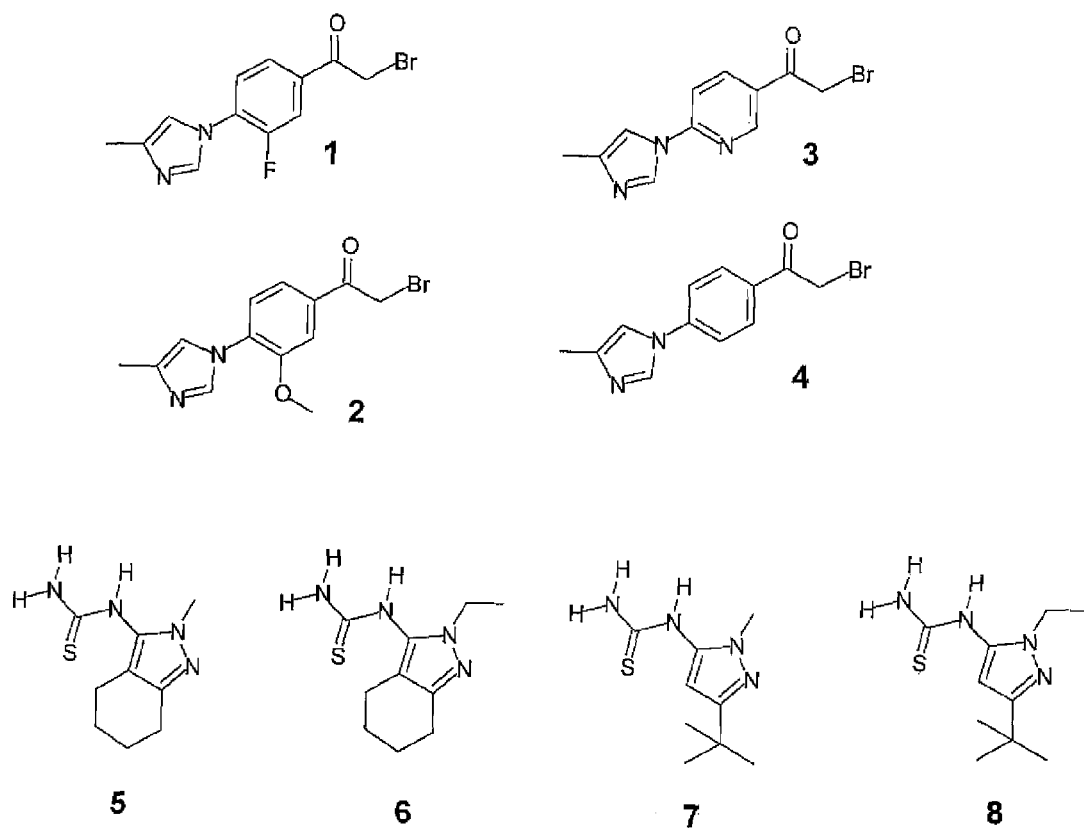
FIG. 1 shows the chemical structures of advance intermediates.
Figure 2:
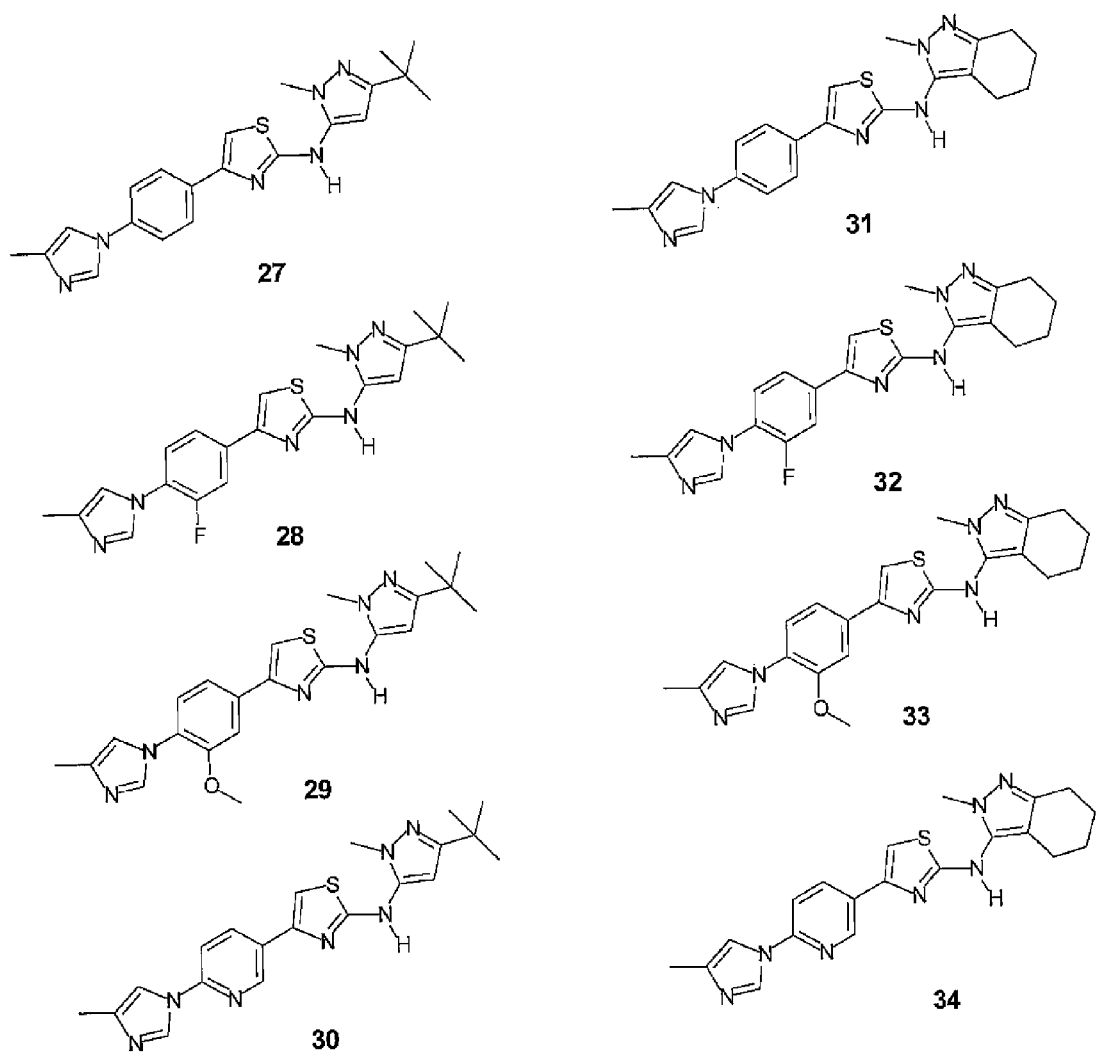
FIG. 2 shows the chemical structures of novel GSM compounds.
Figure 2:
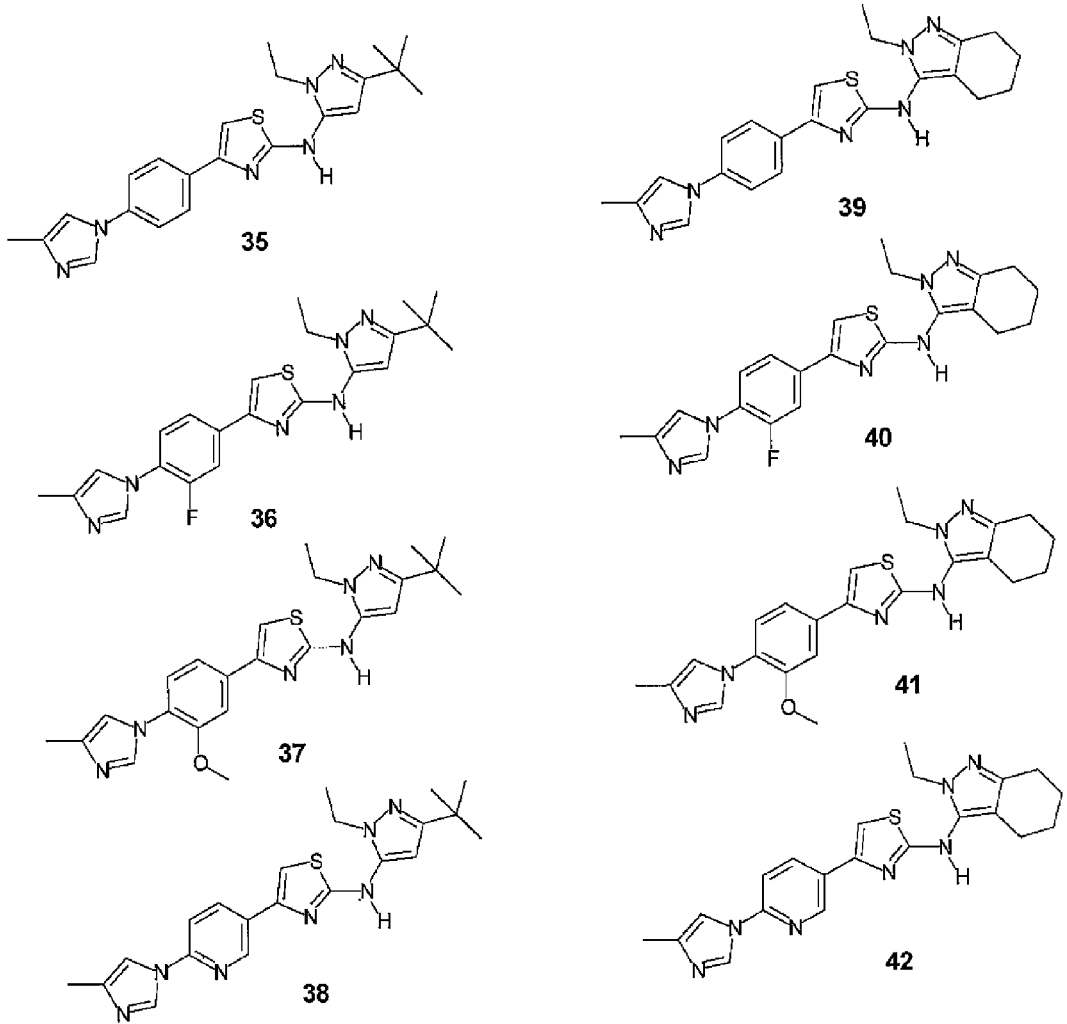

Unless defined otherwise, all technical and scientific terms used herein have the same meaning as is commonly understood by one of ordinary skill in the art to which this invention belongs. All patents, applications, published applications and other publications referred to herein are incorporated by reference in their entirety.

I. Compounds of the Invention

The present invention provides novel compounds having a structure corresponding to Formula (I): (A)-(B)-(C)-(D) (Formula I) including pharmaceutically acceptable salts, and prodrugs thereof.

In one embodiment of Formula I, A may be:

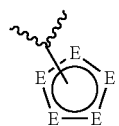

In this embodiment, each E may be independently N, NR, C, or CR¹, provided that two or three E's are N or NR; N is nitrogen; C is carbon; R is a hydrogen, substituted or unsubstituted alkyl, substituted or unsubstituted alkenyl, substituted or unsubstituted alkynyl, substituted or unsubstituted alkoxy, substituted or unsubstituted alkylamino, substituted or unsubstituted cycloalkyl, or substituted or unsubstituted aryl; each R¹ is independently hydrogen, substituted or unsubstituted alkyl, substituted or unsubstituted alkenyl, substituted or unsubstituted alkynyl, substituted or unsubstituted alkoxy, substituted or unsubstituted alkylamino, substituted or unsubstituted cycloalkyl, or substituted or unsubstituted aryl.

Throughout, the jagged line

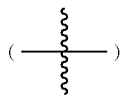

above denotes attachment to the other member(s) of (A)-(B)-(C)-(D) of Formula I.

Further, in Formula I, in one embodiment, B may be:

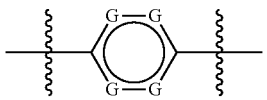

In accordance with the practice of the invention, each G may be independently $CR^2$; C is carbon; and each $R^2$ may be independently a hydrogen, halogen, substituted or unsubstituted alkyl, substituted or unsubstituted alkenyl, substituted or unsubstituted alkynyl, substituted or unsubstituted alkoxy, substituted or unsubstituted alkylamido, substituted or unsubstituted alkylamino, substituted or unsubstituted amino, substituted or unsubstituted alkylsulfide, substituted or unsubstituted alkyl sulfinyl group, or substituted or unsubstituted alkyl sulfonyl group.

In another embodiment, B of Formula I may be:

In this embodiment, N is nitrogen; each G may be independently $CR^{3a}$; C is carbon; and each $R^{3a}$ may be independently a hydrogen, halogen, substituted or unsubstituted alkyl, substituted or unsubstituted alkenyl, substituted or unsubstituted alkynyl, substituted or unsubstituted alkoxy, substituted or unsubstituted alkylamido, substituted or unsubstituted alkylamino, substituted or unsubstituted amino, substituted or unsubstituted alkylsulfide, substituted or unsubstituted alkyl sulfinyl group, or substituted or unsubstituted alkyl sulfonyl group;

In yet another embodiment, B of Formula I may be:

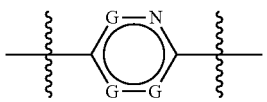

In this embodiment, N is nitrogen; each G may be independently $CR^{3b}$; C is carbon; and each $R^{3b}$ may be independently a hydrogen, halogen, substituted or unsubstituted alkyl, substituted or unsubstituted alkenyl, substituted or unsubstituted alkynyl, substituted or unsubstituted alkoxy, substituted or unsubstituted alkylamido, substituted or unsubstituted alkylamino, substituted or unsubstituted amino, substituted or unsubstituted alkylsulfide, substituted or unsubstituted alkyl sulfinyl group, or substituted or unsubstituted alkyl sulfonyl group.

In yet a further embodiment, B of Formula I may be:

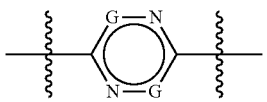

In this embodiment, N is nitrogen; each G may be independently $CR^{3c}$; C is carbon; and each $R^{3c}$ may be independently a hydrogen, halogen, substituted or unsubstituted alkyl, substituted or unsubstituted alkenyl, substituted or unsubstituted alkynyl, substituted or unsubstituted alkoxy, substituted or unsubstituted alkylamido, substituted or unsubstituted alkylamino, substituted or unsubstituted amino, substituted or unsubstituted alkylsulfide, substituted or unsubstituted alkyl sulfinyl group, or substituted or unsubstituted alkyl sulfonyl group.

Further, in Formula I, in one embodiment, C may be:

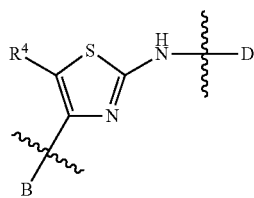

In this embodiment, N is nitrogen; S is sulfur; $R^4$ may be a hydrogen, halogen, substituted or unsubstituted alkyl, substituted or unsubstituted cycloalkyl, substituted or unsubstituted aryl, or substituted or unsubstituted alkoxy. B is member B and D is member D of (A)-(B)-(C)-(D) of Formula I.

Additionally, in Formula I, in one embodiment, D may be:

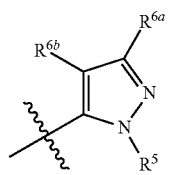

In this embodiment, N is nitrogen; $R^5$ may be a hydrogen, substituted or unsubstituted alkyl, or substituted or unsubstituted cycloalkyl; and $R^{6a}$ and $R^{6b}$ may be independently a hydrogen, substituted or unsubstituted alkyl, or substituted or unsubstituted cycloalkyl.

In another embodiment, D of Formula I may be:

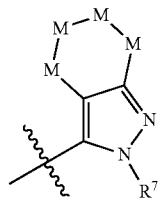

In this embodiment, N is nitrogen; $R^7$ may be a hydrogen, substituted or unsubstituted alkyl, or substituted or unsubstituted cycloalkyl; M may be independently $CHR^8$; C is carbon; and each $R^8$ is independently a hydrogen, halogen, substituted or unsubstituted alkyl, substituted or unsubstituted alkenyl, substituted or unsubstituted alkynyl, or substituted or unsubstituted alkoxy.

In a further embodiment, D of Formula I may be:

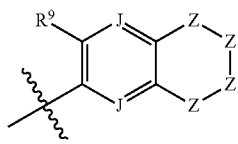

In this embodiment, $R^9$ may be a hydrogen (H), halogen, or a substituted or unsubstituted alkyl; J may be independently CH or N; Z may be independently $CHR^{10}$; C is carbon; H is hydrogen; and each $R^{10}$ may be independently a hydrogen, halogen, substituted or unsubstituted alkyl, substituted or unsubstituted alkenyl, substituted or unsubstituted alkynyl, or substituted or unsubstituted alkoxy.

As used herein, reference to a certain element is meant to include all isotopes of that element. For instance, if a group is defined to include hydrogen or H, it also can include deuterium, and/or tritium.

Compounds of the present invention may have asymmetric centers and may occur, except when specifically noted, as mixtures of stereoisomers or as individual diastereomers, or enantiomers, with all isomeric forms being included in the present invention. Compounds of the present invention embrace all conformational isomers. Compounds of the present invention may also exist in one or more tautomeric forms, including both single tautomer and mixtures of tautomers.

The phrase "hydrocarbyl" refers to any organic radical having a directly attachable carbon atom to any molecule presented herein. The phrase "substituted hydrocarbyl" refers to a hydrocarbyl group that is substituted according to the definition provided below. Hydrocarbyl groups include saturated and unsaturated hydrocarbyls, straight and branched chain aliphatic hydrocarbyls, cyclic hydrocarbyls, and aromatic hydrocarbyls.

The phrase "substituted" refers to an atom or group of atoms that has been replaced with another substituent. The phrase "substituted" includes any level of substitution, e.g. mono-, di-, tri-, tetra-, or penta-substitution, where such substitution is chemically permissible. Substitutions can occur at any chemically accessible position and on any atom, such as substitution(s) on carbons or any heteroatom. For example, substituted compounds are those where one or more bonds to a hydrogen or carbon atom(s) contained therein are replaced by a bond to non-hydrogen and/or non-carbon atom(s).

The phrase "alkyl" refers to hydrocarbyl chains comprising from 1 to 20 carbon atoms. The phrase "alkyl" includes straight chain alkyl groups, such as methyl, ethyl, propyl, butyl, pentyl, hexyl, heptyl, octyl, nonyl, decyl, undecyl, dodecyl, and the like. The phrase also includes branched chain isomers of straight chain alkyl groups, including but not limited to, the following which are provided by way of example: —CH(CH₃)₂, —CH(CH₃)(CH₂CH₃), —CH(CH₂CH₃)₂, —C(CH₃)₃, —C(CH₂CH₃)₃, —CH₂CH(CH₃)₂, —CH₂CH(CH₃)(CH₂CH₃), —CH₂CH(CH₂CH₃)₂, —CH₂C(CH₃)₃, —CH₂C(CH₂CH₃)₃, —CH(CH₃)CH(CH₃)(CH₂CH₃), —CH₂CH₂CH(CH₃)₂, —CH₂CH₂CH(CH₃)(CH₂CH₃), —CH₂CH₂CH(CH₂CH₃)₂, —CH₂CH₂C(CH₃)₃, —CH₂CH₂C(CH₂CH₃)₃, —CH(CH₃)CH₂CH(CH₃)₂, —CH(CH₃)CH(CH₃)CH(CH₃)₂, and —CH(CH₂CH₃)CH(CH₃)CH(CH₃)(CH₂CH₃). Thus, alkyl groups may include primary alkyl groups, secondary alkyl groups, and tertiary alkyl groups. Preferred alkyl groups include alkyl groups having from 1 to 16 carbon atoms, or from 1 to 3 carbon atoms, such as methyl, ethyl, propyl, and isopropyl.

In accordance with the practice of the invention, the unsubstituted alkyl group may include but is not limited to a methyl, ethyl, propyl, isopropyl, butyl, sec-butyl, or tert-butyl group. Further, one embodiment, the unsubstituted alkoxy group may be a methoxy group. Additionally, in one embodiment, the unsubstituted cycloalkyl group may be a cyclopropyl group. Also, in one embodiment, the unsubstituted alkyl sulfinyl group may be a methyl sulfinyl group. Further, in one embodiment, the unsubstituted alkylsulfide may be a methylsulfide group.

The phrase "substituted alkyl" refers to an alkyl group that may be substituted according to the definition provided above. Examples of "substituted alkyl" groups include, but are not limited to, replacements of carbon or hydrogen atom(s) with a halogen atom(s), such as trifluoromethyl; an oxygen atom(s) in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, N-alkyloxides, imides, and enamines; a silicon atom in groups such as in trialkylsilyl groups, dialkylarylsilyl groups, alkyldiarylsilyl groups, and triarylsilyl groups; and other various heteroatoms. Additionally, substituted alkyl groups may be bonded to one or more carbon atom(s).

The phrase "alkenyl" refers to hydrocarbyl chains comprising from 2 to 20 carbon atoms and comprising at least one carbon-carbon double bond (—C=C—). The phrase "alkenyl" includes straight chain alkenyl groups, as well as branched chain isomers of straight chain alkenyl groups. Preferably, alkenyl groups comprise from 1 to 8 double bond(s). The phrase "substituted alkenyl" refers to an alkenyl group that is substituted according to the definition provided above.

The phrase "alkynyl" refers to hydrocarbyl chains comprising from 2 to 20 carbon atoms and comprising at least one carbon-carbon triple bond (—C≡C—). The phrase "alkynyl" includes straight chain alkynyl groups, as well as branched chain isomers of straight chain alkynyl groups. Preferably, alkynyl groups comprise from 1 to 8 triple bond(s). The phrase "substituted alkynyl" refers to an alkynyl group that is substituted according to the definition provided above.

The phrase "cycloalkyl" refers to an alicyclic moiety having 3 to 20 carbon atoms and comprising any chemically permissible amount of saturated or unsaturated bonds. Preferably, cycloalkyl groups comprise from 3 to 7 carbons atoms. Cycloalkyl groups include, but are not limited to, cyclopropyl, cyclobutyl, cyclopentyl, cyclohexyl, cycloheptyl, cyclooctyl, and the like. The phrase "substituted cycloalkyl" refers to a cycloalkyl group that is substituted according to the definition provided above. Substituted cycloalkyl groups can have one or more atom substituted with straight or branched chain alkyl groups and can further comprise cycloalkyl groups that are substituted with other rings including fused rings. Examples of cycloalkyl groups that are substituted with fused rings include, but are not limited to, adamantyl, norbornyl, bicyclo[2.2.2]octyl, decalinyl, tetrahydronaphthyl, and indanyl, bornyl, camphenyl, isocamphenyl, and carenyl groups. Representative substituted cycloalkyl groups may be mono-substituted or substituted more than once, such as, but not limited to, 2,2-, 2,3-, 2,4-, 2,5-, or 2,6-disubstituted cyclohexyl groups or mono-, di- or tri-substituted norbornyl or cycloheptyl groups, which may be substituted with, for example, alkyl, alkoxy, amino, thio, or halo groups.

The phrase "cycloalkylene" refers to divalent cycloalkyl groups comprising from 3 to 20 carbon atoms, and "substituted cycloalkylene" refers to cycloalkylene groups further bearing one or more substituents as set forth above.

The phrase "heterocyclyl", "heterocyclic", or "heterocycle" refers to nonaromatic cyclic hydrocarbyl compounds of which at least one ring member is a heteroatom. Heterocyclic groups include monocyclic, bicyclic, and polycyclic ring compounds containing from 3 to 20 ring members of which one or more is a heteroatom such as, but not limited to, N, O, and S. Heterocyclic groups include, any level of saturation. For instance, heterocyclic groups include unsaturated 3 to 8 membered rings containing 1 to 4 nitrogen atoms; saturated 3 to 8 membered rings containing 1 to 4 nitrogen atoms; condensed unsaturated heterocyclic groups containing 1 to 4 nitrogen atoms; unsaturated 3 to 8 membered rings containing 1 to 2 oxygen atoms and 1 to 3 nitrogen atoms; saturated 3 to 8 membered rings containing 1 to 2 oxygen atoms and 1 to 3 nitrogen atoms; unsaturated condensed heterocyclic groups containing 1 to 2 oxygen atoms and 1 to 3 nitrogen atoms; unsaturated 3 to 8 membered rings containing 1 to 3 sulfur atoms and 1 to 3 nitrogen atoms. Preferred heterocyclyl groups contain 5 or 6 ring members. Examples of heterocyclic groups include, but are not limited to, morpholine and piperazine. The phrase "substituted heterocyclyl" or "substituted heterocyclic" refers to a heterocyclyl group that is substituted according to the definition provided above.

The phrase "heterocyclene" or "heterocyclylene" refers to divalent heterocyclic (i.e., ring-containing) groups comprising from 3 to 20 carbon atoms and "substituted heterocycloalkylene" refers to heterocycloalkylene groups further bearing one or more substituents as set forth above.

The phrase "aryl" refers to single-ring aromatic radicals which may include from 5 to 20 carbon atoms. Aryl groups include, but are not limited to, phenyl, biphenyl, anthracenyl, and naphthenyl. The phrase "substituted aryl group" refers to an aryl group that is substituted according to the definition provided above. For example, substituted aryl groups may be bonded to one or more carbon atom(s), oxygen atom(s), nitrogen atom(s), and/or sulfur atom(s) and also includes aryl groups in which one or more aromatic carbons of the aryl group is bonded to a substituted and/or unsubstituted alkyl, alkenyl, or alkynyl group. This includes bonding arrangements in which two carbon atoms of an aryl group are bonded to two atoms of an alkyl, alkenyl, or alkynyl group to define a fused ring system (e.g. dihydronaphthyl or tetrahydronaphthyl). Thus, the phrase "substituted aryl" includes, but is not limited to tolyl, hydroxyphenyl, and the like.

The phrase "arylene" refers to divalent aryl groups comprising from 3 to 20 carbon atoms and "substituted arylene" refers to arylene groups further bearing one or more substituents as set forth above.

The phrase "heteroaryl" refers to a 3 to 20-membered aromatic ring consisting of carbon atoms and heteroatoms, such as N, S, and O or (ii) an 8- to 10-membered bicyclic or polycyclic ring system containing carbon atoms and heteroatoms, such as N, S, and O, wherein at least one of the rings in the bicyclic system is an aromatic ring. The heteroaryl ring may be attached at any heteroatom or carbon atom. Representative heteroaryl compounds include, for example, imidazolyl, pyridyl, pyrazinyl, pyrimidinyl, thiophenyl, thiazolyl, furanyl, pyridofuranyl, pyrimidofuranyl, pyridothienyl, pyridazothienyl, pyridooxazolyl, pyridazooxazolyl, pyrimidooxazolyl, pyridothiazolyl, pyridazothiazolyl, pyrrolyl, pyrrolinyl, imidazolyl, pyrazolyl, pyridyl, dihydropyridyl, pyrimidyl, pyrazinyl, pyridazinyl, triazolyl (e.g. 4H-1,2,4-triazolyl, 1H-1,2,3-triazolyl, and 2H-1,2,3-triazolyl), tetrazolyl, (e.g. 1H-tetrazolyl and 2H tetrazolyl), pyrrolidinyl, imidazolidinyl, piperidinyl, piperazinyl, indolyl, isoindolyl, indolinyl, indolizinyl, benzimidazolyl, quinolyl, isoquinolyl, indazolyl, benzotriazolyl, oxazolyl, isoxazolyl, oxadiazolyl (e.g. 1,2,4-oxadiazolyl, 1,3,4-oxadiazolyl, and 1,2,5-oxadiazoly benzoxazolyl, benzoxadiazolyl, benzoxazinyl, (e.g. 2H-1,4-benzoxazinyl), thiazolyl, isothiazolyl, thiadiazolyl (e.g. 1,2,3-thiadiazolyl, 1,2,4-thiadiazolyl, 1,3,4-thiadiazolyl, and 1,2,5-thiadiazolyl). The phrase "substituted heteroaryl" refers to a heteroaryl group that is substituted according to the definition provided above.

The phrase "heteroarylene" refers to divalent aryl groups containing one or more heteroatoms (e.g., N, O, S or the like) as part of the aromatic ring, and typically having in the range of 3 up to 20 carbon atoms and "substituted heteroarylene" refers to heteroarylene groups further bearing one or more substituents as set forth above.

The phrase "alkoxy" refers to an oxygen-containing alkyl or cycloalkyl group, as defined above.

The phrase "alkylamido" refers to an alkyl group, as defined as above, which comprises —C(O)NR$_2$ wherein each R is independently hydrogen, alkyl, cycloalkyl, aryl, heteroaryl, or the like. Furthermore, alkylamido embraces embodiments wherein R, together with N, forms a cyclic structure.

The phrase "amino" refers to —NR$_2$ wherein each R is independently hydrogen, alkyl, cycloalkyl, aryl, heteroaryl, and the like. Furthermore, amino embraces embodiments wherein R, together with N, forms a cyclic structure.

The phrase "alkylamino" refers to an alkyl group, as defined as above, which comprises an amino group, as defined above.

The phrase "halogen" refers to F, Cl, Br, or I.

Embodiments presented herein include compounds of Formula (I) wherein A, together with B, or B, together with C, forms a fused ring system. The phrase "fused ring system" refers to two or three rings that are fused together e.g. bicyclic or tricyclic ring systems. Representative fused ring systems include, for example, naphthyl, 1-carbolinyl, and the like; and substituted ring systems, such as biphenyl, phenylpyridyl, diphenylpiperazinyl, and the like.

In one embodiment, in Formula (I), A may be

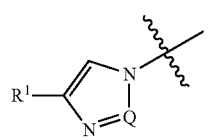

wherein Q may be either CH or N.

Further, $R^1$ may be a halogen or substituted or unsubstituted $C_1$-$C_5$ alkyl.

Examples of a prodrug of a compound of the invention include but is not limited to compounds having the structure Formula X and XI:

(X)

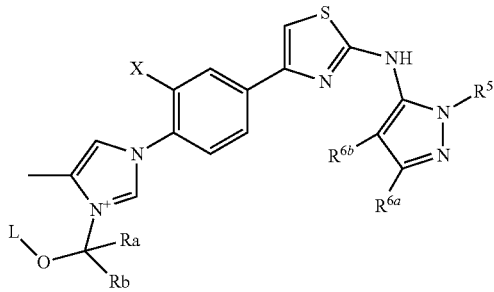

(XI)

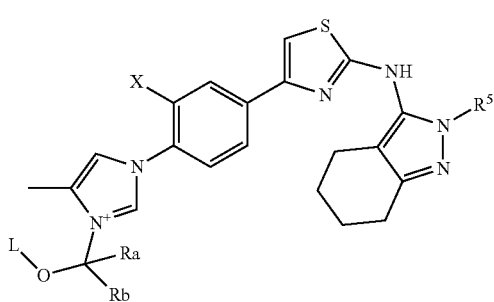

In embodiments of Formula X or XI, X may be a hydrogen, halogen, substituted or unsubstituted alkoxy, substituted or unsubstituted alkylsulfide, substituted or unsubstituted alkyl sulfinyl group, or substituted or unsubstituted alkyl sulfonyl group; $R^5$ is a hydrogen, substituted or unsubstituted alkyl, or substituted or unsubstituted cycloalkyl; $R^{6a}$ and $R^{6b}$ is independently a hydrogen, substituted or unsubstituted alkyl, or substituted or unsubstituted cycloalkyl; Ra and Rb are a $C_1$-$C_6$ alkyl group; and L may be a phosphono group.

Pharmaceutically acceptable salts of the invention include but is not limited to a monohydrochloride salt.

In an embodiment of the invention, the compound does not inhibit the gamma-secretase-mediated proteolysis of NOTCH and the NOTCH signaling pathway.

In an embodiment of the invention, a compound having the structure of Formula I may have the structure corresponding to Formula (II):

(II)

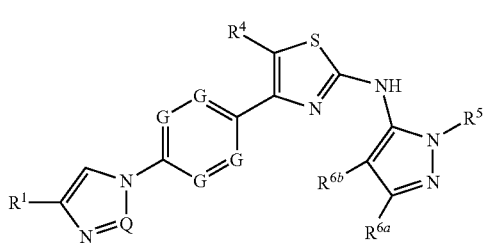

In this embodiment, $R^1$ may be a halogen or substituted or unsubstituted $C_1$-$C_5$ alkyl. $R^4$ may be a hydrogen, halogen, substituted or unsubstituted alkyl, substituted or unsubstituted cycloalkyl, substituted or unsubstituted aryl, or substituted or unsubstituted alkoxy. $R^5$ may be a hydrogen, substituted or unsubstituted alkyl, or substituted or unsubstituted cycloalkyl. $R^{6a}$ and $R^{6b}$ may be independently a hydrogen, substituted or unsubstituted alkyl, or substituted or unsubstituted cycloalkyl.

In another embodiment, the compound of the invention may have the structure corresponding to Formula (III):

(III)

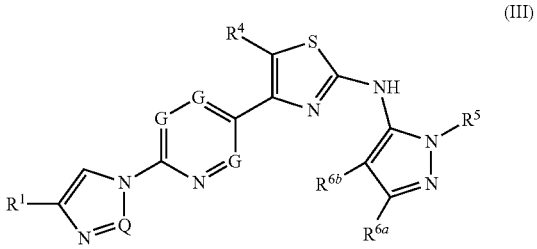

In this embodiment, $R^1$ may be a halogen or substituted or unsubstituted $C_1$-$C_5$ alkyl. $R^4$ may be a hydrogen, halogen, substituted or unsubstituted alkyl, substituted or unsubstituted cycloalkyl, substituted or unsubstituted aryl, or substituted or unsubstituted alkoxy. $R^5$ may be a hydrogen, a substituted or unsubstituted alkyl, or substituted or unsubstituted cycloalkyl. Further, $R^{6a}$ and $R^{6b}$ may be independently a hydrogen, substituted or unsubstituted alkyl, or substituted or unsubstituted cycloalkyl.

In another embodiment of the invention the compound of the invention may have a structure corresponding to Formula (IV):

(IV)

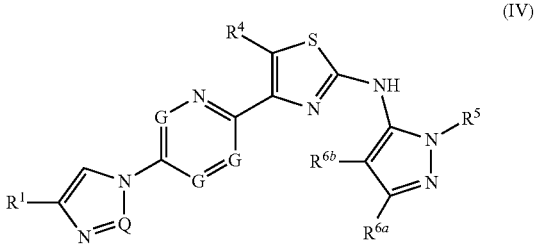

In this embodiment,
$R^1$ may be a halogen or substituted or unsubstituted $C_1$-$C_5$ alkyl. $R^4$ may be a hydrogen, halogen, substituted or unsubstituted alkyl, substituted or unsubstituted cycloalkyl, substituted or unsubstituted aryl, or substituted or unsubstituted alkoxy. $R^5$ may be a hydrogen, a substituted or unsubstituted alkyl, or substituted or unsubstituted cycloalkyl. Additionally, $R^{6a}$ and $R^{6b}$ may be independently a hydrogen, substituted or unsubstituted alkyl, or substituted or unsubstituted cycloalkyl.

In yet another embodiment of the invention, the compound may have a structure corresponding to Formula (V):

(V)

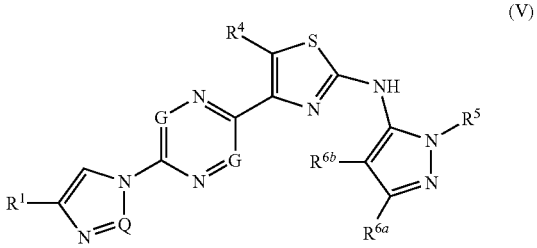

In this embodiment, $R^1$ may be a halogen or substituted or unsubstituted $C_1$-$C_5$ alkyl. $R^4$ may be a hydrogen, halogen, substituted or unsubstituted alkyl, substituted or unsubstituted cycloalkyl, substituted or unsubstituted aryl, or substituted or unsubstituted alkoxy. Also, $R^5$ may be a hydrogen, substituted or unsubstituted alkyl, or substituted or unsubstituted cycloalkyl. Further, $R^{6a}$ and $R^{6b}$ may be independently a hydrogen, substituted or unsubstituted alkyl, or substituted or unsubstituted cycloalkyl.

Additionally, the group that occupies the D position in Formula I, II, III, IV, and/or V, includes but is not limited to any of:

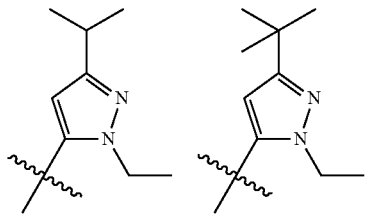

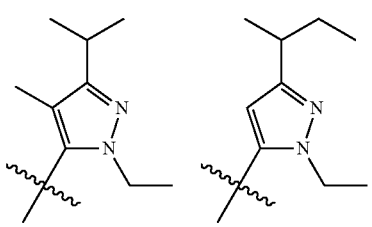

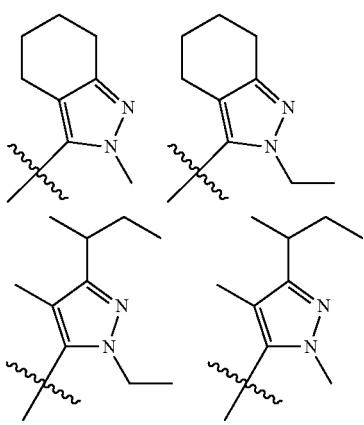

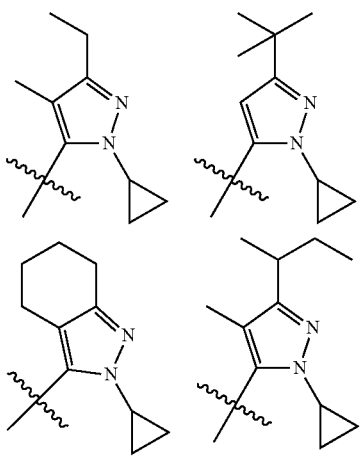

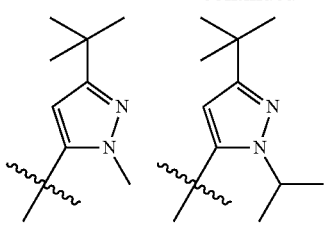

-continued

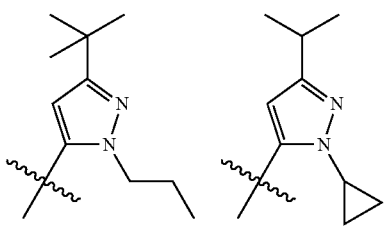

In another embodiment, the compound of Formula IV has the following structure:

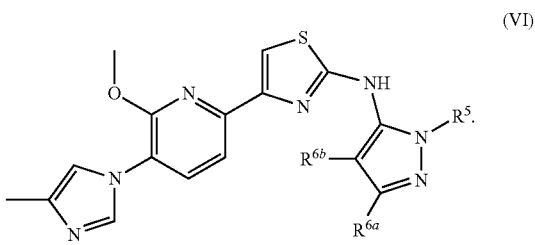

(VI)

In this embodiment, $R^5$ may be a hydrogen, substituted or unsubstituted alkyl, or substituted or unsubstituted cycloalkyl; and $R^{6a}$ and $R^{6b}$ may be independently a hydrogen, substituted or unsubstituted alkyl, or substituted or unsubstituted cycloalkyl.

In yet a further embodiment, the structure corresponding to formula VI is a compound that has a structure corresponding to Formula (VII):

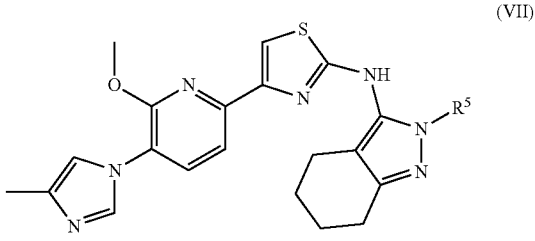

(VII)

In this embodiment, $R^5$ may be a hydrogen, substituted or unsubstituted alkyl, or substituted or unsubstituted cycloalkyl.

Specific embodiments of compounds having the structure corresponding to Formula (VII) include but are not limited to:

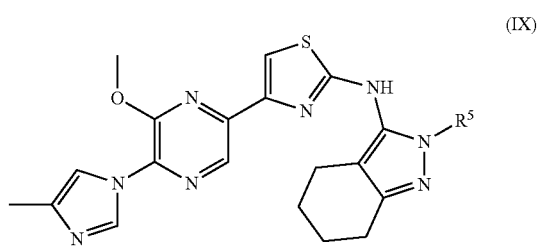

In this embodiment, R⁵ may be a hydrogen, substituted or unsubstituted alkyl, or substituted or unsubstituted cycloalkyl.

Specific embodiments of compounds having the structure corresponding to Formula (IX) include but are not limited to

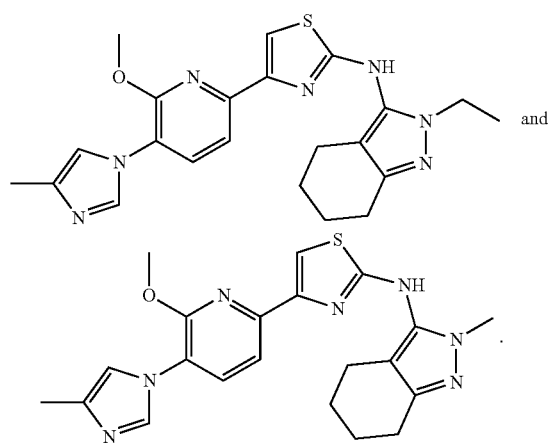

Specific embodiments of compounds having the structure corresponding to Formula (VI) include but are not limited to

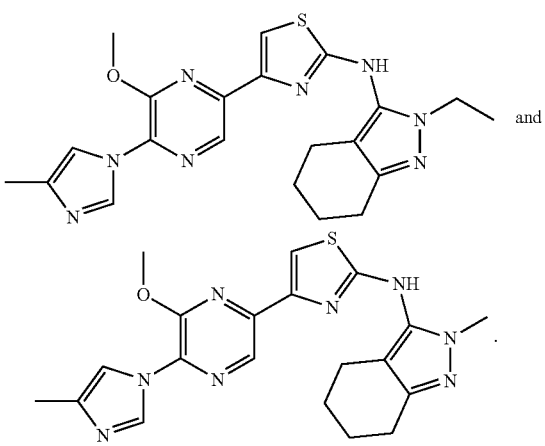

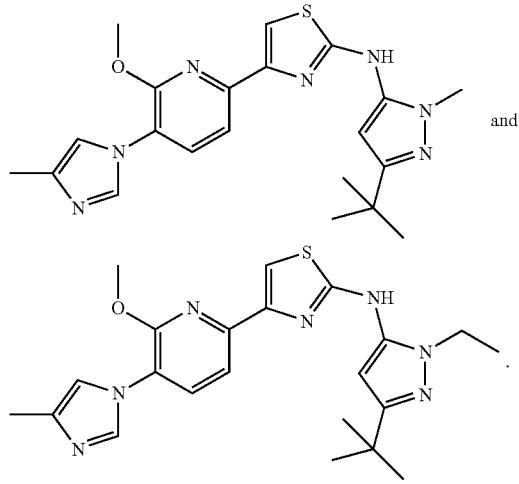

Specific embodiments of compounds having the structure corresponding to Formula (VIII) include but are not limited to

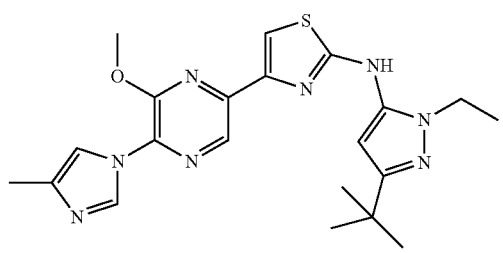

In yet a further embodiment, the structure corresponding to formula V is a compound that has a structure corresponding to Formula (VIII):

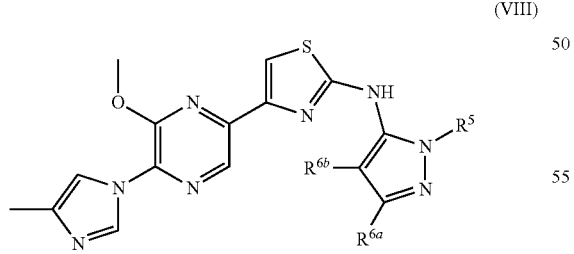

In this embodiment, R⁵ may be a hydrogen, substituted or unsubstituted alkyl, or substituted or unsubstituted cycloalkyl; and $R^{6a}$ and $R^{6b}$ may be independently a hydrogen, substituted or unsubstituted alkyl, or substituted or unsubstituted cycloalkyl.

In yet a further embodiment, the structure corresponding to formula VIII is a compound that has a structure corresponding to Formula (IX):

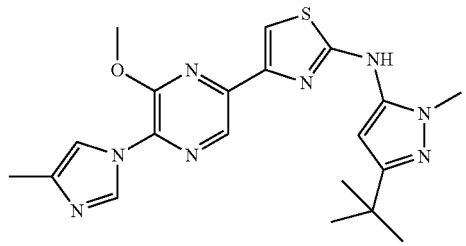

-continued

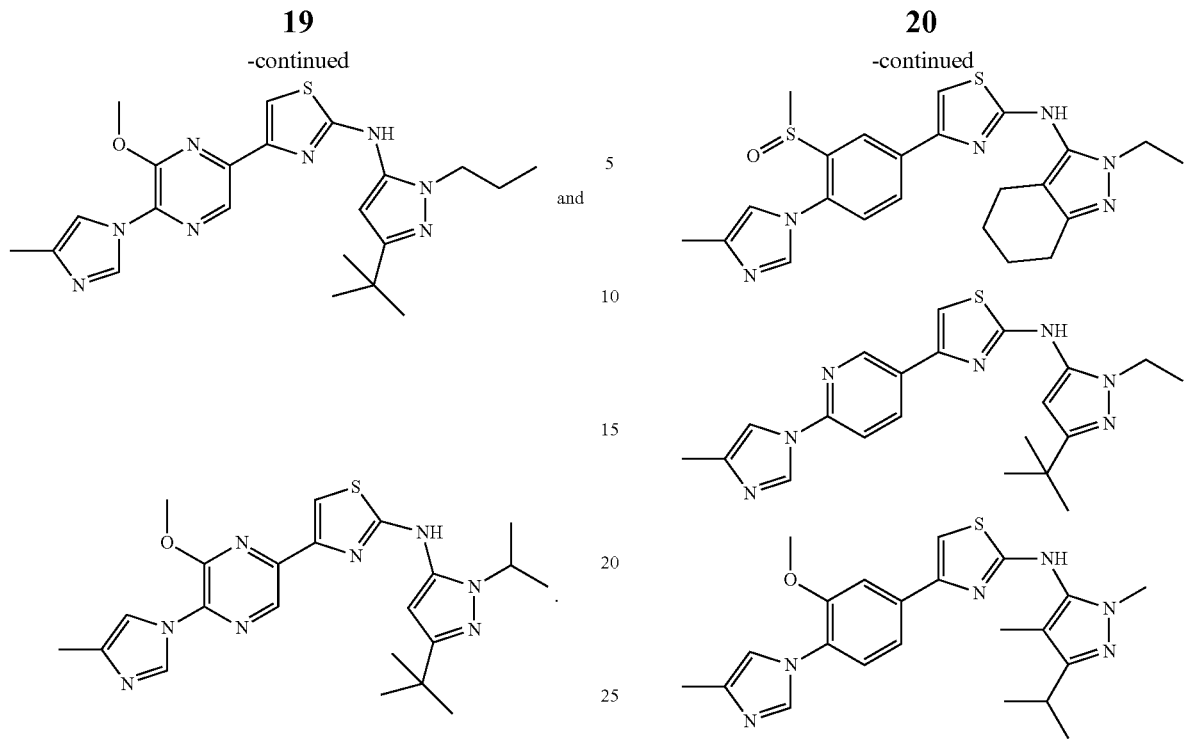

Specific embodiments of compounds having the structure corresponding to Formula (II) include but are not limited to

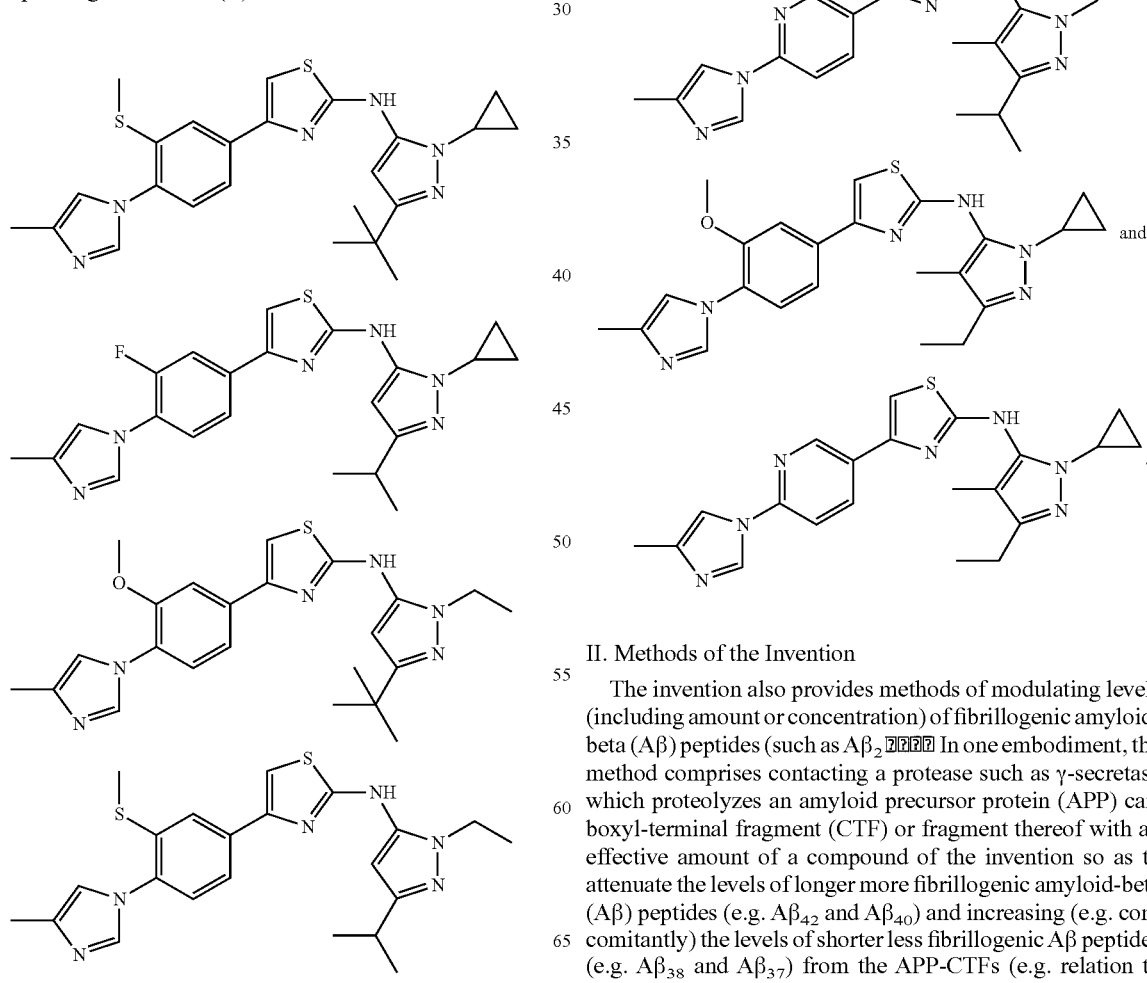

II. Methods of the Invention

The invention also provides methods of modulating levels (including amount or concentration) of fibrillogenic amyloid-beta (Aβ) peptides (such as Aβ₂ ▮▮▮▮ In one embodiment, the method comprises contacting a protease such as γ-secretase which proteolyzes an amyloid precursor protein (APP) carboxyl-terminal fragment (CTF) or fragment thereof with an effective amount of a compound of the invention so as to attenuate the levels of longer more fibrillogenic amyloid-beta (Aβ) peptides (e.g. Aβ$_{42}$ and Aβ$_{40}$) and increasing (e.g. concomitantly) the levels of shorter less fibrillogenic Aβ peptides (e.g. Aβ$_{38}$ and Aβ$_{37}$) from the APP-CTFs (e.g. relation to Aβ$_{42}$ and Aβ$_{40}$).

The invention provides methods for treating a disease or neurological disorder associated with elevated levels of specific fibrillogenic Aβ peptides (e.g., $A\beta_{42}$ and/or $A\beta_{40}$) comprising administering to a subject in need thereof an effective amount of any of the compounds of the invention (any of the compounds of Formulas I-XI) so as to treat the disease. In one embodiment, the disease is treated by modulating the levels of the Aβ peptides in the subject. In accordance with the practice of the invention, the compound may be a prodrug.

Examples of diseases associated with elevated levels of specific fibrillogenic Aβ peptides include but are not limited to Alzheimer's disease, hemorrhagic stroke associated with cerebrovascular amyloidosis (HCHWA), or cerebral amyloid angiopathy (CAA), idiopathic dilated cardiomyopathy, Down Syndrome (DS), Parkinson's Disease (PD), Lewy Body Dementia (LBD), Prion Diseases, Inclusion Body Myositis (IBM) and Hunington's Disease (HD).

The phrase "amyloid-beta" or "Aβ" refers to a peptide from a human or other species that (a) results from processing or cleavage of an APP-CTF that is amyloidogenic, (b) is one of the peptide constituents of R-amyloid plaques, (c) is the 42-amino acid sequence of Aβ (amino acid 672-713 of APP770; GenBank Accession No. P05067), (d) is a fragment of a peptide as set forth in (a), (b) or (c), and/or (e) contains one or more additions, deletions or substitutions relative to (a), (b), (c) or (d). Aβ is also referred to in the art as .βAP, AβP, A4 or βA4. Aβ peptides derived from proteolysis of an APP-CTF, generally are about 4.2 kD proteins and are typically 39 to 43 amino acids in length, depending on the carboxy-terminal end-point, which exhibits heterogeneity. However, Aβ peptides containing less than 39 amino acids, e.g., $A\beta_{38}$, $A\beta_{37}$, and $A\beta_{34}$, also may occur.

Aβ peptides can be produced in an amyloidogenic APP processing pathway in which APP is cleaved by β-secretase (RACE) and one or more gamma-secretase activities. Aβ peptides include those but are not limited to those that begin at position 672 of APP770 and those that begin at position 682 of APP770 (see, for example, GenBank Accession No. P05067). Generally, as used herein, "Aβ" includes any and all Aβ peptides, unless the amino acid residues are specified, such as, for example, 1-43 ($A\beta_{43}$), 1-42 ($A\beta_{42}$), 1-40 ($A\beta_{40}$), 1-39 ($A\beta_{39}$), 1-38 ($A\beta_{38}$), 1-37 ($A\beta_{37}$), 1-34 ($A\beta_{34}$). Additionally amino-terminally-truncated Aβ peptides exists such as 11-43, 11-42, 11-40, 11-39, 11-38, 11-37, 11-34, and other. The various Aβ peptides of differing lengths are referred to herein as "species" of Aβ.

The phrase "amyloid precursor protein" or "APP" refers to a protein that can be proteolytically processed or cleaved by one or more processing or cleavage reactions to produce Aβ. APP includes all isoforms that are generated by alternative splicing, which can be typically distinguished by the number of amino acids in the particular isoform. For example, APP embraces APP695, APP751, and APP770. Other isoforms of APP include, for example, APP714, L-APP752, L-APP733, L-APP696, L-APP677, APP563, and APP365.

APP also includes all isoforms containing mutations found in families with AD and other amyloidosis conditions. For example, these mutations include the Swedish (Lys670Asn, Met671Leu) double mutation; the London mutation (Val717Ile), the Indiana mutation (Val717Leu), Val717Phe, Val717Gly, Ala713Thr, Ala713Val, the Austrian mutation (Thr714Ile), the Iranian mutation (Thr714Ala), the French mutation (Val715Met), the German mutation (Val715Ala), the Florida mutation (Ile716Val), Ile 716Thr, the Australian mutation (Leu723Pro), the Flemish mutation (Ala692Gly), the Dutch mutation (Glu693Gln), the Arctic mutation (Glu693Gly), the Italian mutation (Glu693Lys), and the Iowa mutation (Asp694Asn), and the amyloidsis-Dutch type mutation (Glu693Gln). (All numbering herein is relative to the APP770 form).

The term "APP" further includes proteins containing one or more additions, deletions or substitutions relative to the isoforms described above, and APP proteins from humans and other species. Unless a specific isoform is specified, APP when used herein generally refers to any and all isoforms of APP, with or without mutations, from any species.

The phrase "amyloid precursor protein fragment" refers to any portion of an APP that can be processed or cleaved, by one or more processing or cleavage reactions, to produce Aβ. Amyloid precursor protein fragments of APP generally contain either a beta-secretase cleavage site which, when cleaved, generates the N-terminus of Aβ, a gamma-secretase cleavage site which, when cleaved, generates the C-terminus of Aβ or both a beta- and a gamma-secretase cleavage site. Exemplary amyloid precursor fragments include the APP C-terminal fragments designated C99 and C83, as well as portions thereof lacking some or all C-terminal residues that normally reside in the cytosol.

The phrase "source of amyloid precursor protein (APP), amyloid precursor fragment thereof and/or Aβ" refers to any in vivo, ex vivo or in vitro substance containing APP, amyloid precursor fragment thereof and/or Aβ. For example, a "source" can be a live organism (including a human patient, or a laboratory or veterinary animal, such as dog, pig, cow, horse, rat or mice), a sample therefrom (such as a tissue or body fluid, or extract thereof), a cell (such as a primary cell or cell line, or extract thereof), extracellular medium or matrix or milieu, or isolated protein.

The phrase "modulate" or "modulating" with respect to Aβ level, refers to a detectable increase or decrease in the amount (or level) of at least one species of the Aβ peptide (such as $A\beta_{43}$, $A\beta_{42}$, $A\beta_{40}$, $A\beta_{39}$, $A\beta_{38}$, $A\beta_{37}$, $A\beta_{34}$, etc.); a detectable increase or decrease in the relative amount (or level) of different species of Aβ peptides (such as the ratio of $A\beta_{42}$ to $A\beta_{40}$); a detectable increase or decrease in the amount, or relative amount, of Aβ in a particular form (such as monomeric, oligomeric, or fibrillar form; in solution or aggregated in a plaque; in a particular conformation; etc.); and/or a detectable increase or decrease in the amount, or relative amount, of a particular Aβ species in a particular location (such as an intracellular, membrane-associated or extracellular location, or in a particular tissue or body fluid). In preferred embodiments, modulation is detectable as a decrease in the level of $A\beta_{42}$ or $A\beta_{40}$, or an increase in the level of $A\beta_{37}$ or $A\beta_{38}$. Modulation of Aβ levels can be evidenced, for example, by an increase or decrease of at least 5%, such as at least 10%, 20%, 30%, 40%, 50%, 75%, 90% or more, of the amount, or relative amount, of an Aβ species, or of a particular form of Aβ, relative to a reference level. Modulation can be an increase or decrease that is a statistically significant difference relative to the reference level.

The phrase "contacting" refers to bringing into association, either directly or indirectly, two or more substances. Contacting may occur in vivo, ex vivo or in vitro. A source of APP, amyloid precursor fragment thereof and/or Aβ or source of gamma-secretase activity, that is a human or other animal can be contacted with a compound, for example, by therapeutic or prophylactic administration of the compound. A source of APP, amyloid precursor fragment thereof and/or Aβ that is a tissue, tissue extract or cell can be contacted with a compound, for example, by introduction of the compound into the culture medium. A source of APP, amyloid precursor fragment thereof and/or Aβ that is a fluid, such as extracellular medium, can be contacted with a compound, for example, by admixing the compound with the fluid.

The phrase "treating" or "treatment" refers to any manner in which one or more of the symptoms of a disease or disorder are ameliorated or otherwise beneficially altered, whether in a permanent or temporary manner, which can be attributed to or associated with administration of the compound or composition herein. The term encompasses any pharmaceutical use, including prophylactic uses in which the development of one or more of the symptoms of a disease or disorder is prevented, delayed or reduced, whether in a permanent or temporary manner, which can be attributed to or associated with administration of the composition. In an embodiment of the invention, treatment encompasses any pharmaceutical use of compounds herein for treating a disease or disorder characterized by altered or aberrant Aβ production, catabolism, processing and/or levels.

The phrase "disease associated with aberrant Aβ levels" refers to any condition characterized by an abnormal amount of at least one species of Aβ peptide (such as $A\beta_{43}$, $A\beta_{42}$, $A\beta_{40}$, $A\beta_{39}$, $A\beta_{38}$, $A\beta_{37}$, $A\beta_{34}$, etc.); by an abnormal relative amount of different species of Aβ peptides (such as the ratio of $A\beta_{42}$ to $A\beta_{40}$); by an abnormal amount, or relative amount, of Aβ in a particular form (such as monomeric, oligomeric, or fibrillar form; in solution or aggregated in a plaque; in a particular conformation, etc.); and/or by an abnormal amount, or relative amount, of Aβ in a particular location (such as intracellular, membrane-associated or extracellular location, or in a particular tissue or body fluid). The abnormal amount of one or more Aβ peptides, Aβ forms and/or Aβ can be relative to a condition that is a normal, non-disease state. Diseases and disorders characterized by altered Aβ levels are known in the art and/or described herein, and include, for example, Down syndrome, Alzheimer's disease (AD), diffuse Lewy body disease, Hereditary Cerebral Hemorrhage with Amyloidosis-Dutch Type (HCHWA-D), cerebral amyloid angiopathy (CAA), and mild cognitive impairment (MCI), Embodiments of the invention include methods of treating any disease associated with aberrant Aβ levels, such as AD. Compounds of the present invention can be administered to a subject to treat (including to prevent or to ameliorate) conditions associated with altered Aβ production, fibril formation/deposition, degradation and/or clearance, or any altered isoform of Aβ.

Preferably, compounds of the present invention can be used in the treatment of neurological disorders, including but not limited to neurodegenerative conditions and other dementias or traumatic conditions. Exemplary neurological disorders may include diffuse Lewy body disease, Pick's disease, multisystem degeneration (Shy-Drager syndrome), motor neuron diseases including amyotrophic lateral sclerosis, degenerative ataxias, cortical basal degeneration, ALS-Parkinson's-Dementia complex of Guam, subacute sclerosing panencephalitis, Huntington's disease, synucleinopathies, primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, prion diseases (including Creutzfeldt-Jakob, Gerstmann-Straussler-Scheinker disease, Kuru and fatal familial insomnia), age-related dementia and other conditions with memory loss, such as vascular dementia, diffuse white matter disease (Binswanger's disease), dementia of endocrine or metabolic origin, dementia of head trauma and diffuse brain damage, dementia pugilistica and frontal lobe dementia, cerebral ischemia or infection including embolic occlusion and thrombotic occlusion as well as intracranial hemorrhage of any type (including, but not limited to, epidural, subdural, subarachnoid and intracerebral), and intracranial and intravertebral lesions (including, but not limited to, contusion, penetration, shear, compression and laceration).

III. Screening Assays

The invention also provides methods for screening for GSMs that (a) modulate levels of fibrillogenic amyloid-beta and less fibrillogenic (Aβ) peptides, (b) do not inhibit the proteolysis of NOTCH and the NOTCH signaling pathway, and (c) compete with any of the compounds of the invention for a common site on the APP-CTF-processing enzyme γ-secretase. In one embodiment, the proteolysis of NOTCH is not inhibited and NOTCH signaling is effected through a NOTCH intracellular domain (NICD).

IV. Pharmaceutical Compositions

The phrase "pharmaceutically acceptable carrier" refers to any carrier known to those skilled in the art to be suitable for the particular mode of administration. In addition, the compounds may be formulated as the sole pharmaceutically active ingredient in the composition or may be combined with other active ingredients.

The phrase "pharmaceutically acceptable salt" refers to any salt preparation that is appropriate for use in a pharmaceutical application. Pharmaceutically-acceptable salts include amine salts, such as N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chloro-benzyl-2-pyrrolidin-1'-ylmethylbenzimidazole, diethylamine and other alkylamines, piperazine, tris(hydroxymethyl)aminomethane, and the like; alkali metal salts, such as lithium, potassium, sodium, and the like; alkali earth metal salts, such as barium, calcium, magnesium, and the like; transition metal salts, such as zinc, aluminum, and the like; other metal salts, such as sodium hydrogen phosphate, disodium phosphate, and the like; mineral acids, such as hydrochlorides, sulfates, and the like; and salts of organic acids, such as acetates, lactates, malates, tartrates, citrates, ascorbates, succinates, butyrates, valerates, fumarates, and the like.

The phrase "prodrug" refers to a compound that, upon in vivo administration, is metabolized by one or more steps or processes or otherwise converted to the biologically, pharmaceutically or therapeutically active form of the compound. Prodrugs can be prepared by modifying functional groups present in the compound in such a way that the modifications are cleaved, either in routine manipulation or in vivo, to a compound described herein. For example, prodrugs include compounds of the present invention wherein a hydroxy, amino, or sulfhydryl group is bonded to any group that, when administered to a mammalian subject, can be cleaved to form a free hydroxyl, free amino, or free sulfhydryl group, respectively. Representative prodrugs include, for example, esters, enol ethers, enol esters, acetates, formates, benzoate derivatives, and the like of alcohol and amine functional groups in the compounds of the present invention. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388 392).

Compositions herein comprise one or more compounds provided herein. The compounds are, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers, In one embodiment, the compounds described above are formulated into pharmaceutical compositions using techniques and procedures well known in the art (see, e.g., Ansel Introduction to Pharmaceutical Dosage Forms, Fourth Edition 1985, 126).

In the compositions, effective concentrations of one or more compounds or pharmaceutically acceptable derivatives thereof is (are) mixed with a suitable pharmaceutical carrier. The compounds may be derivatized as the corresponding salts, esters, enol ethers or esters, acetals, ketals, orthoesters, hemiacetals, hemiketals, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders to be treated.

In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and in PCT publication WO 04/018997, and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art.

In one embodiment, a therapeutically effective dosage may produce a serum concentration of active ingredient of from about 0.1 ng/ml to about 50 100 .mu.g/ml. The pharmaceutical compositions, in another embodiment, may provide a dosage of from about 0.001 mg to about 2000 mg of compound per kilogram of body weight per day, Pharmaceutical dosage unit forms are prepared and may provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN™, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing active ingredient in the range of 0.005% to 100% (wt %) with the balance made up from non-toxic carrier may be prepared. Methods for preparation of these compositions are known to those skilled in the art. The contemplated compositions may contain 0.001% 100% (wt %) active ingredient, in one embodiment 0.1 95% (wt %), in another embodiment 75 85% (wt %).

A. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

1. Solid Compositions for Oral Administration

In certain embodiments, the formulations are solid dosage forms, in one embodiment, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polyinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammuonianted shellac and cellulose acetate phthalates. Film coatings include hydroxyethylcellulose, sodium carboxymethylcellulose, polyethylene glycol 4000 and cellulose acetate phthalate.

The compound, or pharmaceutically acceptable derivative thereof, could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

2. Liquid Compositions for Oral Administration

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous-liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is in one embodiment encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358, 603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl)acetals of lower alkyl aldehydes such as acetaldehyde diethyl acetal.

B. Injectables, Solutions and Emulsions

Parenteral administration, in one embodiment characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained is also contemplated herein. Briefly, a compound provided herein may be dispersed e.g., in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection.

Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN™ 80). A sequestering or chelating agent of metal ions include EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

C. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4.degree. C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

D. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01% 10% (vol %) isotonic solutions, pH about 5 7, with appropriate salts.

E. Compositions for Other Routes of Administration

Other routes of administration, such as transdermal patches, including iontophoretic and electrophoretic devices, and rectal administration, are also contemplated herein.

Transdermal patches, including iotophoretic and electrophoretic devices, are well known to those of skill in the art. For example, such patches are disclosed in U.S. Pat. Nos. 6,267,983, and 5,860,957.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration are manufactured using the same pharmaceutically acceptable substance and by the same methods as for formulations for oral administration F. Targeted Formulations The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

G. Combination Therapy

In another embodiment, the compounds may be administered in combination, or sequentially, with another therapeutic agent. Such other therapeutic agents include those known for treatment, prevention, or amelioration of one or more symptoms of amyloidosis and neurodegenerative diseases and disorders. Such therapeutic agents include, but are not limited to, donepezil hydrochloride (Aricept), rivastigmine tartrate (Exelon), tacrine hydrochloride (Cognex) and galantamine hydrobromide (Reminyl).

V. Kits

According to another aspect of the invention, kits are provided. Kits according to the invention include package(s) comprising compounds or compositions of the invention.

The phrase "package" means any vessel containing compounds or compositions presented herein. In preferred embodiments, the package can be a box or wrapping. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment.

The kit can also contain items that are not contained within the package but are attached to the outside of the package, for example, pipettes.

Kits may optionally contain instructions for administering compounds or compositions of the present invention to a subject having a condition in need of treatment. Kits may also comprise instructions for approved uses of compounds herein by regulatory agencies, such as the United States Food and Drug Administration. Kits may optionally contain labeling or product inserts for the present compounds. The package(s) and/or any product insert(s) may themselves be approved by regulatory agencies. The kits can include compounds in the solid phase or in a liquid phase (such as buffers provided) in a package. The kits also can include buffers for preparing solutions for conducting the methods, and pipettes for transferring liquids from one container to another.

The kit may optionally also contain one or more other compounds for use in combination therapies as described herein. In certain embodiments, the package(s) is a container for intravenous administration. In other embodiments, compounds are provided in an inhaler. In still other embodiments compounds are provided in a polymeric matrix or in the form of a liposome.

VI. Preparation of Compounds

Presented below are exemplary general SCHEMES for the preparation of invention compounds, further details of synthetic methods are provided in the examples herein. Since compounds herein can be readily prepared according to procedures well known to one of ordinary skill in the art, numerous methods, in lieu of or in addition to the synthetic SCHEMEs presented below, may be employed to prepare compounds herein.

Derivatives and chemically similar compounds within the scope of the instant disclosure may be prepared by routine modification of the procedures provided herein using the appropriate starting materials, the selection of which will be evident to those of skill in the art.

A. General Condensation Scheme:

Compounds herein which comprise an aminothiazole moiety can be prepared (SCHEME 1) by combining a halogenated ketone derivative (1) with an appropriate thiourea compound (2).

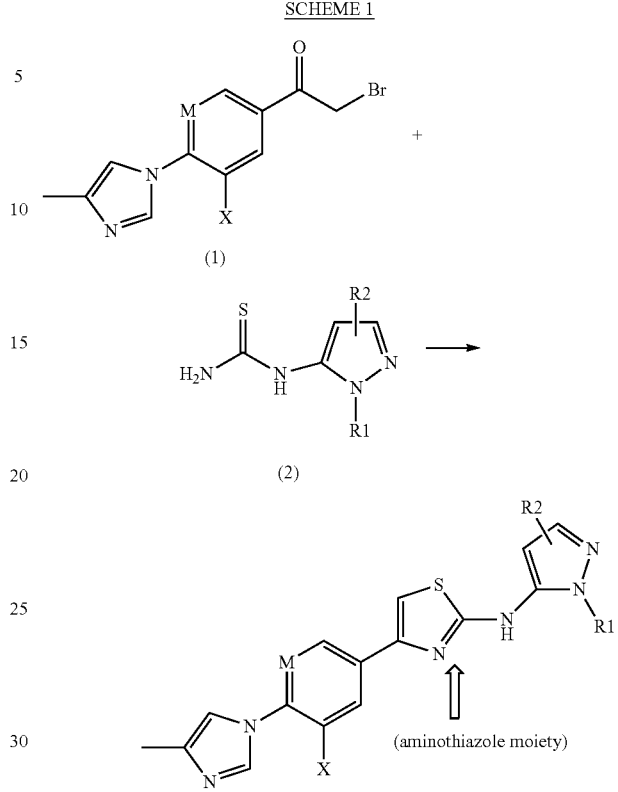

B. Preparation of α-Bromoketone Derivatives:

α-bromoketone derivatives where ring B is a phenyl derivative can be prepared according to SCHEME 2.

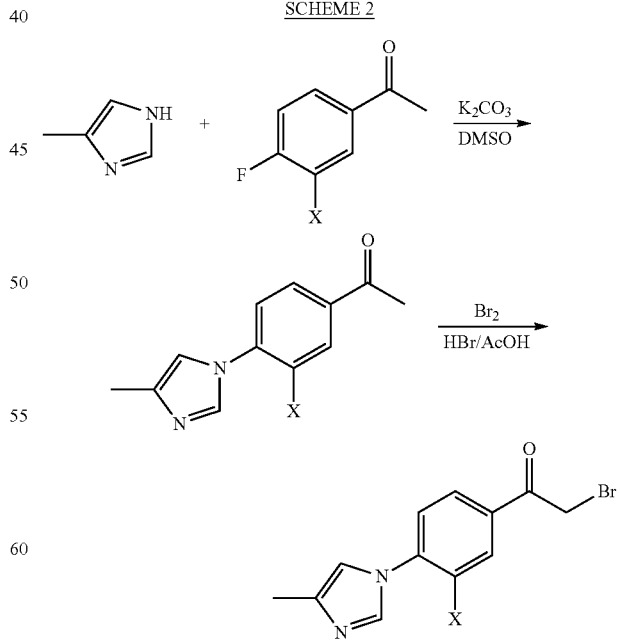

α-bromoketone derivatives where ring B is a pyridyl derivative can be prepared according to SCHEME 3.

SCHEME 3

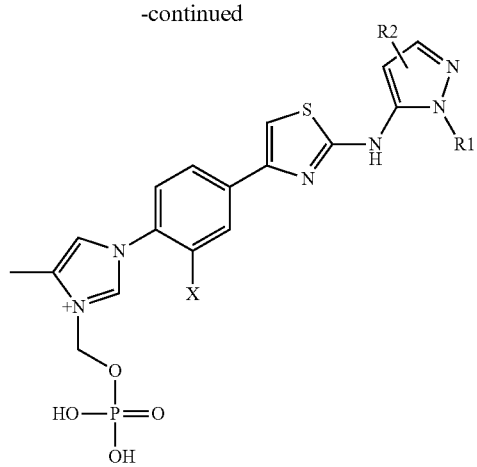

Preparation of Thiourea Derivatives:

Thiourea derivatives are employed in the general condensation reaction depicted in SCHEME 1 and can be prepared by SCHEME 4.

SCHEME 4

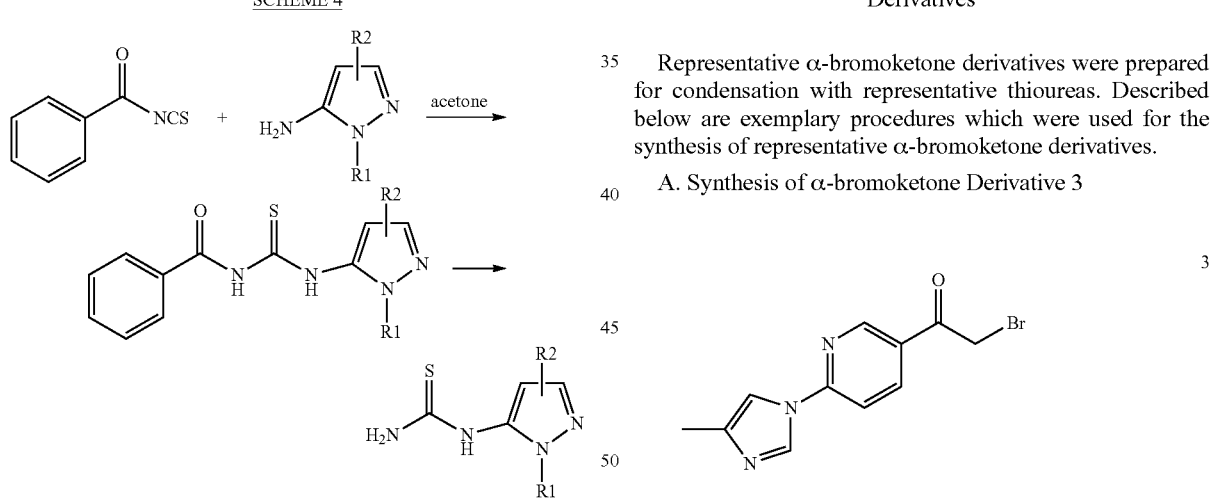

Preparations of Prodrugs:

SCHEME 5

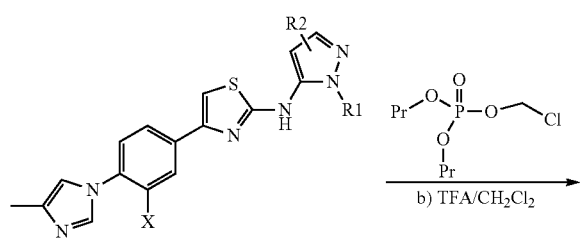

The following examples are provided to further illustrate aspects of the invention. These examples are non-limiting and should not be construed as limiting any aspect of the invention.

EXAMPLES

Example 1

Preparation of Representative α-Bromoketone Derivatives

Representative α-bromoketone derivatives were prepared for condensation with representative thioureas. Described below are exemplary procedures which were used for the synthesis of representative α-bromoketone derivatives.

A. Synthesis of α-bromoketone Derivative 3

SCHEME 6

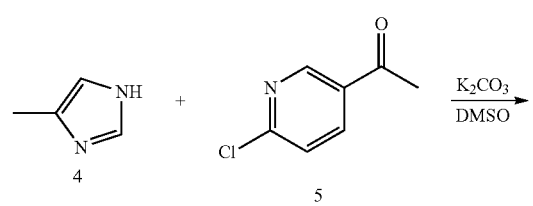

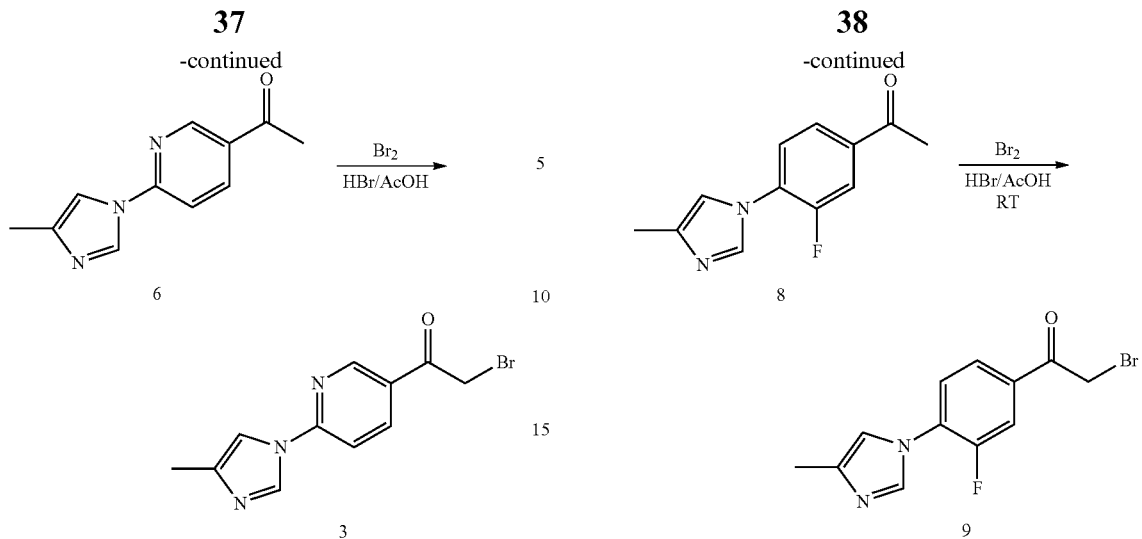

1-(6-chloro-pyridin-3-yl)-ethanone 5 (7.0 g, 45.2 mmol) and 4-methyliminazole 4 (11.1 g, 135.5 mmole) were combined in DMSO (35 mL), followed by addition of $K_2CO_3$. The mixture was heated at 110° C. for 22 h. The reaction mixture was then cooled to room temperature and poured into ice water (400 mL) with vigorous stirring for 15 min. The resulting precipitate was collected on a filter and washed with water. The resulting material was dried in vacuo to yield 6 as a tan solid (6.1 g, 67%). LC/MS: [m+1]+=202.2, $^1$H NMR (DMSO-d6) 300 MHz δ2.18 (3H, s), 2.63 (3H, s), 7.72 (1H, s), 7.87 (1H, d, J=9.0 Hz), 8.41 (1H, d, J=9.0 Hz), 8.51 (1H, s), 8.98 (1H, s).

Compound 6 (6.1 g, 30.3 mmole) was suspended in 30% HBr/AcOH (75 mL). Bromine (4.8 g, 30.3 mmole) was added dropwise over 1 h. The reaction mixture was stirred at room temperature for 2 h, poured into 600 mL of ice water and stirred for 15 min. The resulting precipitate was collected on a filter and washed with water. The compound was dried to yield 3 as a yellow solid (10.6 g, 80%). LC/MS: [M+1]$^+$= 282.1. $^1$H NMR (DMSO-d6) 300 MHz δ2.36 and 2.37 (3H, two s), 5.06 (2H, s), 8.16 (1H, d, J=9.0 Hz), 8.29 (1H, s), 8.69 (1H, d, J=9.0 Hz), 9.15 (1H, s), 9.93 (1H, s).

B. Synthesis of α-bromoketone Derivative 9

To a solution of 4-methylimidazole 4 (28.5 g, 347 mmole) in DMSO (200 ml), $K_2CO_3$ (132 g, 955 mmol) and 1-(3,4-difluoro-phenyl)-ethanone 7 (50.0 g, 320 mmole) were added. The reaction mixture was heated and stirred at 55° C. for 16 h. The reaction mixture was allowed to cool to room temperature and water (600 mL) was added. The reaction mixture was stirred for another 60 min. The precipitate was collected, washed with water (~2 L) and dried under vacuum overnight to yield the crude product. Recrystallization of the crude product afforded the desired product 8 (32.5 g, 59% yield).

To a solution of compound 8 (37.5 g, 171.8 mmol) in HBr (30% in HOAc, 400 mL) was added bromine (27.5 g, 8.81 mL, 171.8 mmol) dropwise with stirring over a period of 60 min. The reaction mixture was stirred for another 40 min. and the reaction mixture was concentrated to remove most of the HBr and HOAc. The crude material was re-dissolved in methanol (300 mL) and then concentrated under vacuum in order to remove the rest of HBr and HOAc. The crude product was added water and the suspension was filtered, dried under vacuum overnight to give the desired product 9 (43.5 g, 67% yield).

Example 2

Preparation of Representative Novel Compounds

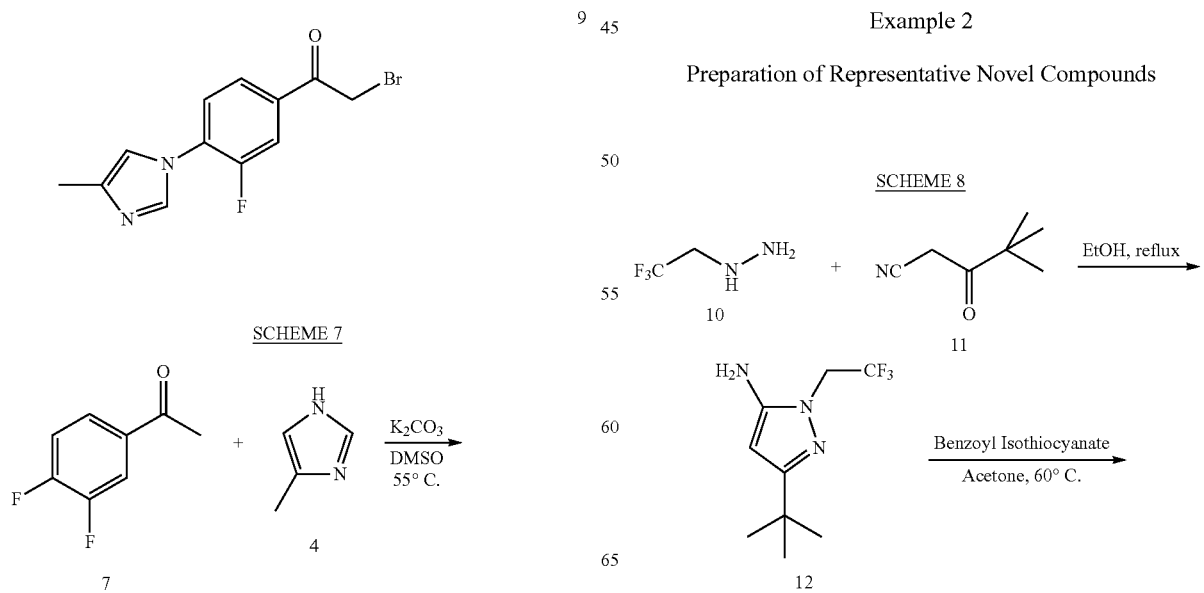

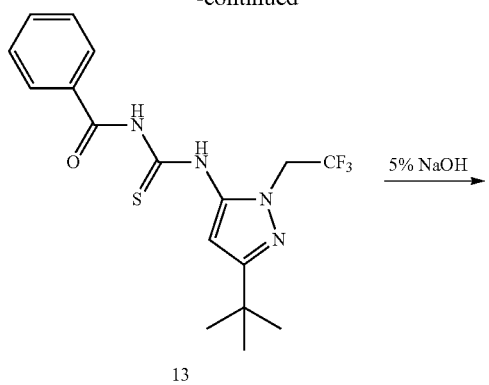

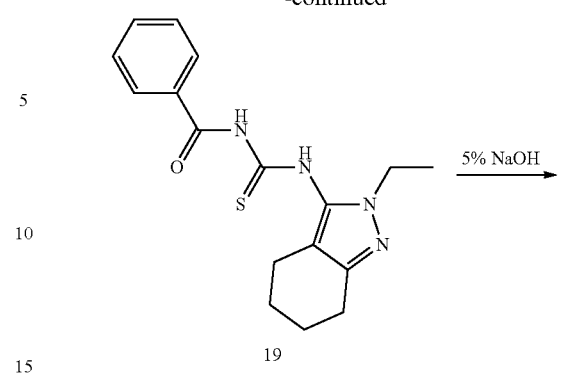

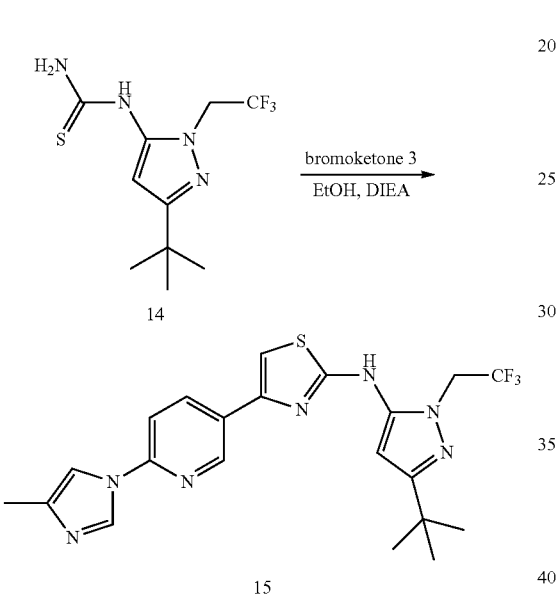

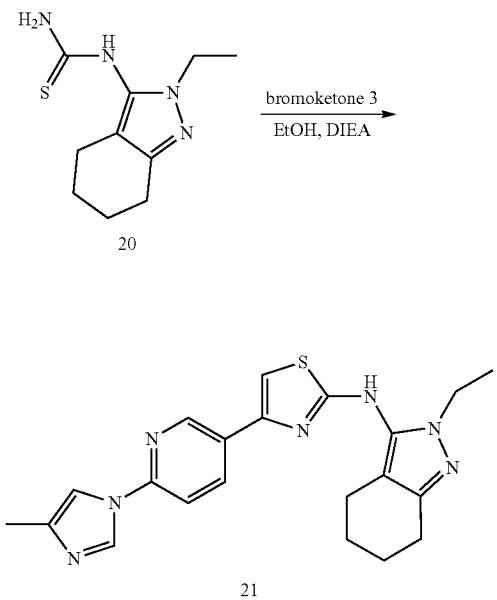

The coupling of 2,2,2-trifluoroethylhydrazine 10 and pivaloylacetonitrile 11 in ethanol under reflux gave 12. After coupling of 12 with benzoyl isothiocyanate followed by the alkaline hydrolysis, the resulting thiourea 14 was coupled with α-bromoketone 9 to give the desired product 15.

The coupling of ethylhydrazine 16 with acetonitrile 17 in ethanol under reflux gave 18. Coupling of 18 with benzoyl isothiocyanate yield the benzoyl thiourea 19 in excellent yield. Alkaline hydrolysis of 19 yielded thiourea 20. Reaction of bromoketone 3 with thiourea 20 afforded 21.

SCHEME 9

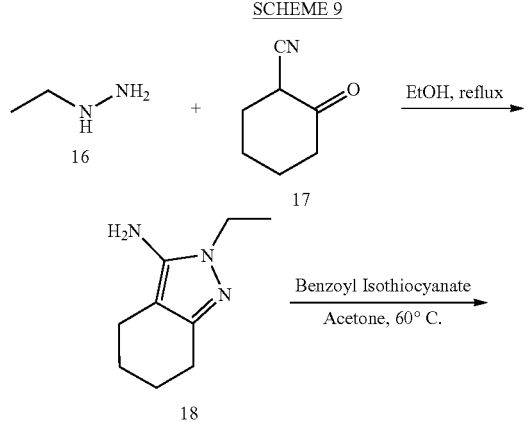

SCHEME 10

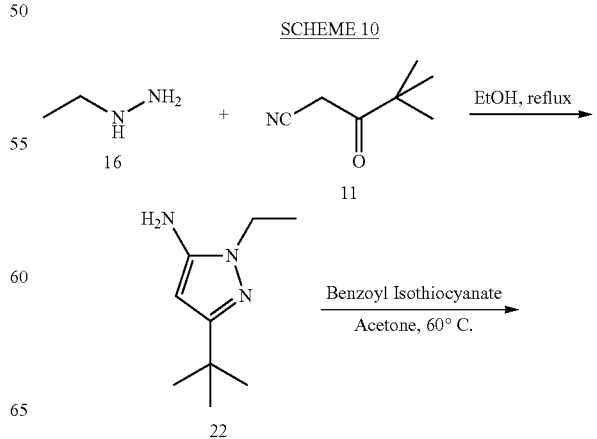

-continued

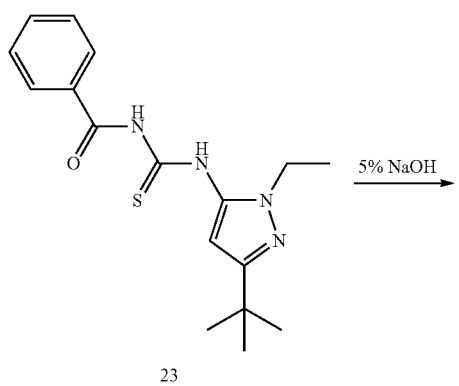

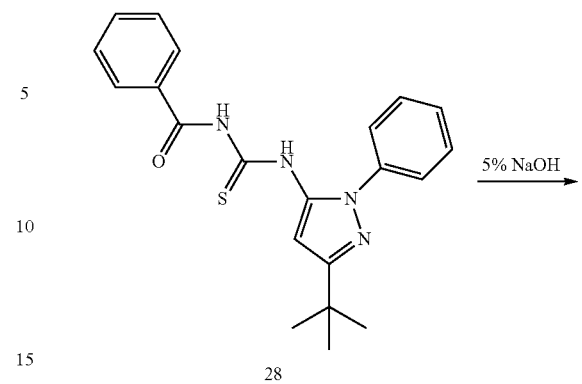

The coupling of ethylhydrazine 16 with acetonitrile 11 in ethanol under reflux gave 22. Coupling of 22 with benzoyl isothiocyanate yield the benzoyl thiourea 23 in excellent yield. Alkaline hydrolysis of 23 yielded thiourea 24. Reaction of bromoketone 9 with thiourea 24 afforded 25.

The coupling of phenylhydrazine 26 with acetonitrile 11 in ethanol under reflux gave 27. Coupling of 27 with benzoyl isothiocyanate yield the benzoyl thiourea 28 in excellent yield. Alkaline hydrolysis of 28 yielded thiourea 29. Reaction of bromoketone 3 with thiourea 29 afforded 30.

Example 3

Preparation of Representative Prodrugs

SCHEME 11

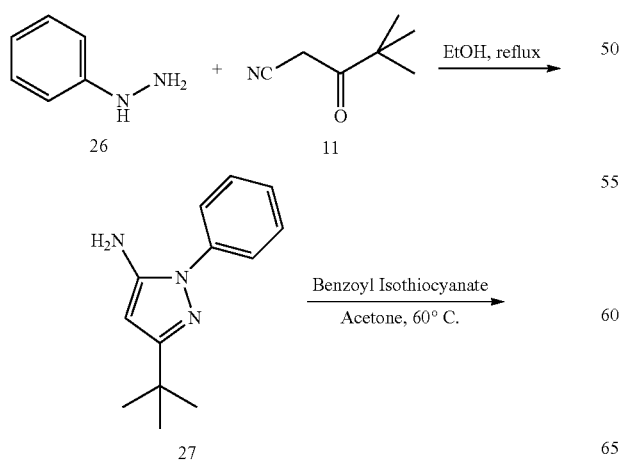

SCHEME 12

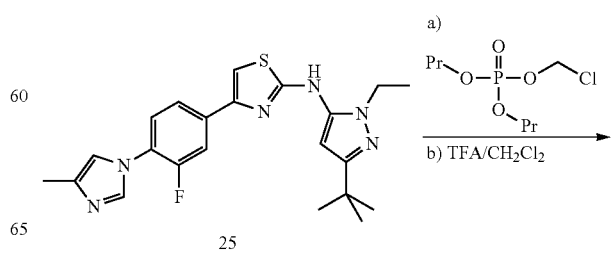

-continued

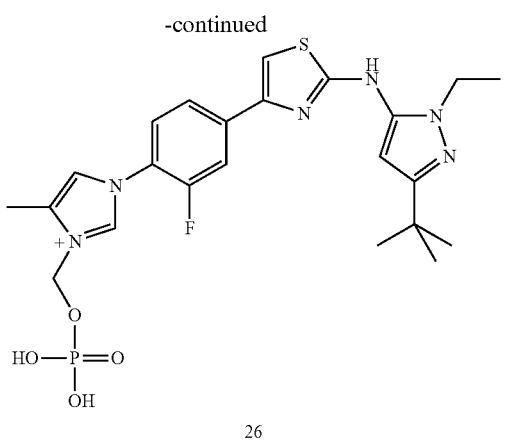

26

The phosphonooxymethyl ether derivative of compound 25 was prepared from chloromethyl phosphate followed by cleavage of the protecting ester moiety (SCHEME 12).

SCHEME 13

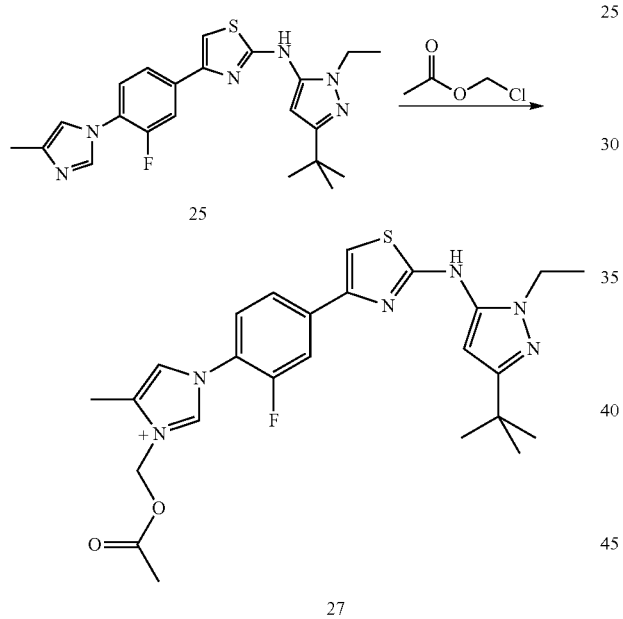

Reaction of chloro-methyl acetate with compound 25 yielded the prodrug 27 (SCHEME 13).

Example 4

Methods for Assessing Amyloid Beta Peptide Modulation In Vitro and In Vivo of Representative Compounds Procedure for Determining the Aβ Peptide Inhibitory Activity of Representative Compounds in vitro A variety of cell lines normally produce and secrete various Aβ peptide alloforms into the media upon culture in supportive media. Examples of cell lines routinely used to assess the ability of a compound to inhibit formation specific Aβ peptide alloforms such as Aβ$_{42}$, upon treatment of the cells with various concentrations of the compound for approximately 16 h followed by determining the concentration of the various Aβ peptide alloforms in the media both with and without treatment with the compound [(e.g., HEK-293, N2a delta E9/Swe, SHSY5Y and primary cerebral cortical neuronal cultures from embryonic day 18 (E18) embryos from timed pregnant WT Sprague-Dawley rats) (Netzer, W I et al., Gleevec inhibits β-amyloid production but not Notch cleavage *Proc. Natl. Acad. Sci. U.S.A.* 2003; 100:12444-12449)].

Procedure for Determining the Aβ Peptide Inhibitory Activity of Representative Compounds in vivo A variety of animal models (e.g., male Hartley guinea pigs) including transgenic mouse models (e.g., Tg2576 or APP23) have been used to assess the ability of a compound to affect the levels of specific Aβ peptide alloforms upon treatment of the animal using various routes of administration and various concentrations of the compound for various lengths of time and comparing the levels of specific Aβ peptide alloforms such as Aβ$_{42}$ and/or the level of occupancy of a given organ, such as the brain, by pathological lesions associated with specific Aβ peptide alloforms (e.g., Aβ deposits and/or Aβ plaques) and comparing to those effects achieved on animals treated with vehicle alone [(Lanz T A, et al., Concentration-Dependent Modulation of Amyloid-β in Vivo and in Vitro Using the γ-Secretase Inhibitor, LY-450139 *J Pharmacol Exp Ther* 2006; 319: 924-933) and (Abramoswki D, et al., Dynamics of Aβ Turnover and Deposition in Different APP Transgenic Mouse Models Following Gamma-Secretase Inhibition *J Pharmacol Exp Ther* 2008; 327:411-424)].

Example 5

Synthesis of Novel GSM Compounds
Advanced Intermediates:

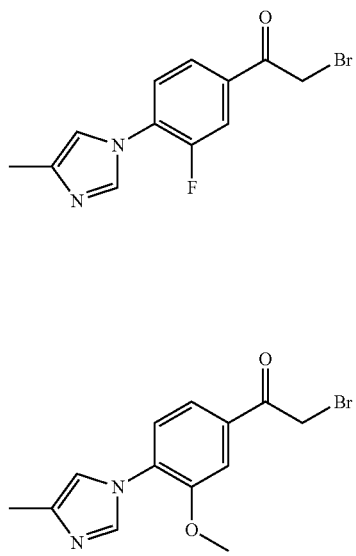

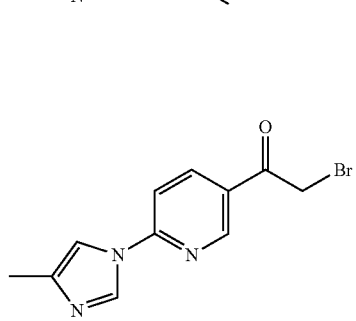

-continued

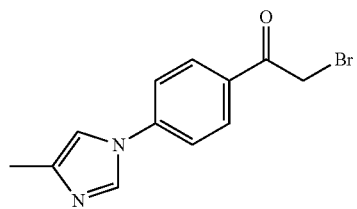

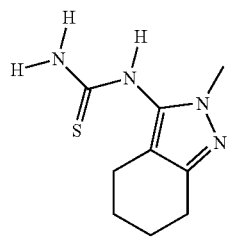

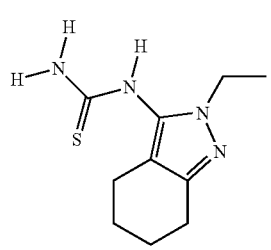

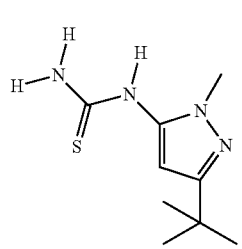

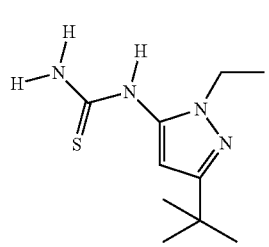

Preparation of α-Bromoketone Derivatives

A. Synthesis of α-bromoketone Derivative 1

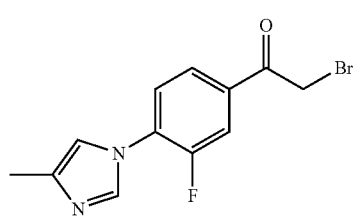

Scheme 1

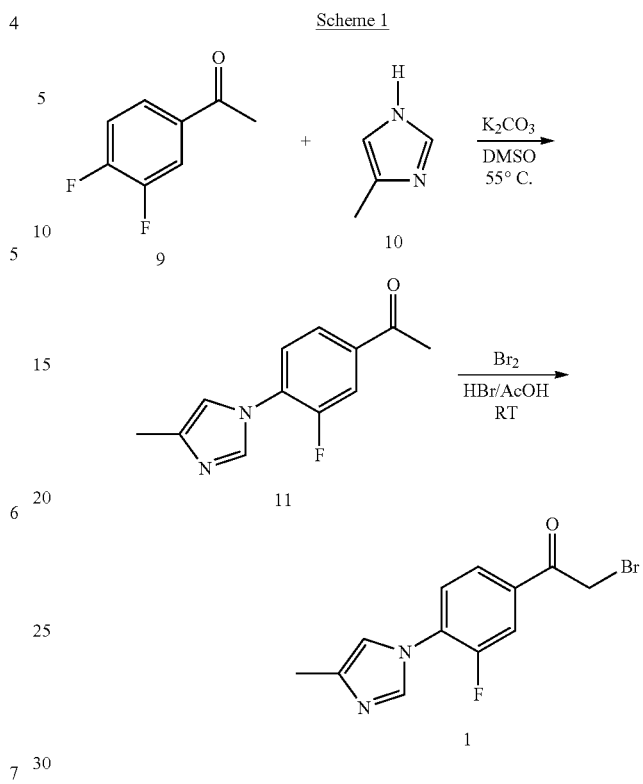

To a solution of 4-methylimidazole 10 (28.5 g, 347 mmole) in DMSO (200 ml), K$_2$CO$_3$ (132 g, 955 mmol) and 1-(3,4-difluoro-phenyl)-ethanone 9 (50.0 g, 320 mmole) were added. The reaction mixture was heated and stirred at 55° C. for 16 h. The reaction mixture was allowed to cool to room temperature and water (600 mL) was added. The reaction mixture was stirred for another 60 min. The precipitate was collected, washed with water (~2 L) and dried under vacuum overnight to yield the crude product. Recrystallization (Note) of the crude product afforded the desired product 11 (32.5 g, 59% yield). Note: A 30 g crude product was crystallized from water (2160 ml) and alcohol (240 mL) mixture and isolated 18.74 g of product. $^1$H, $^{13}$C NMR and LC/MS confirm the structure.

To a solution of compound 11 (37.5 g, 171.8 mmol) in HBr (30% in HOAc, 400 mL) was added bromine (27.5 g, 8.81 mL, 171.8 mmol) dropwise with stirring over a period of 60 min. The reaction mixture was stirred for another 40 min. and the reaction mixture was concentrated to remove most of the HBr and HOAc. The crude material was re-dissolved in methanol (300 mL) and then concentrated under vacuum in order to remove the rest of HBr and HOAc. The crude product was added water and the suspension was filtered, dried under vacuum overnight to give the desired product 1 (43.5 g, 67% yield).

B. Synthesis of α-bromoketone Derivative 2

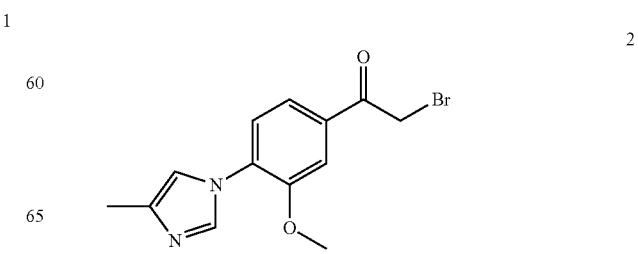

Scheme 2

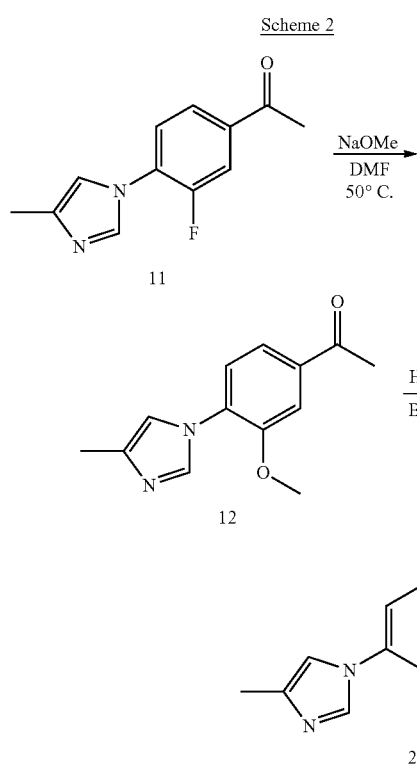

Procedure for the preparation of Compound 12: Compound 11 (12.0 g, 56.3 mmol) was dissolved in dry DMF (40 mL) and NaOMe (dry, 98%) (6.08 g, 112.6 mmol) was added in three equal portions over 10 minutes making sure the temperature did not rise above 20° C. by using a thermometer and inserting the flask into an ice bath. The reaction flask was then put into an oil bath at 50° C. and the reaction stirred for 35-40 min. The reaction was monitored by LC/MS and was removed from the oil bath when the starting material (40) had decreased to about 10% by U.V. 220 nm. During this time the reaction turned dark colored. Water (200 mL) was added slowly at first to quench the reaction. The mixture was then immediately extracted with EtOAc (2×200 mL). EtOAc layers were then combined and washed with water:brine 1:1 (200 mL). The EtOAc layers were then dried over MgSO$_4$, filtered and concentrated to a dark liquid. The resulting material was then purified by flash chromatography. 240 g Merck Silica gel pre-packed column. Gradient: 50-80% EtOAc/Hexanes over 5 min at 65 mL/min. Then 80-100% EtOAc/Hexanes over 20 min at 65 mL/min then hold at 100% EtOAc at 65 mL/min until compound fully eluded off of the column (10-20 min). Fractions were checked by TLC (100% EtOAc). Pure fractions were combined and concentrated to a pale yellow solid (1.8 g). Mixed fractions were combined separately and concentrated to a thick oil. Et$_2$O (15 mL) was immediately added to the oil and the flask quickly swirled to dissolve the oil. Crystals began forming within two minutes and allowed to crystallize over 18 h. The crystals were then collected on a filter and washed with Et$_2$O (2×5 mL) to yield the compound as off-white needles. Yield 1.7 g. Combined material totaled 3.5 g, yield 27%. Purity by LC/MS>98%.

Procedure for the preparation of Compound 2: Compound 22 (2.2 g, 9.56 mmol) was dissolved in DCM (30 mL) and 33% HBr/AcOH (5.0 mL, 28.68 mmol, 3 eq) was added. Br$_2$ (1.45 g, 9.08 mmol, 0.95 eq) was diluted with DCM (0.4 mL) and added drop wise to the stirring mixture over 40 min. Solvent was then removed on the rotary evaporator. The resulting mixture was then re-dissolved in DCM (20 mL) and removed on the rotary evaporator. This process was repeated two more times to help remove excess HBr and AcOH. The material was then suspended in Et$_2$O (20 mL), sonicated, triturated and Et$_2$O removed on the rotary evaporator. This process was repeated two more times until the compound appeared as a free-flowing pink solid. The material was then dried over 18 h under high vacuum. Yield 3.9 g, 105%. LC/MS purity 82%. Note: Main impurities: dibrominated compound (~10%).

Synthesis of α-bromoketone Derivative 3

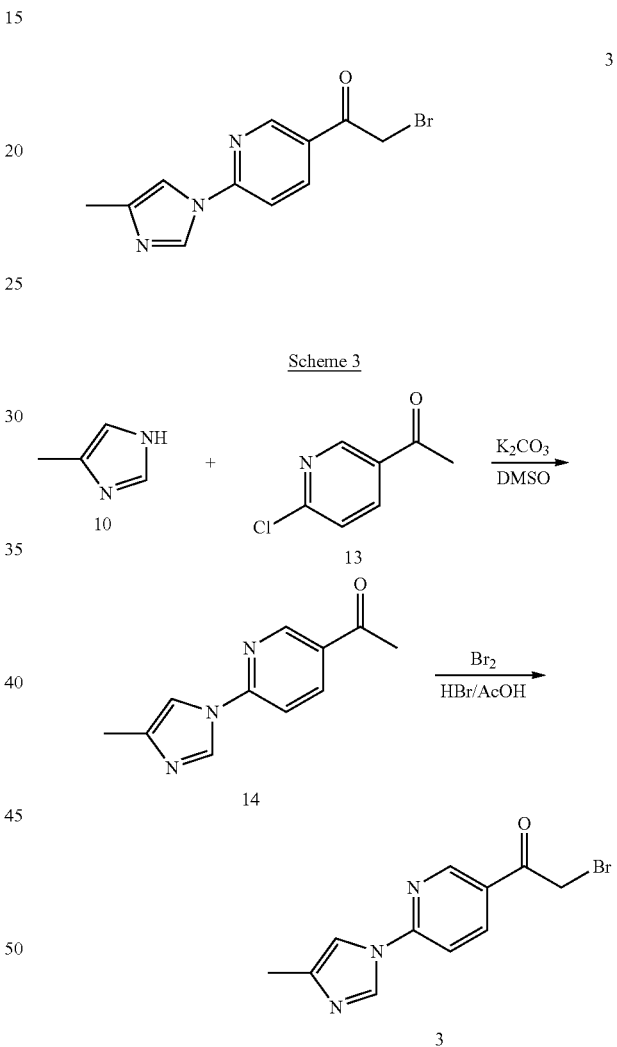

1-(6-chloro-pyridin-3-yl)-ethanone 13 (7.0 g, 45.2 mmol) and 4-methyliminazole 10 (11.1 g, 135.5 mmole) were combined in DMSO (35 mL), followed by addition of K$_2$CO$_3$. The mixture was heated at 110° C. for 22 h. The reaction mixture was then cooled to room temperature and poured into ice water (400 mL) with vigorous stirring for 15 min. The resulting precipitate was collected on a filter and washed with water. The resulting material was dried in vacuo to yield 14 as a tan solid (6.1 g, 67%). LC/MS: [m+1]+=202.2, $^1$H NMR (DMSO-d6) 300 MHz δ2.18 (3H, s), 2.63 (3H, s), 7.72 (1H, s), 7.87 (1H, d, J=9.0 Hz), 8.41 (1H, d, J=9.0 Hz), 8.51 (1H, s), 8.98 (1H, s).

Compound 14 (6.1 g, 30.3 mmole) was suspended in 30% HBr/AcOH (75 ml). Bromine (4.8 g, 30.3 mmole) was added dropwise over 1 h. The reaction mixture was stirred at room temperature for 2 h, poured into 600 mL of ice water and stirred for 15 min. The resulting precipitate was collected on a filter and washed with water. The compound was dried to yield 3 as a yellow solid (10.6 g, 80%). LC/MS: [M+1]$^+$= 282.1. $^1$H NMR (DMSO-d6) 300 MHz δ2.36 and 2.37 (3H, two s), 5.06 (2H, s), 8.16 (1H, d, J=9.0 Hz), 8.29 (1H, s), 8.69 (1H, d, J=9.0 Hz), 9.15 (1H, s), 9.93 (1H, s).

D. Synthesis of α-bromoketone Derivative 4

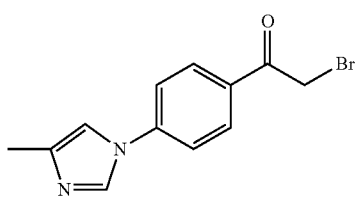

4

Synthetic Procedure: Similar Procedure as the Preparation of α-bromoketone 1.

Preparation of Thiourea Compounds

E. Synthesis of Thiourea 5

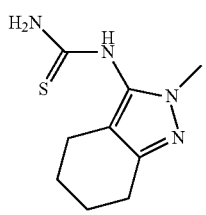

5

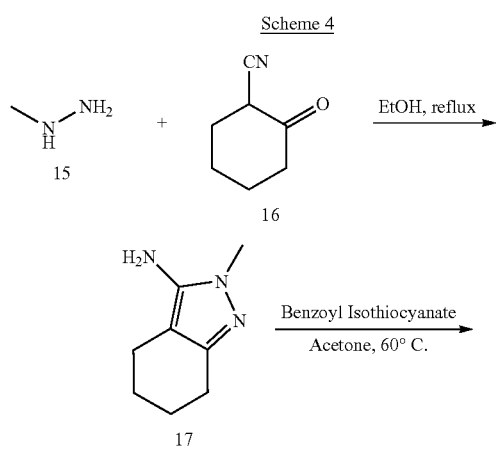

Scheme 4

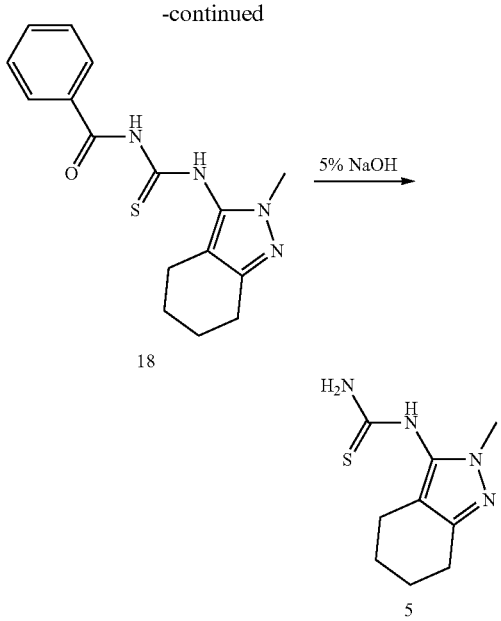

The coupling of methylhydrazine 15 with acetonitrile 16 in ethanol under reflux gave 17. Coupling of 17 with benzoyl isothiocyanate yield the benzoyl thiourea 18 in excellent yield. Alkaline hydrolysis of 18 yielded thiourea 5.

Preparation of 2-methyl-4,5,6,7-tetrahydro-2H-indazol-3-amine 17

A solution of 2-oxocyclohexanecarbonitrile 16 (10 g, 81.2 mmol) and methyl hydrazine 15 (3 equiv, 11.2 g) in 150 mL of absolute ethanol was refluxed for 20 hrs and was concentrated on rotavapor to dryness. The crude product was recrystallized from methanol to afford the desired product 17. (Reference for the preparation of compound 17: *J. Am. Chem. Soc.* 1959, 81, 2448-2452)

Preparation of N-(2-methyl-4,5,6,7-tetrahydro-2H-indazol-3-ylcarbamothioyl)benzamide 18

To a solution of compound 17 (5.0 g, 33.1 mmol) in 40 mL of acetone at 0° C. was added dropwise benzoyl isothiocynate (5.4 g, 33.1 mmol). The reaction mixture was gradually warmed up and stirred in an oil bath of 60° C. until TLC indicated there was no starting material remained. Concentration of the reaction mixture on rotavapor gave a yellow solid, which was further recrystallized in ethyl acetate to yield the desired product 18.

Preparation of 1-(2-methyl-4,5,6,7-tetrahydro-2H-indazol-3-yl)thiourea 5

A suspension of compound 18 (3 g, 9.5 mmol) in 30 mL of 5% NaOH aqueous solution was stirred in an oil bath of 90° C. for 8 hrs and cooled down to room temperature. Ice was added while stirring to the reaction mixture. The resulting suspension was filtered, and the cake was washed with cold water (10 mL×3) and further dried in vacuo to afford the desired product 5 as an off-white powder.

F. Synthesis of Thiourea 6

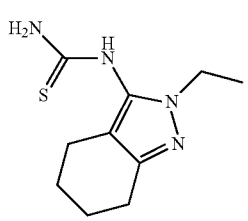

G. Synthesis of Thiourea 8

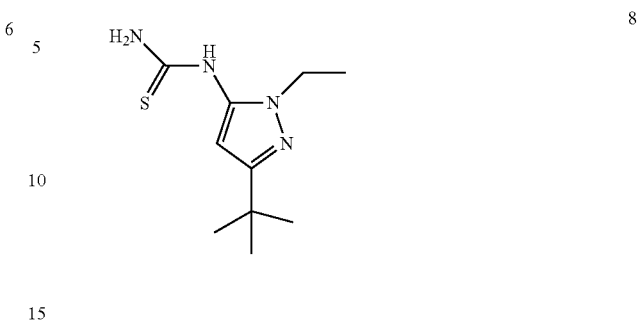

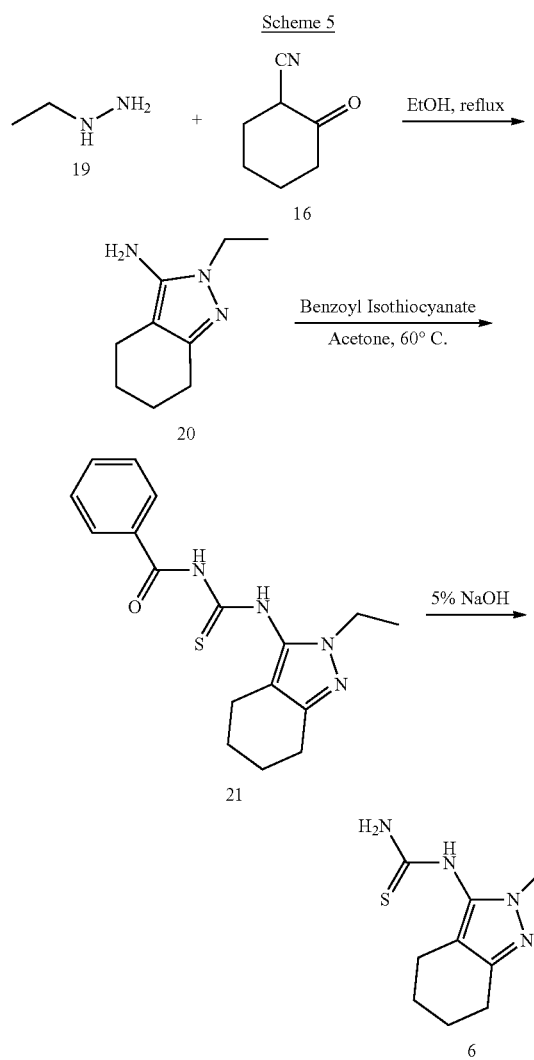

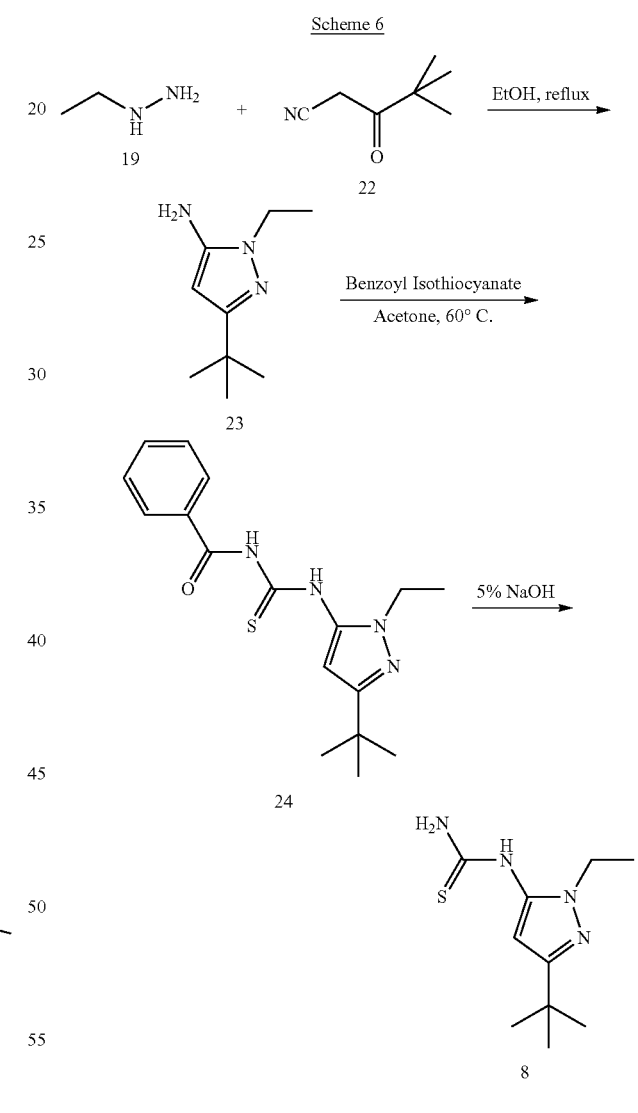

Synthetic Procedure: Similar Procedure as the Preparation of Thiourea 5.

The coupling of ethylhydrazine 19 with acetonitrile 16 in ethanol under reflux gave 20. Coupling of 20 with benzoyl isothiocyanate yield the benzoyl thiourea 21 in excellent yield. Alkaline hydrolysis of 21 yielded thiourea 6. Reaction of bromoketone 3 with thiourea 20 afforded 21.

The coupling of ethylhydrazine 19 with acetonitrile 22 in ethanol under reflux gave 23. Coupling of 23 with benzoyl isothiocyanate yield the benzoyl thiourea 24 in excellent yield. Alkaline hydrolysis of 24 yielded thiourea 8.

Preparation of
3-tert-butyl-1-ethyl-1H-pyrazol-5-amine 23

A solution of 4,4-dimethyl-3-oxopentanenitrile 22 (10 g, 79.9 mmol) and ethyl hydrazine 19 (3 equiv, 14.4 g) in 150 mL of absolute ethanol was refluxed for 24 hrs and was concentrated on rotavapor to dryness. The crude product was recrystallized from ethyl acetate to afford the desired product 23.

Preparation of N-(3-tert-butyl-1-ethyl-1H-pyrazol-5-ylcarbamothioyl)benzamide 24

To a solution of compound 23 (5.0 g, 29.9 mmol) in 40 mL of acetone at 0° C. was added dropwise benzoyl isothiocynate (4.88 g, 29.9 mmol). The reaction mixture was gradually warmed up and stirred in an oil bath of 60° C. until TLC indicated there was no starting material remained. Concentration of the reaction mixture on rotavapor gave a yellow solid, which was further triturated with ethyl ether to yield the desired product 24.

Preparation of 1-(3-tert-butyl-1-ethyl-1H-pyrazol-5-yl)thiourea 8

A suspension of compound 24 (5 g, 15.1 mmol) in 30 mL of 5% NaOH aqueous solution was stirred in an oil bath of 90° C. for 8 hrs and cooled down to room temperature. Ice was added while stirring to the reaction mixture. The resulting suspension was filtered, and the cake was washed with cold water (10 mL×3) and further dried in vacuo to afford the desired product 8 as an off-white powder.

Synthesis of Thiourea 7

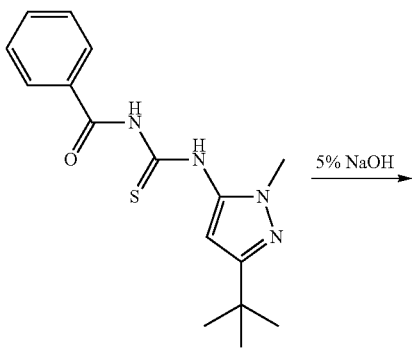

26

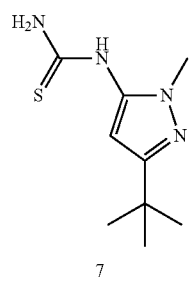

7

Synthetic Procedure: Similar Procedure as the Preparation of Thiourea 8.

Chemical Structures of Novel GSM Compounds:

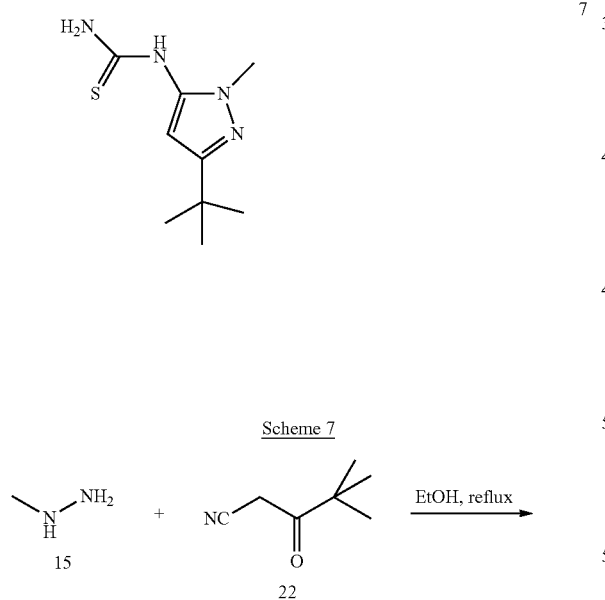

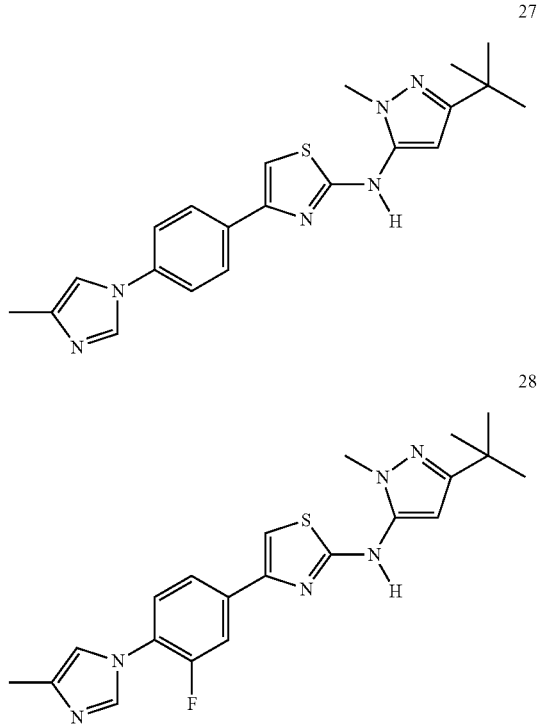

29
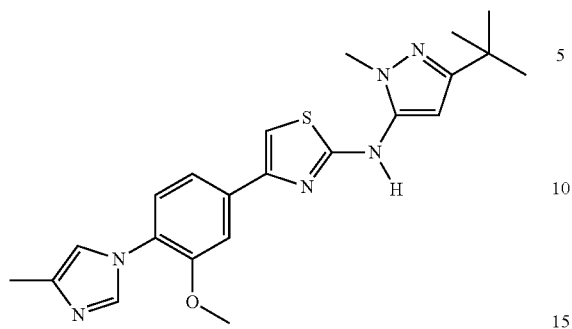
30
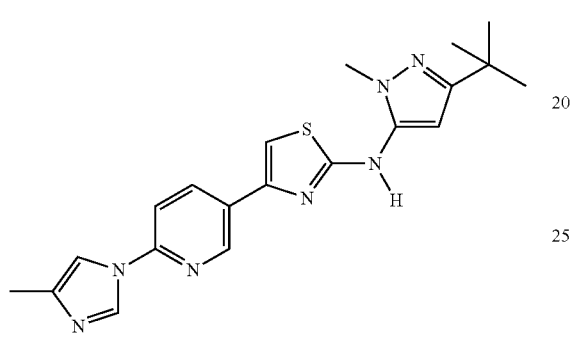
31
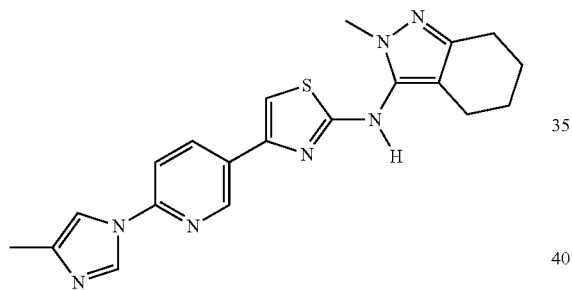
32
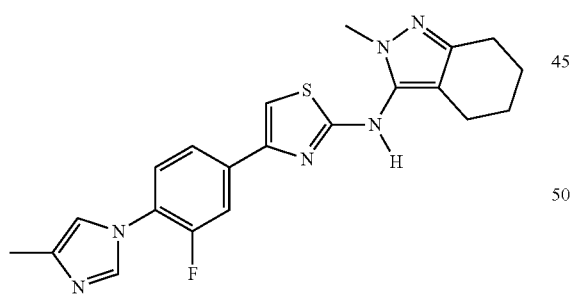
33
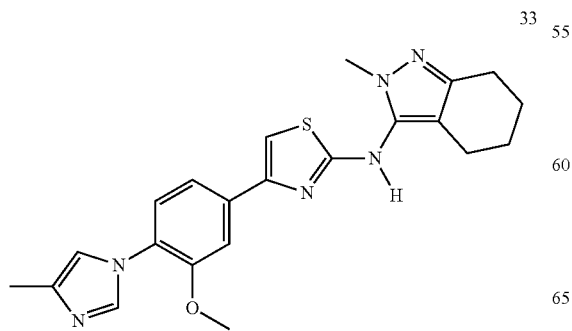
34
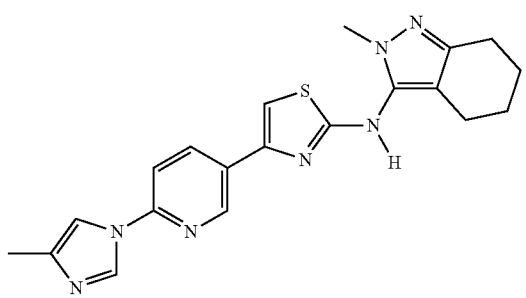
35
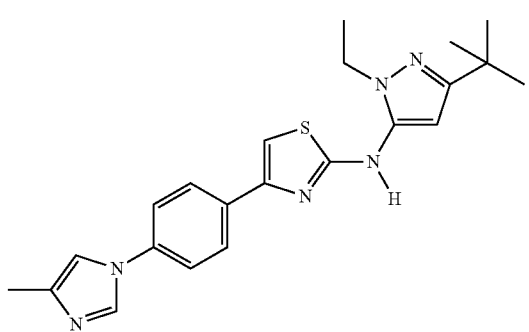
36
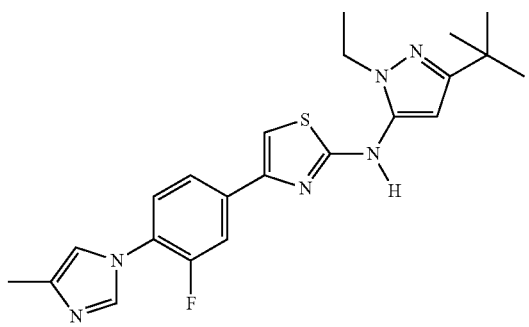
37
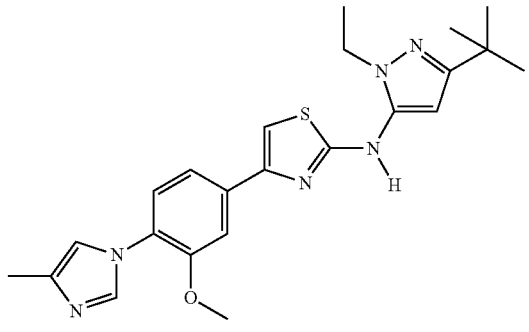

38

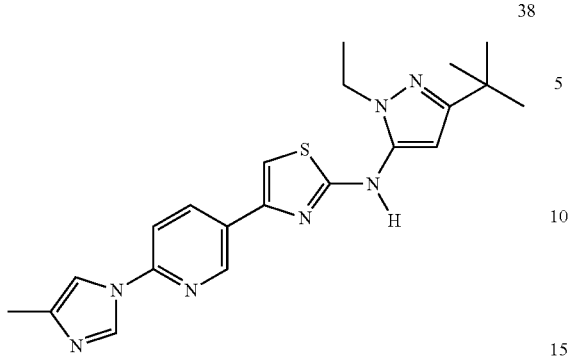

39

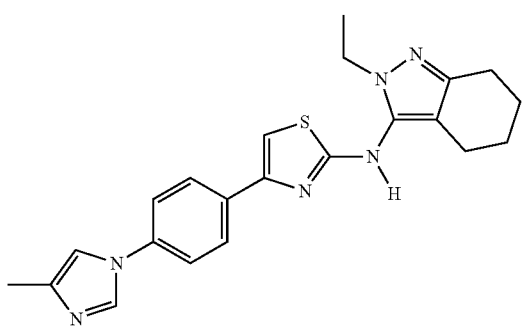

40

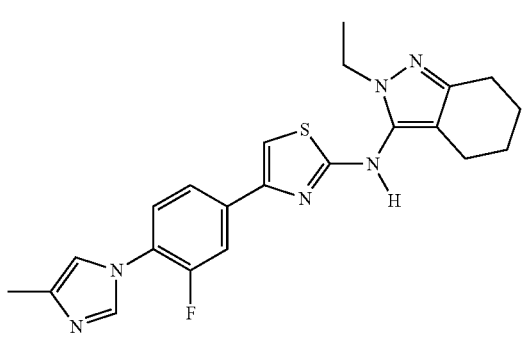

41

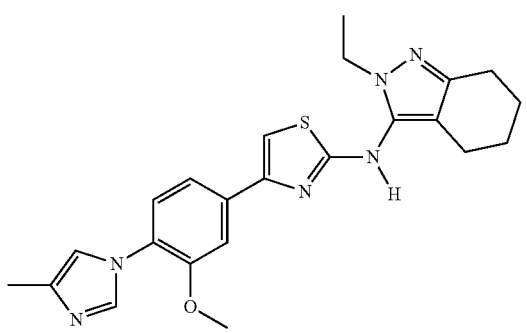

42

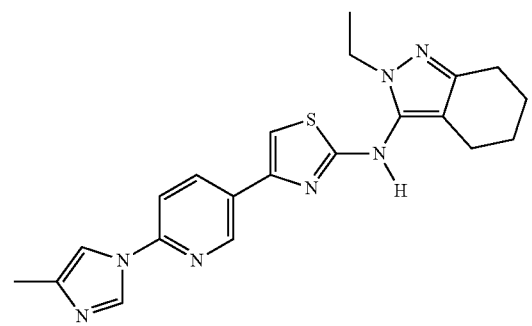

Preparation of Novel GSM Compounds:

Scheme 8

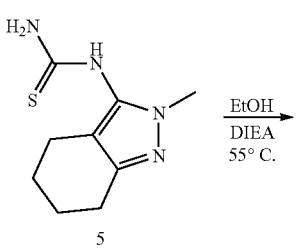

2

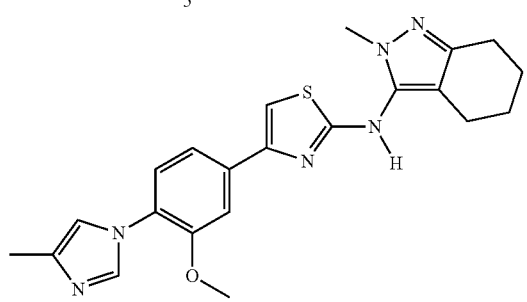

33

Preparation of Compound 33 (Scheme 8)

To a solution of compound 5 (500 mg, 2.4 mmol) in 8 mL of absolute ethanol was added compound 2 (737 mg, 2.4 mmol) followed by Hünig's base (4 equiv, 1.1 g) at room temperature. The reaction mixture was stirred in an oil bath of 55° C. until LCMS indicated there was a single peak product formed and no starting material remained. Removal of most of ethanol and DIEA gave the crude product that was purified by reverse-phased HPLC to yield the desired product 33.

Preparations of Compound 31, 32 and 34 (Scheme 9)
Synthetic Procedures: Similar Procedure as the Preparation of Compound 33.
Scheme 9
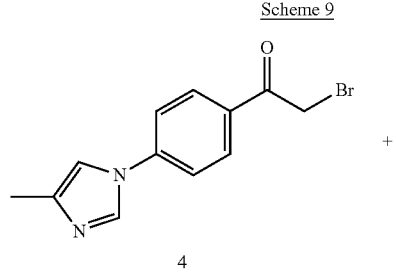
4
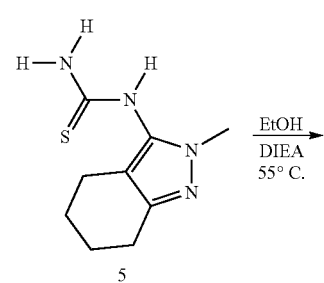
5
EtOH
DIEA
55° C.
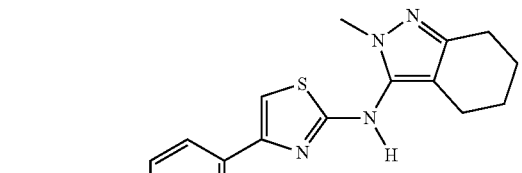
32
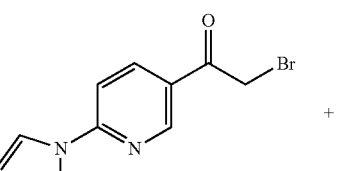
3
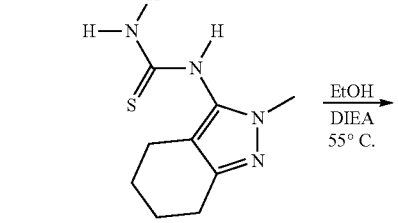
5
EtOH
DIEA
55° C.
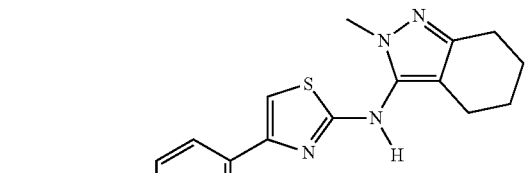
31
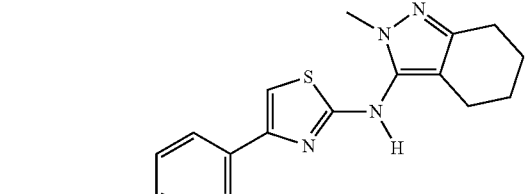
34
Preparations of Compound 39-42 (Scheme 10)
Synthetic Procedures: Similar Procedure as the Preparation of Compound 33.
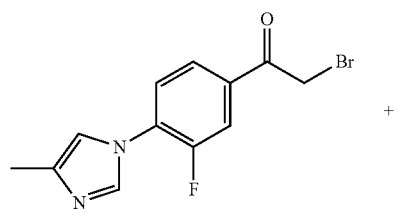
1
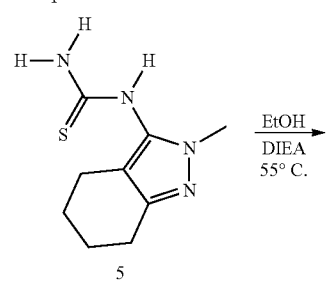
5
EtOH
DIEA
55° C.
Scheme 10
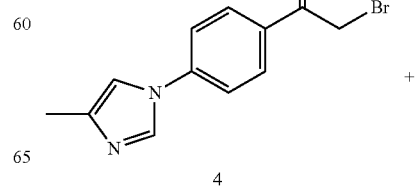
4

61
-continued
62
-continued
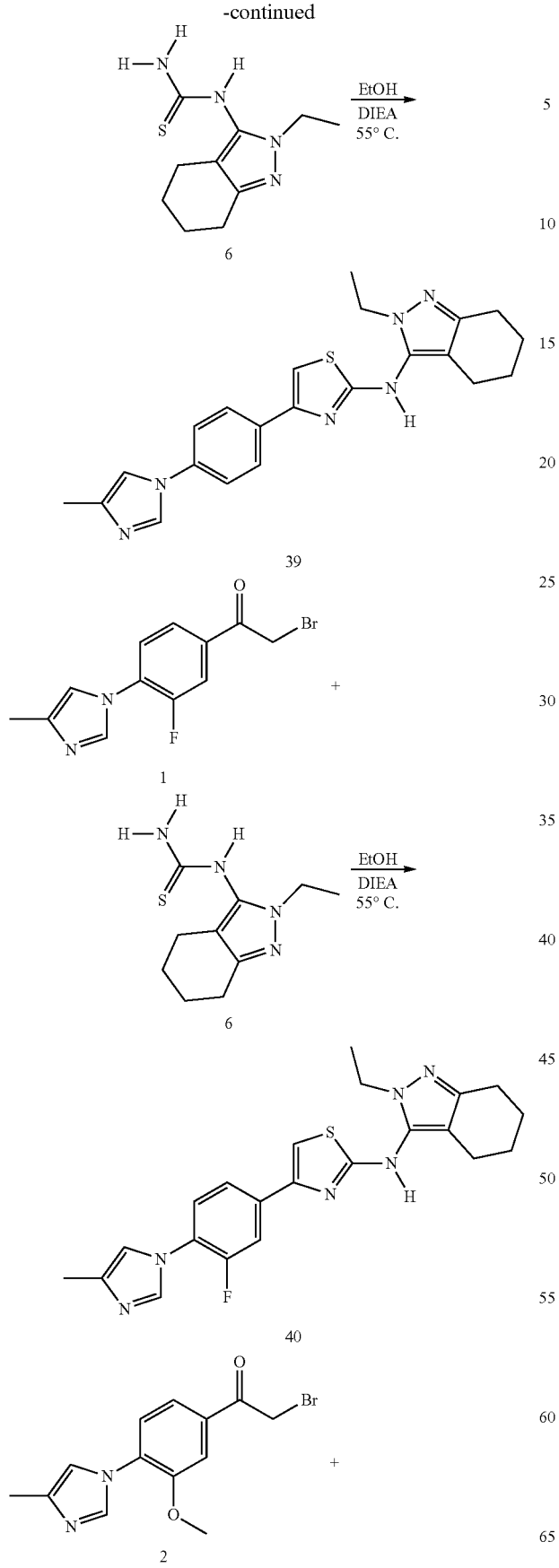
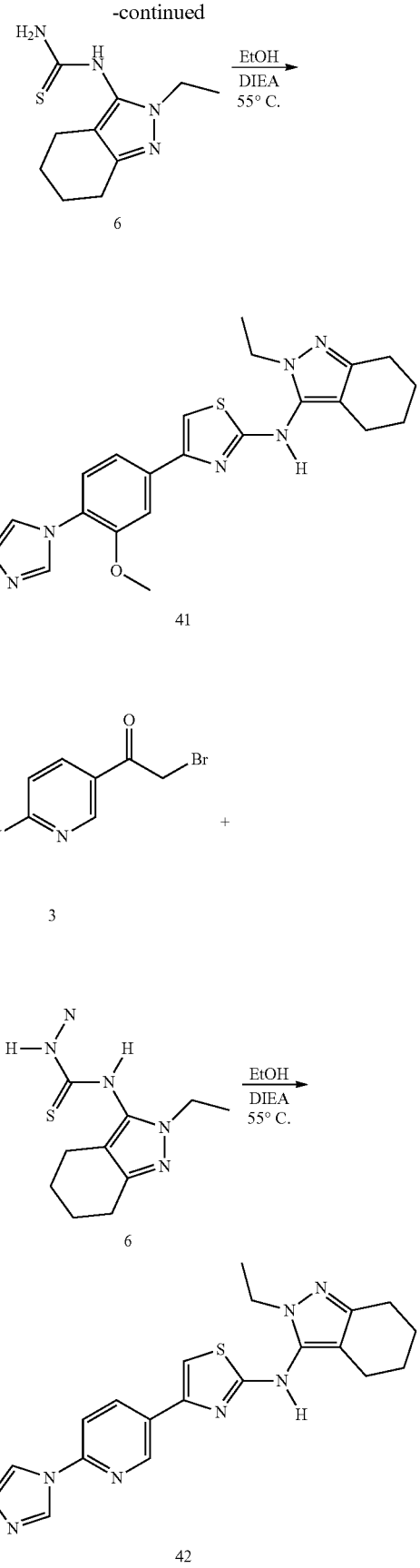

63

Scheme 11

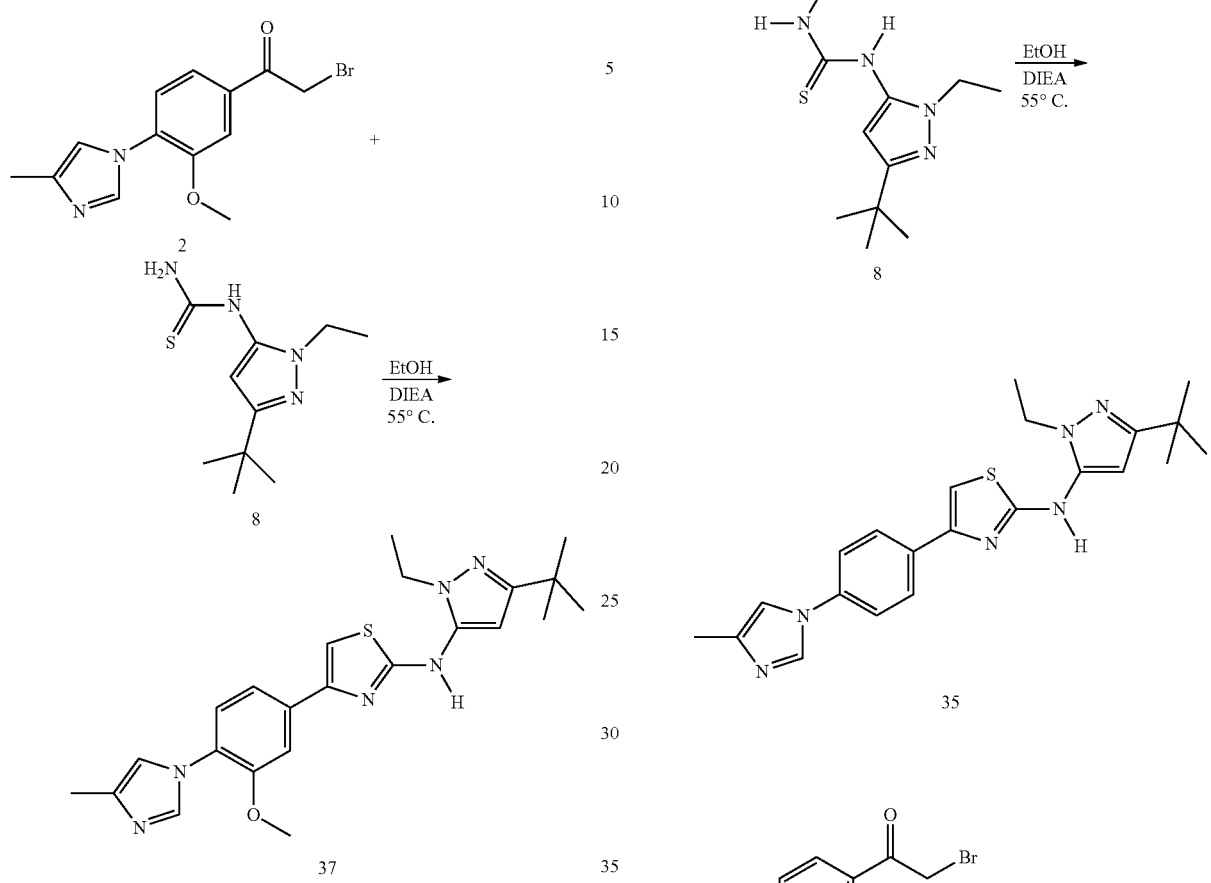

Preparation of Compound 37 (Scheme 11)

To a solution of compound 8 (500 mg, 2.4 mmol) in 10 mL of absolute ethanol was added compound 2 (737 mg, 2.4 mmol) followed by Hünig's base (4 equiv, 1.1 g) at room temperature. The reaction mixture was stirred in an oil bath of 55° C. until LCMS indicated there was a single peak product formed and no starting material remained. Removal of most of ethanol and DIEA gave the crude product that was purified by reverse-phased HPLC to yield the desired product 37.

Preparations of Compound 35, 36 and 38 (Scheme 12)

Synthetic Procedures: Similar Procedure as the Preparation of Compound 37.

Scheme 12

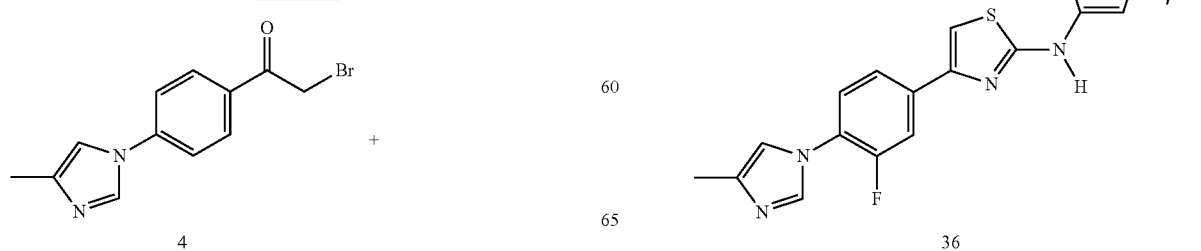

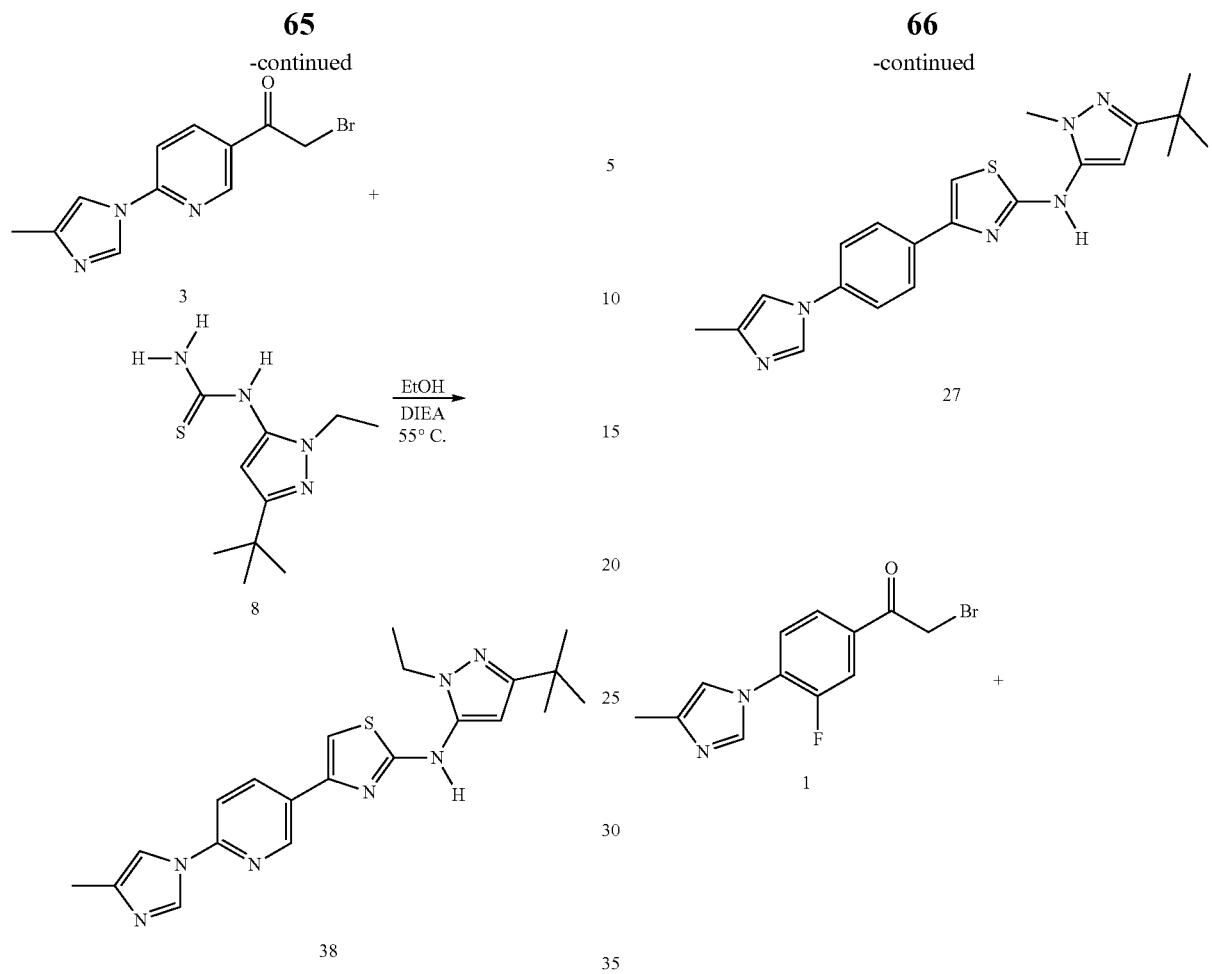
Preparations of Compound 27-30 (Scheme 13)
Synthetic Procedures: similar Procedure as the Preparation of Compound 37.
Scheme 13
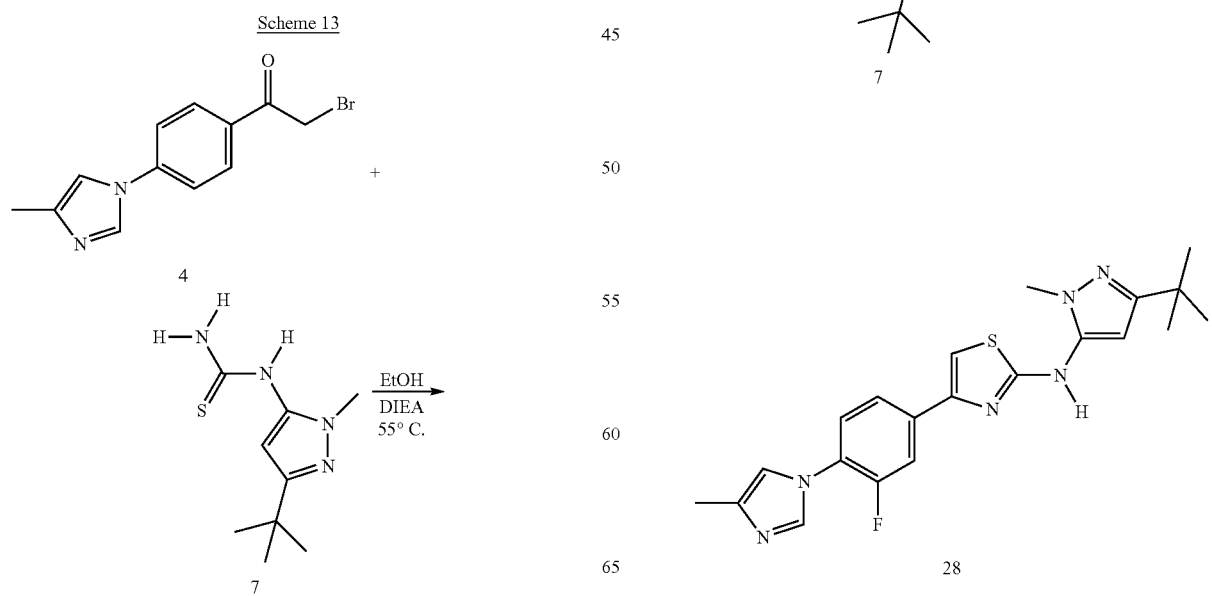

| 67 | 68 |
|---|---|
| 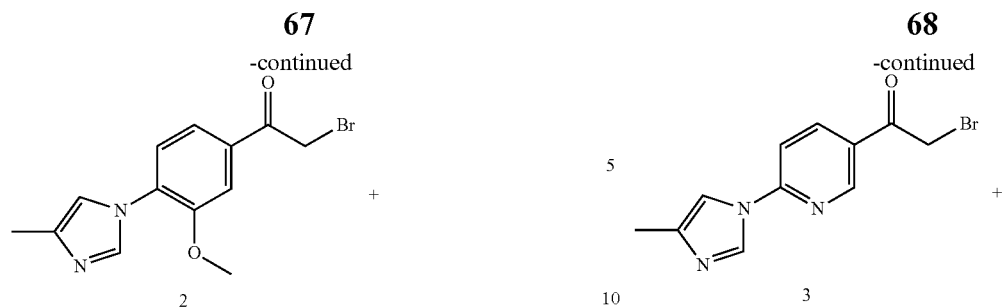 | 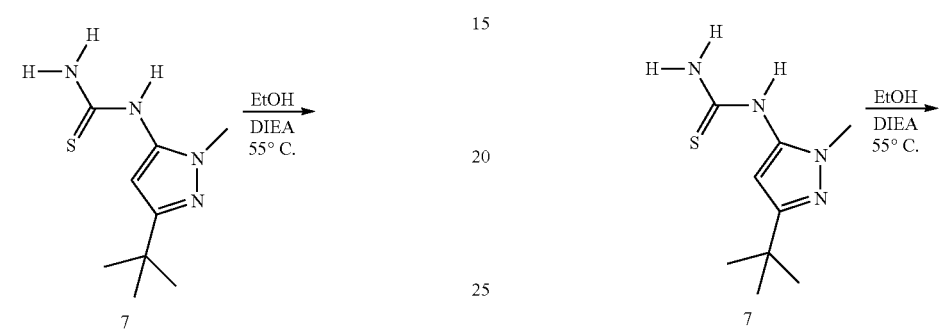 |
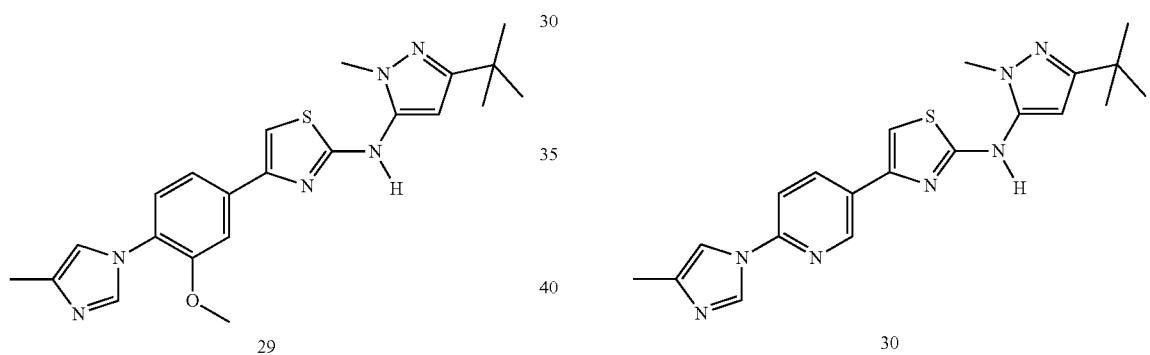
| Compound | Structure | IC50 for the inhibition of Aβ42 | EC50 for the potentiation of Aβ38 | Total Aβ | ClogP | Solubility (μM) pH6.6 | pH7.4 | Details of compound-Fit for each ring A | B | C | D |
|---|---|---|---|---|---|---|---|---|---|---|---|
| 27 | 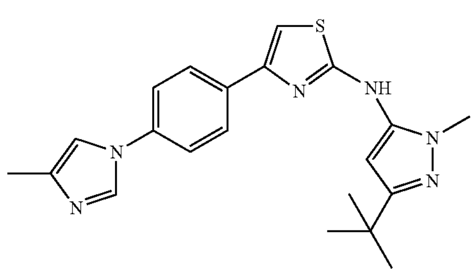 | c*** | | No Change | 4.62 | 2.4 | 2.3 | A | B(I) | C | |

-continued

| Compound | Structure | IC50 for the inhibition of Aβ42 | EC50 for the potentiation of Aβ38 | Total Aβ | ClogP | Solubility (μM) pH6.6 | pH7.4 | A | B | C | D |
|---|---|---|---|---|---|---|---|---|---|---|---|
| 28 | 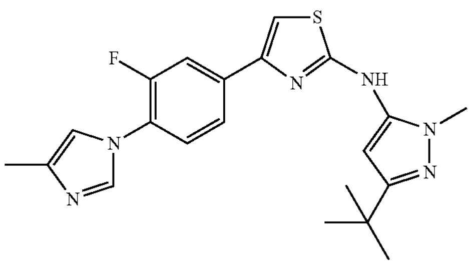 | b** | | | 4.64 | 3.0 | 3.1 | A | B(I) | C | |
| 29 | 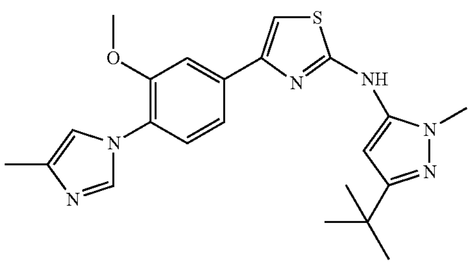 | b** | | | 4.38 | 14.8 | 11.6 | A | B(I) | C | |
| 30 | 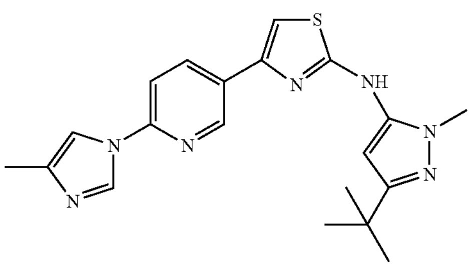 | d**** | | | 3.3 | 3.8 | 3.6 | A | B(II) | C | |
| 31 | 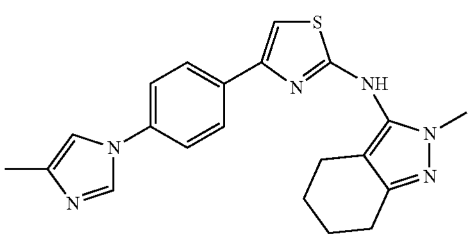 | b** | | No Change | 4.61 | 7.5 | 6.2 | A | B(I) | C | D(II) |
| 32 | 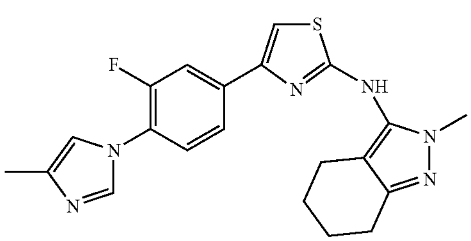 | b** | | | 4.64 | 4.8 | 4.2 | A | B(I) | C | D(II) |

-continued

| Compound | Structure | IC50 for the inhibition of Aβ42 | EC50 for the potentiation of Aβ38 | Total Aβ | ClogP | Solubility (μM) pH6.6 | pH7.4 | A | B | C | D |
|---|---|---|---|---|---|---|---|---|---|---|---|
| 33 | 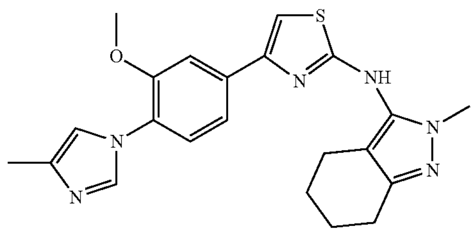 | b** | | | 4.38 | 18.4 | 12.1 | A | B(I) | C | D(II) |
| 34 | 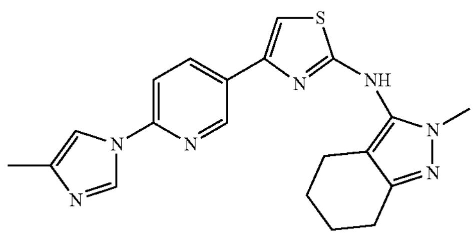 | d**** | | No Change | 3.3 | 12.0 | 11.8 | A | B(II) | C | D(II) |
| 35 | 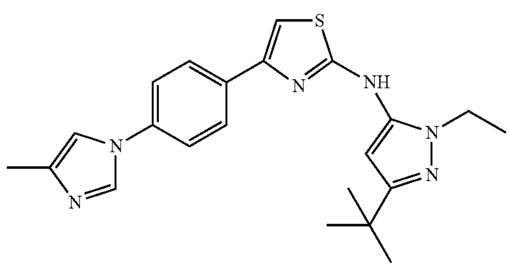 [SMILES: CCn1nc(C(C)(C)C)cc1Nc1nc(-c2ccc(-n3cnc(C)c3)cc2)cs1] | b** | | | 5.15 | 2.7 | 2.5 | A | B(I) | C | |
| 36 | 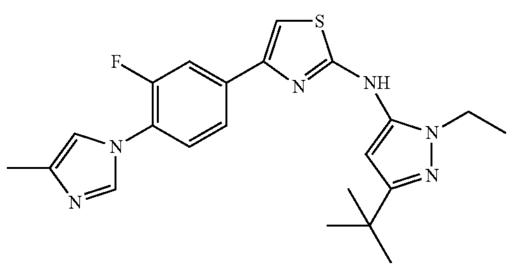 [SMILES: CCn1nc(C(C)(C)C)cc1Nc1nc(-c2ccc(-n3cnc(C)c3)c(F)c2)cs1] | a* | d**** | No Change | 5.17 | 1.8 | 2.1 | A | B(I) | C | |
| 37 | 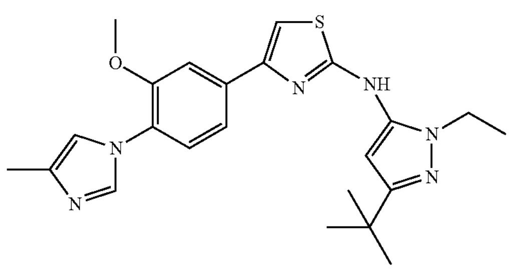 [SMILES: CCn1nc(C(C)(C)C)cc1Nc1nc(-c2ccc(-n3cnc(C)c3)c(OC)c2)cs1] | a* | b** | | 4.91 | 3.2 | 2.4 | A | B(I) | C | |

-continued

| Compound | Structure | IC50 for the inhibition of Aβ42 | EC50 for the potentiation of Aβ38 | Total Aβ | ClogP | Solubility (μM) pH6.6 | pH7.4 | A | Details of compound-Fit for each ring B | C | D |
|---|---|---|---|---|---|---|---|---|---|---|---|
| 38 | 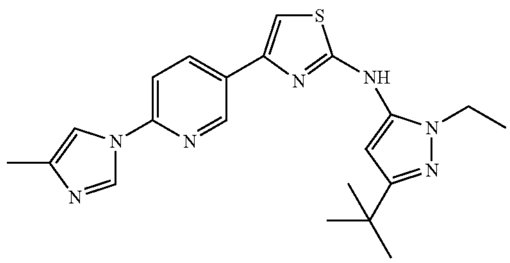 [SMILES: CCn1nc(C(C)(C)C)cc1Nc1nc(-c2ccc(-n3cnc(C)c3)nc2)cs1] | c*** | | | 3.83 | 3.5 | 3.7 | A | B(II) | C | |
| 39 | 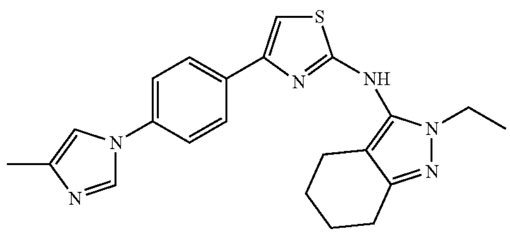 [SMILES: CCn1nc2c(c1Nc1nc(-c3ccc(-n4cnc(C)c4)cc3)cs1)CCCC2] | d**** | | | 5.15 | 2.3 | 2.6 | A | B(I) | C | |
| 40 | 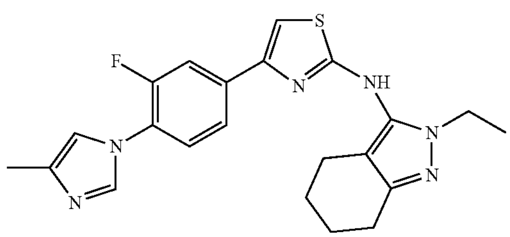 [SMILES: CCn1nc2c(c1Nc1nc(-c3ccc(-n4cnc(C)c4)c(F)c3)cs1)CCCC2] | b** | | | 5.17 | 2.8 | 2.6 | A | B(I) | C | |
| 41 | 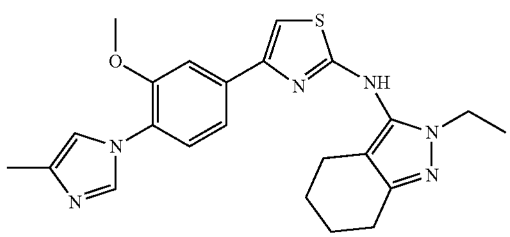 [SMILES: CCn1nc2c(c1Nc1nc(-c3ccc(-n4cnc(C)c4)c(OC)c3)cs1)CCCC2] | a* | d**** | | 4.91 | 7.9 | 6.4 | A | B(I) | C | |
| 42 | 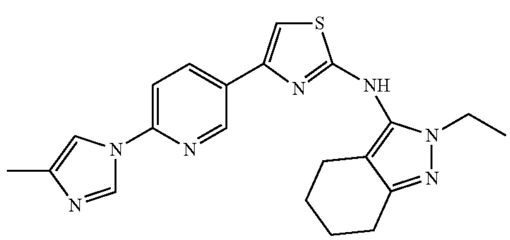 [SMILES: CCn1nc2c(c1Nc1nc(-c3ccc(-n4cnc(C)c4)nc3)cs1)CCCC2] | d**** | | | 3.83 | 5.5 | 6.3 | A | B(II) | C | |

-continued

| Compound | Structure | IC50 for the inhibition of Aβ42 | EC50 for the potentiation of Aβ38 | Total ClogP | Solubility (μM) pH6.6 pH7.4 | Details of compound-Fit for each ring A B C D |
|---|---|---|---|---|---|---|
| 43 | 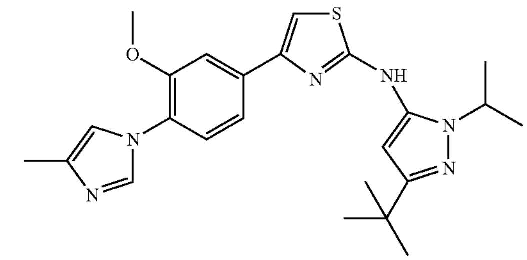 [SMILES: COc1cc(-c2csc(Nc3cc(C(C)(C)C)nn3C(C)C)n2)ccc1-n1cnc(C)c1] | b** | | 5.26 | | A  B(I)  C |
| 45 | 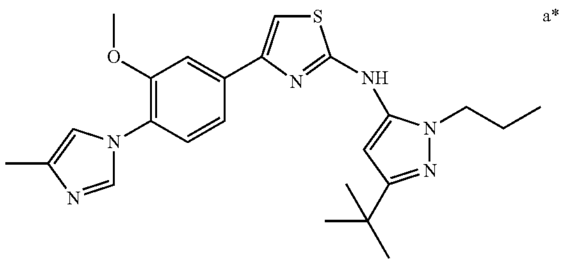 | a* | | 5.45 | | A  B(I)  C |
| 46 | 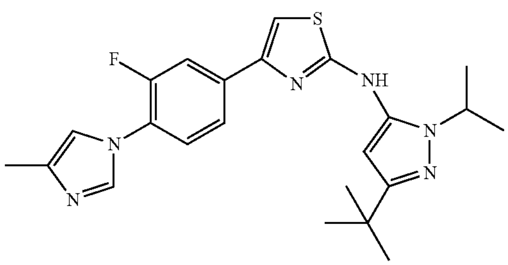 [SMILES: Cc1cn(-c2ccc(-c3csc(Nc4cc(C(C)(C)C)nn4C(C)C)n3)cc2F)cn1] | a* | | 5.52 | | A  B(I)  C |
| 48 | 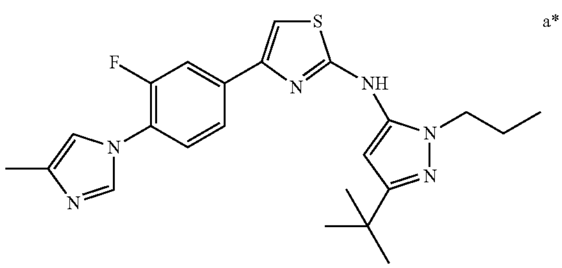 | a* | | 5.7 | | A  B(I)  C |
| 49 | | a* | | 4.25 | | A  B(III)  C | a* $IC_{50}$ for the inhibition of $A\beta_{42}$ or $EC_{50}$ for the potentiation of $A\beta_{38}$ <100 nM
b** $IC_{50}$ for the inhibition of $A\beta_{42}$ or $EC_{50}$ for the potentiation of $A\beta_{38}$ >100 nM and <250 nM
c*** $IC_{50}$ for the inhibition of $A\beta_{42}$ or $EC_{50}$ for the potentiation of $A\beta_{38}$ >250 nM and <500 nM
d**** $IC_{50}$ for the inhibition of $A\beta_{42}$ or $EC_{50}$ for the potentiation of $A\beta_{38}$ >500 nM

Example 6
New Compounds:
Synthesis of Compound 43, 45, 46 and 48
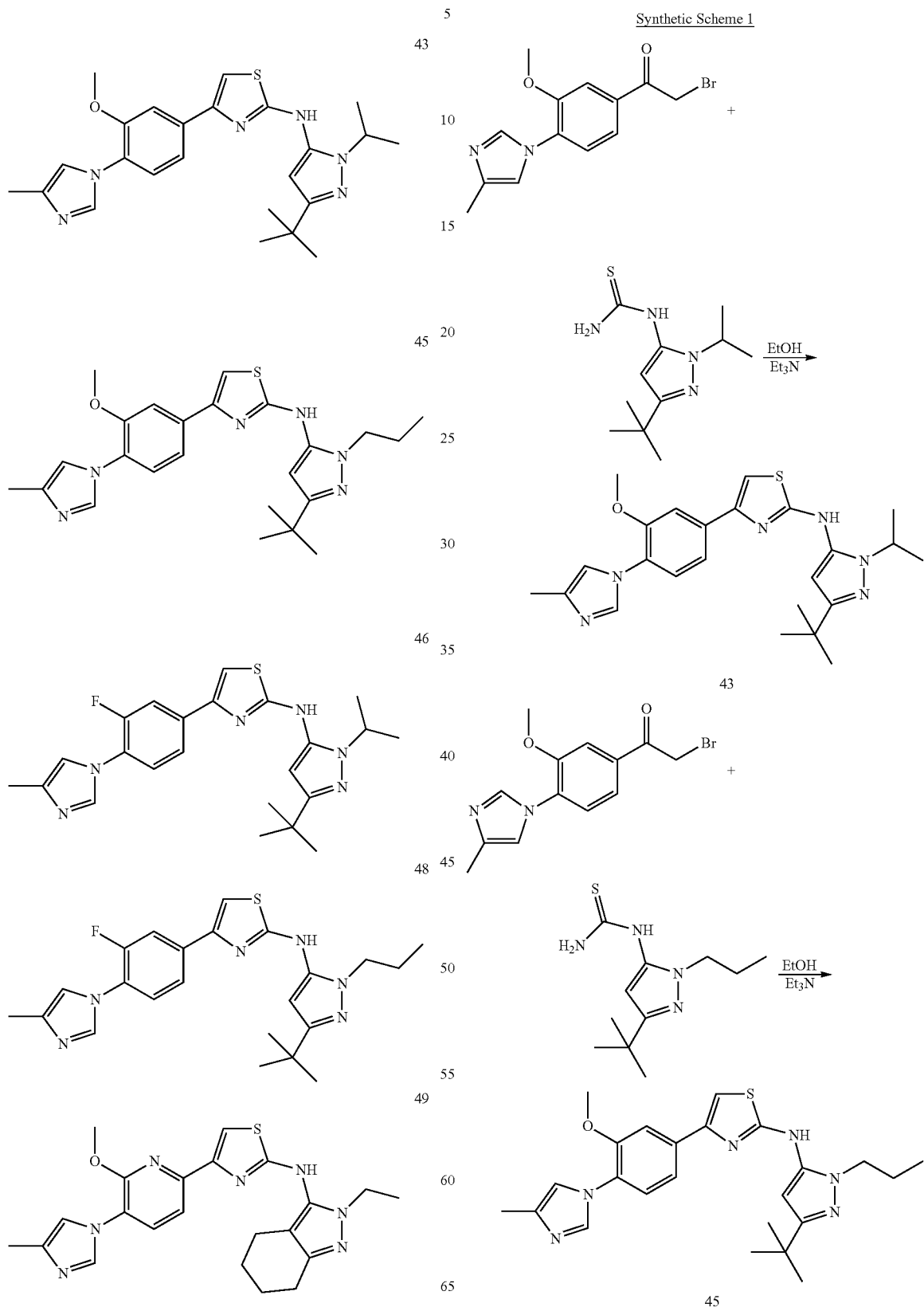

-continued
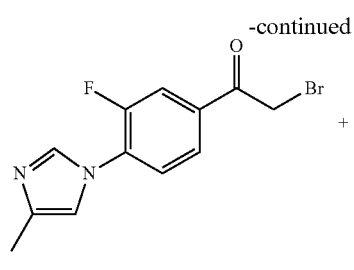
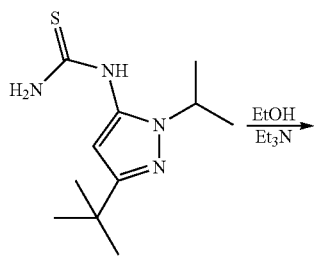
46
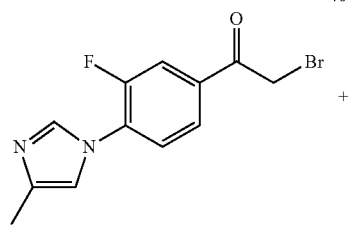
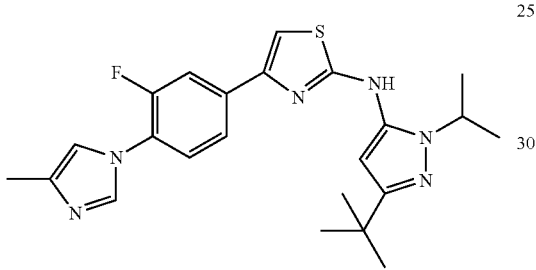
48
Synthesis of Thiourea Intermediates
Synthetic Scheme 2
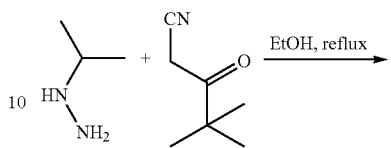
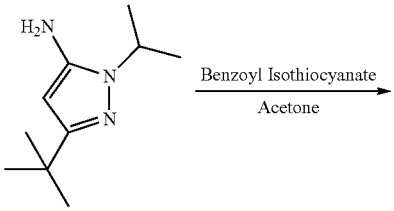
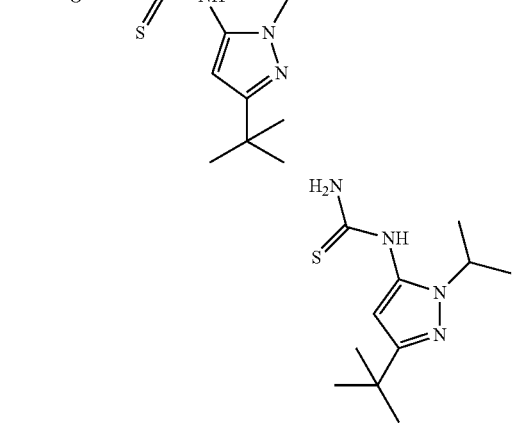
Synthetic Scheme 3
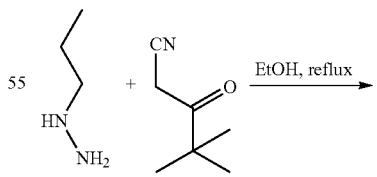
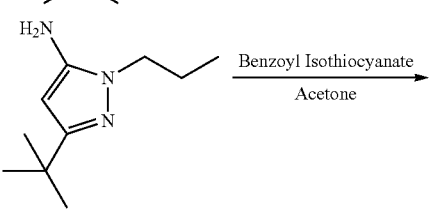

81
-continued
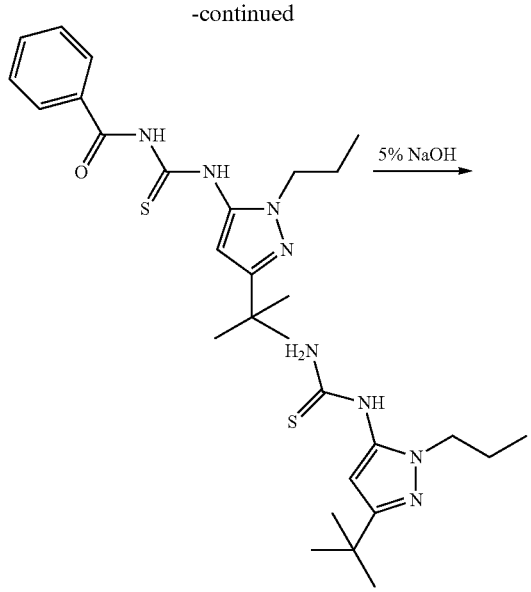
82
-continued
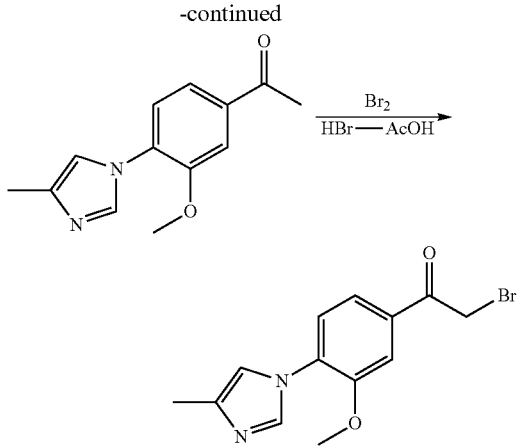
Synthesis of 49
Synthesis of Bromoketone Intermediates
Synthetic Scheme 4
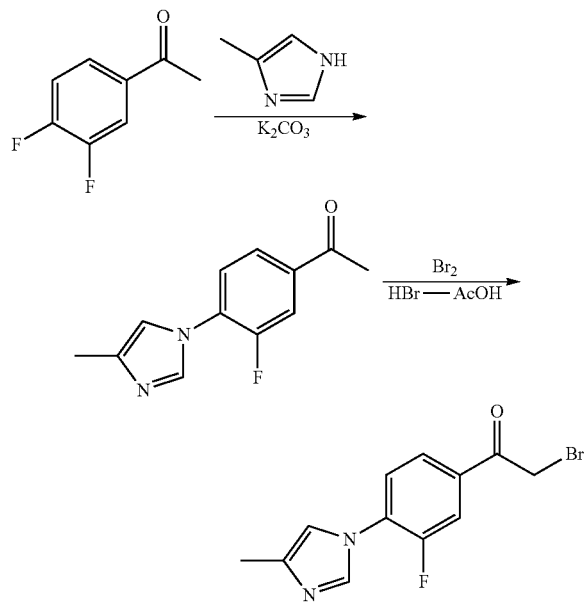
Synthetic scheme 5
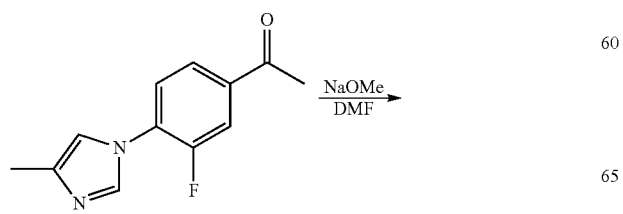
Synthetic Scheme 6
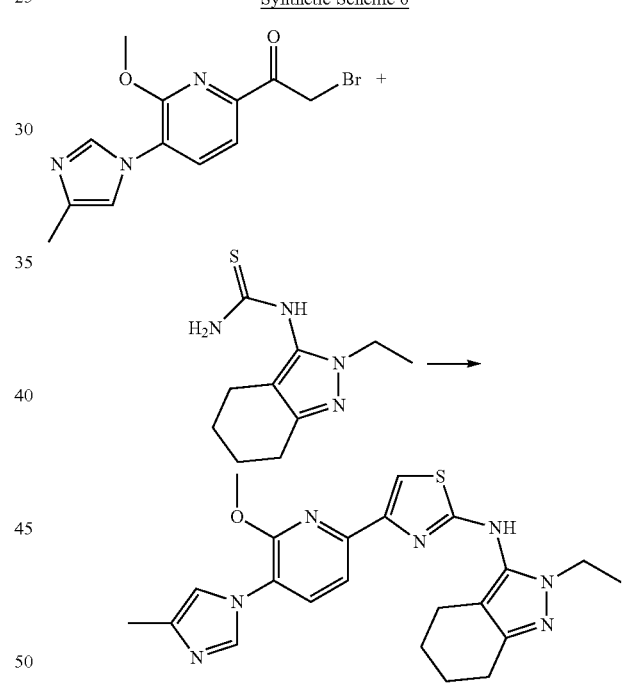
Synthesis of the Bromoketone Derivative
Synthetic Scheme 7
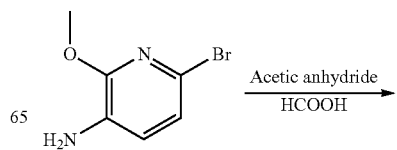

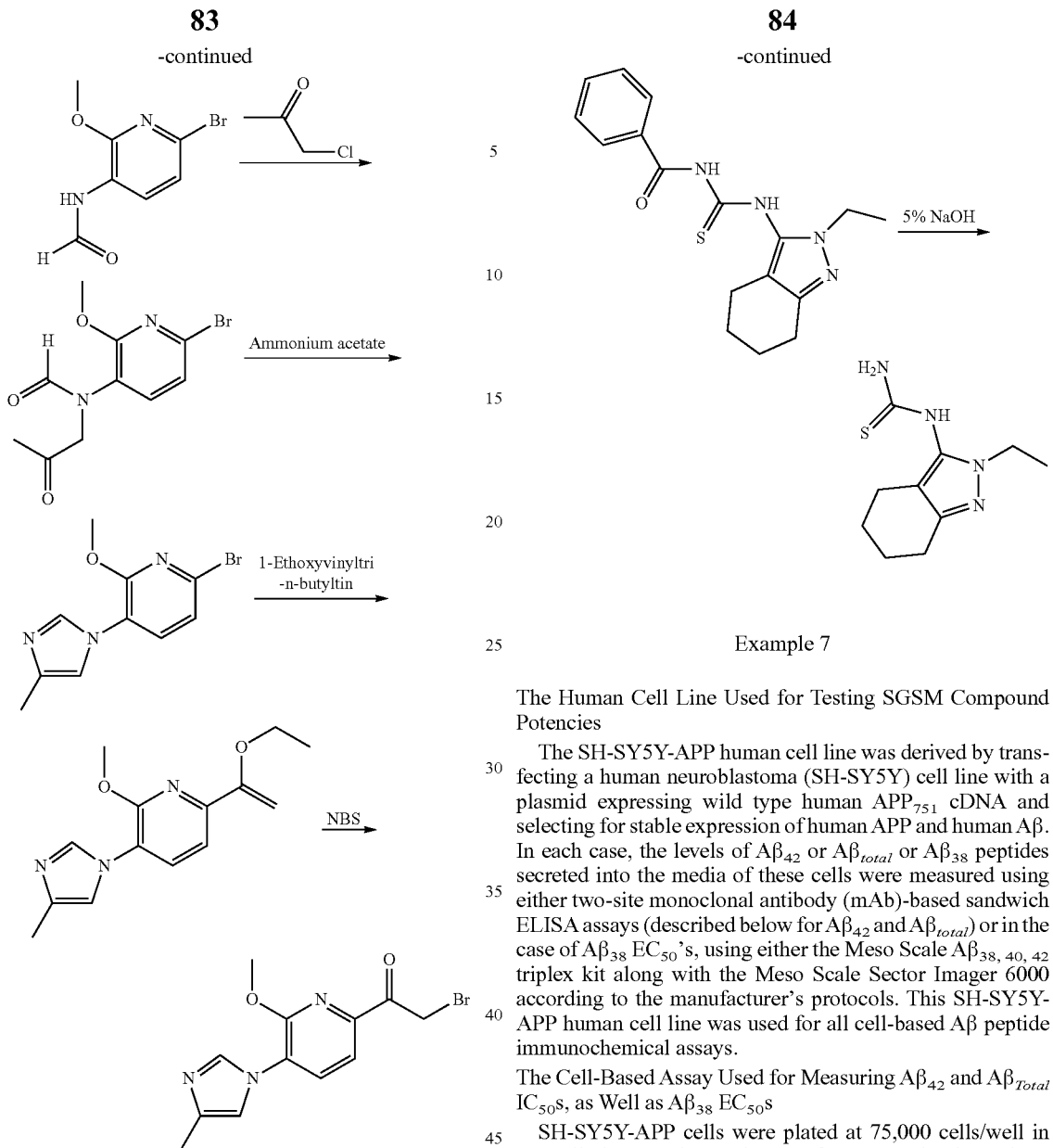

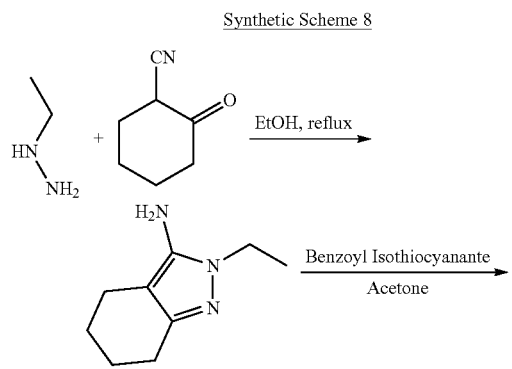

Synthesis of the Thiourea Derivative

Synthetic Scheme 8

Example 7

The Human Cell Line Used for Testing SGSM Compound Potencies

The SH-SY5Y-APP human cell line was derived by transfecting a human neuroblastoma (SH-SY5Y) cell line with a plasmid expressing wild type human $APP_{751}$ cDNA and selecting for stable expression of human APP and human Aβ. In each case, the levels of $A\beta_{42}$ or $A\beta_{total}$ or $A\beta_{38}$ peptides secreted into the media of these cells were measured using either two-site monoclonal antibody (mAb)-based sandwich ELISA assays (described below for $A\beta_{42}$ and $A\beta_{total}$) or in the case of $A\beta_{38}$ $EC_{50}$'s, using either the Meso Scale $A\beta_{38, 40, 42}$ triplex kit along with the Meso Scale Sector Imager 6000 according to the manufacturer's protocols. This SH-SY5Y-APP human cell line was used for all cell-based Aβ peptide immunochemical assays.

The Cell-Based Assay Used for Measuring $A\beta_{42}$ and $A\beta_{Total}$ $IC_{50}$s, as Well as $A\beta_{38}$ $EC_{50}$s SH-SY5Y-APP cells were plated at 75,000 cells/well in 96-well tissue culture plates. After 16-18 h, the culture medium was replaced with fresh medium containing either compound or vehicle. Replicates of 3 wells per test concentration were used, with 10 concentrations at ½ log step intervals. Vehicle (0.12% DMSO) is included as a control.

The Sandwich ELISA Assay for Measuring Inhibition of $A\beta_{42}$ and Determination of $A\beta_{42}$ $IC_{50}$ Inhibition Values Materials:

Microfluor-2 White Flat bottom 96-well microplates

Solutions:
 1× Phosphate Buffered Saline (PBS) pH 7.4
 1× Tris Buffered Saline (TBS) pH 8.0
 1% Bovine Serum Albumin (BSA)/TBS
 CSPD-Sapphire II Luminescence Substrate Reagents:

An Anti-$A\beta_{35-42}$ coating monoclonal antibody which is specific for the $A\beta_{42}$ peptide, stored in 60 μl aliquots at −80° C. (thaw once and discard after use).

$A\beta_{1-42}$ Peptide (Bachem) 0.01 mg/ml stock solution dissolved in hexafluoroisopropanol (HFIP)[1], stored at −20° C.

An Anti-Aβ$_{1-12}$ alkaline phosphatase-conjugated monoclonal antibody, stored at 4° C.

Procedure:

Anti-Aβ$_{35-42}$ monoclonal antibody was diluted 1/300 in 1×TBS. After vortexing, pipette 100 μl of antibody into each well of microplate. The antibody covered the entire bottom of each well. Each microplate was covered with a plate sealer and placed at 4° C. for 19 h.

Microplates were removed from the cold room, the coating monoclonal antibody were aspirated off from all wells. Each well was rinsed once with 200 μl TBS². The wells were blocked by pipetting 200 μl of 1% BSA/TBS blocking solution per well and the plates incubated at room temperature for 60 minutes on a laboratory benchtop.

Stock solution of Aβ$_{1-42}$ peptide was diluted 1/1000 by adding 5 μl of Aβ$_{42}$ to 4.995 ml of media to achieve a 10 ng/ml stock solution (500 pg/50 μl) solution.

The Aβ$_{1-42}$ standard curve was prepared. 0.5 ml of media was added to wells #2-#12 in deep well dish and 1 ml of the 500 pg/50 μl solution of Aβ$_{42}$ to well #1. Serially diluted 2-fold across plate for 10 places (the 12$^{th}$ well will serve as background with no Aβ$_{1-42}$ peptide) by pipetting 0.5 ml of solution mixing five times from well to well starting at well #1 to well #11.

Sample addition to plates: Directly following the 60 min block step, blocking buffer was aspirated off and 50 μl of sample was pipetted to each well and then standard curve samples (50 μl) were added in duplicate to top 2 rows.

The plates were incubated at room temperature for 2 h.

Each plate was washed three times. Each wash was 200 μl using 1×PBS/0.1% Tween-20 per well.

Anti-Aβ$_{1-12}$ mAb-alkaline phosphatase conjugate was diluted 1/10,000 in 1% BSA/TBS/0.1% Tween-20 and vortexed. 50 μl was pipetted into each well of the microplate.

Incubated plates at room temperature for 2 h. Afterwards plates were washed 6 times with 200 μl of 1×PBS/0.1% Tween-20 per well.

To all plates, 50 μl of CDP-Star (Sapphire) luminescence substrate (brought to room temperature prior to use) was added to each well and incubated for 15 min at room temperature in the dark. The timer was started after finishing adding the substrate to the first plate of the group. This step was done with a group of 5 plates or less.

Each microplate was read in a Glow Runner luminometer³.

The Sandwich ELISA ASSAY for Measuring Inhibition of Total Aβ Peptides and Determination of Aβ$_{total}$ Peptides IC$_{50}$ Inhibition Values Materials:
Microfluor-2 White Flat bottom 96-well microplates Solutions:
1×PBS pH 7.4
1×TBS pH 8.0
1% BSA/TBS
CSPD-Sapphire II Luminescence Substrate Reagents:
Anti-Aβ$_{1-12}$ coat antibody (3.4 mg/ml)
Aβ$_{1-40}$ Peptide (Bachem) 0.01 mg/ml
Signet—Monoclonal, Human Amyloid Beta Protein, Clone 4G8, Biotinylated
Rockland—Alkaline Phosphatase Conjugated Streptavidin Procedure:
Anti-Aβ$_{1-12}$ monoclonal antibody was diluted 1/100 in 1×TBS. Vortex. 100 μl was pipetted into each well of a microplate. The coating monoclonal antibody covered the entire bottom of each well. Each microplate was covered with a plate sealer and placed in the refrigerator overnight.

Microplates were removed from the refrigerator and each well was rinsed with 200 μl TBS. The wells were blocked by pipetting 200 μl 1% BSA/TBS per well of each microplate. The microplates were incubated at room temperature for 60 minutes.

Prepared Aβ$_{1-40}$ Standard Curve. The Aβ$_{1-40}$ peptide was stored at a stock concentration of 0.01 mg/ml. The stock solution was diluted to 1/500 in complete cell culture medium by adding 10 μl of peptide stock to 4.990 ml of media to produce a stock of 1000 pg/50 μl, then serially diluted the stock across the plate 2-fold with the last place containing no peptide sample in the media. The final standard curve of the peptide is 1000 pg, 500, pg 250 pg, 125 pg, 62.5 pg, 31.3 pg, 15.6 pg, 7.8 pg, 3.9 pg, 1.95 pg, 0.98 pg and 0 pg.

50 μl of sample was pipetted at the appropriate dilution into designated wells of the microplates. The microplates were incubated at room temperature for 2 hrs.

Each microplate was washed three times. Each wash was 200 μl 1×PBS/0.1% Tween-20 per well.

The biotinylated monoclonal antibody (anti-human Amyloid Beta Protein, Clone 4G8) was diluted 1/5000 in 1% BSA/TBS/0.1% Tween-20. After vortexing, 50 μl was pipetted into each well of each microplate. The microplates were incubated at room temperature on a laboratory bench top for 1 hour.

Each microplate was washed three times. Each wash used 200 μl of 1×TBS/0.1% Tween-20 per well.

Alkaline Phosphatase Conjugated Streptavidin was diluted 1/10,000 in 1% BSA/TBS/0.1% Tween-20. Vortex. 50 μl was pipetted into each well of microplate. The microplates were incubated at room temperature on bench top for 1 h.

All plates were washed for 6 times with 200 μl 1×PBS/0.1% Tween-20 per well.

After finishing washing the microplates (≤5 microplates per assay), 50 μl of CSPD-Sapphire luminescence substrate (brought room temperature prior to use) was added to each well and the wells were incubated for 15 minutes at room temperature in the dark. The timer was started after finishing of the adding of the substrate solution to the first plate of the group of microplates. This step was done with a group of 5 plates or less.

Plates were read in a Glow Runner luminometer.

Data Analysis (Apply to Both Aβ$_{42}$ and Aβ$_{total}$ Sandwich ELISA Assays):

Standard Curve Criteria
1. Determine linear range of standard curves ($R^2>0.96$). Assure that all samples are within the linear range of the curve.
2. Determine the lowest sensitivity of the standard curve; the value that is significantly different from the no peptide background by unpaired two-tailed T-test (Prism). Also confirm that this point is statistically significantly different from the adjacent point higher on the standard curve by an unpaired one-tailed T-test.
3. Calculate the % CV (% coefficient of variation) of each point on the standard curve in the linear range (all datapoints must be % CV<30%).

A. Calculations
1. Average the sample values and calculate the SD (standard deviation) and % CV (all datapoints must be <30%). If not, determine if one well is an outlier by using the Grubbs test (Graphpad website).
2. Convert sample values to pg/well using the linear fit of the standard curve.

Footnotes (Apply to Both Aβ$_{42}$ and Aβ$_{total}$ Sandwich ELISA Assays)

[1] Aβ peptides are stored in HFIP to prevent aggregation that frequently occurs with these peptides.

[2] This step is important to remove residual uncoated antibody that may contribute to high background.

[3] GloRunner luminometer which quantitates light from a 96-well microplate was used.

Example 8

Synthetic Procedures for the Synthesis of 49

Preparation of Bromoketone Advanced Intermediate

Synthesis of Bromoketone 111:

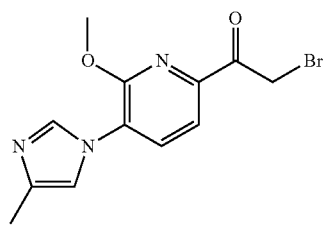

111

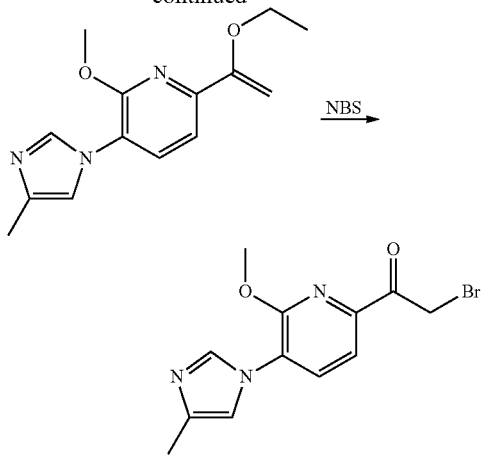

111

Reference: WO 2010/098488

Synthesis of N-(6-bromo-2-methoxypyridin-3-yl)formamide

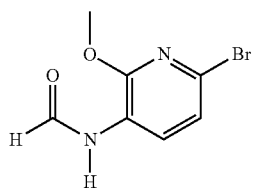

Acetic anhydride (203 mL) was added dropwise to formic acid (204 mL) under ice-cooling, and the mixture was stirred at the same temperature for 25 min. 6-bromo-2-methoxypyridine-3-amine power (CAS#89466-18-2, 146 g) was put into the reaction mixture over 10 minutes, and the reaction solution was stirred at the same temperature for 30 minutes. The water bath was removed. tert-Butyl methyl ether (300 mL) and n-heptane (500 mL) were sequentially added dropwise to the reaction solution, and then the reaction solution was stirred for 30 minutes.

The precipitated powder was collected by filtration. The resulting powder was crushed with a mortar, washed with tert-butyl methyl ether and then dried under reduced pressure to obtain 137.4 g of the title compound. Then the combined filtrate and washing solution were concentrated under reduced pressure. The residue was triturated with tert-butyl methyl ether and dried under reduced pressure to obtain 21.9 g of the title compound. The property values of the compound are as follows.

$^{1}$H-NMR (CDCl$_{3}$) δ (ppm): 4.03 (s, 3H), 7.08 (d, J=8.0 Hz, 1H), 7.61 (brs, 1 H), 8.47-8.51 (m, 2H).

Synthesis of N-(6-bromo-2-methoxypyridin-3-yl)-N-(2-oxopropyl)formamide

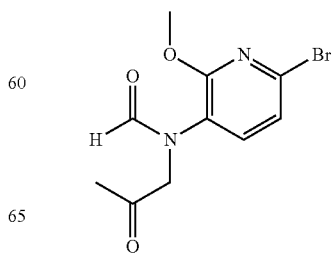

Synthetic Scheme 1

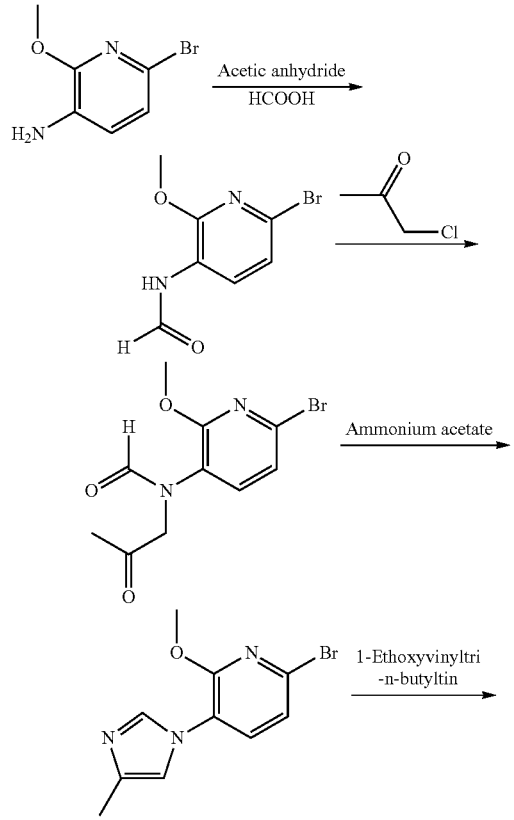

Chloroactone (82 mL) was added dropwise to a suspension of N-(6-bromo-2-methoxypyridin-3-yl)formamide (159.3 g), cesium carbonate (359 g) and potassium iodide (11.4 g) IN DMF (800 mL) over seven minutes. Then, the reaction solution was stirred at room temperature for one hour and 20 minutes. The reaction solution was concentrated under reduced pressure. Ethyl acetate and water were added to the resulting residue, and the organic layer was separated. The resulting organic layer was washed with brine, dried over anhydrous magnesium sulfate and then concentrated under reduced pressure to obtain 215.2 g of the title compound. The property values of the compound are as follows.

$^1$H-NMR (CDCl$_3$) δ (ppm): 2.17 (s, 3H), 4.00 (s, 3H), 4.47 (s, 2H), 7.13 (d, J=7.6 Hz, 1H), 7.48 (d, J=7.6 Hz, 1H), 8.22 (s, 1H).

Synthesis of 6-bromo-2-methoxy-3-(4-methyl-1H-imidazole-1-yl)pyridine

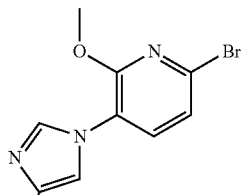

A suspension of ammonium acetate (267 g) and N-(6-bromo-2-methoxypyridin-3-yl)-N-(2-oxopropyl)formamide (199 g) in glacial acetic acid (400 mL) was stirred at 130° C. for one hour and 10 minutes. The reaction solution was brought back to room temperature. Ethyl acetate and ice water were added to the reaction solution, and the mixture was ice-cooled. Then, concentrated aqueous ammonia (500 mL) was added dropwise and then the organic layer was separated. The resulting organic layer was sequentially washed with water and brine and dried over anhydrous magnesium sulfate. Then, the organic layer was purified by short silica gel column chromatography. The eluted fraction was concentrated. The resulting reside was triturated with ethyl acetate and tert-butyl methyl ether and dried under reduced pressure to obtain 107.7 g of the title compound.

Then, the trituration mother liquor was concentrated. The resulting residue was purified silica column chromatography. The target fraction was concentrated. The resulting residue was triturated with tert-butyl methyl ether and dried under reduced pressure to obtain 12.9 g of the title compound.

The property values of the compound are as follows:
$^1$H-NMR (CDCl$_3$) δ (ppm): 2.29 (d, J=0.8 Hz, 3H), 4.03 (s, 3H), 6.92 (dd, J=1.2, 0.8 Hz, 1H), 7.16 (d, J=8.0 Hz, 1H), 7.40 (d, J=8.0 Hz, 1H), 7.73 (d, J=1.2 Hz, 1H).

ESI-MS; m/z 268 [M+H].

Synthesis of 6-(1-ethoxyvinyl)-2-methoxy-3-(4-methyl-1H-imidazol-1-yl)pyridine

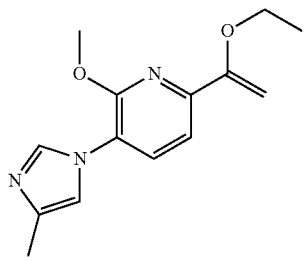 [SMILES: C=C(OCC)c1ccc(-n2cnc(C)c2)c(OC)n1]

1-Ethoxyvinyltri-n-butyltin (3.7 mL) was added to a suspension of 6-bromo-2-methoxy-3-(4-methyl-1H-imidazole-1-yl)pyridine (2.66 g) and bis(triphenylphosphine)palladium (II) chloride (350 mg) in dioxane (25 mL), and the mixture was stirred at 100° C. for five hours and 45 minutes. The reaction solution was left to cool to room temperature and then concentrated under reduced pressure. The resulting residue was purified by silica gel column chromatography. The target fraction was concentrated. The resulting powder was triturated with diethyl ether-n-hexane and dried under reduced pressure to obtain 1.57 g of the title compound. Then, the mother liquor was concentrated to obtain 858 mg of the title compound. The property values of the compound are as follows: $^1$H-NMR (CDCl$_3$) δ (ppm): 1.45 (t, J=7.2 Hz, 3H), 2.30 (s, 3H), 3.98 (q, J=7.2 Hz, 2H), 4.04 (s, 3H), 4.38 (d, J=1.6 Hz, 1H), 5.48 (d, J=1.6 Hz, 1H), 6.97 (s, 1H), 7.38 (d, j=8.0 Hz, 1H), 7.52 (d, J=8.0 Hz, 1H), 7.78 (s, 1H).

Synthesis of 2-bromo-1-[6-methoxy-5-(4-methyl-1H-imidazole-1-yl)pyridine-2-yl]ethanone dihydrochloride

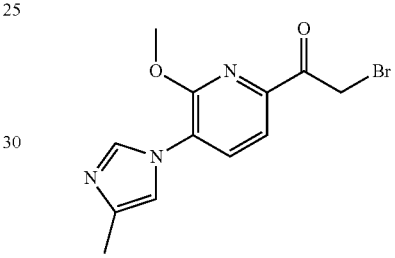

N-bromosuccinimide (543 mg) was added to a solution of 6-(1-ethoxyvinyl)-2-methoxy-3-(4-methyl-1H-imidazol-1-yl)pyridine (791 mg) in THF (15 mL)-water (2 mL) at room temperature, and the mixture was stirred at the same temperature for 15 minutes. A saturated sodium bicarbonate solution and ethyl acetate were added to the reaction solution, and the organic layer was separated. The resulting organic layer was washed with brine and dried over anhydrous magnesium sulfate. Anhydrous magnesium sulfate was removed from the organic layer by filtration. A 4N solution of HCl in ethyl acetate was added to the resulting filtrate. Thereafter, the filtrate was concentrated under reduced pressure to obtain 1.06 g of the title compound. The property values of the compound are as follows. ESI-MS; m/z 310 [M+H-2-HCl].

Preparation of Thiourea Advanced Intermediate

C. Synthesis of Thiourea 113

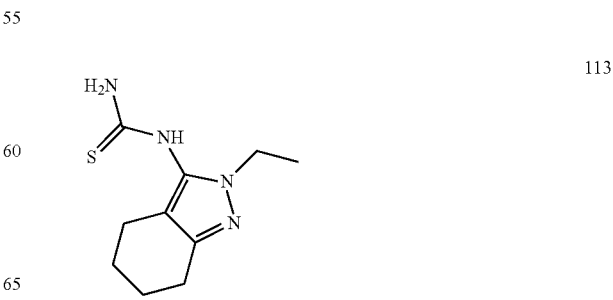

Synthetic Scheme 2

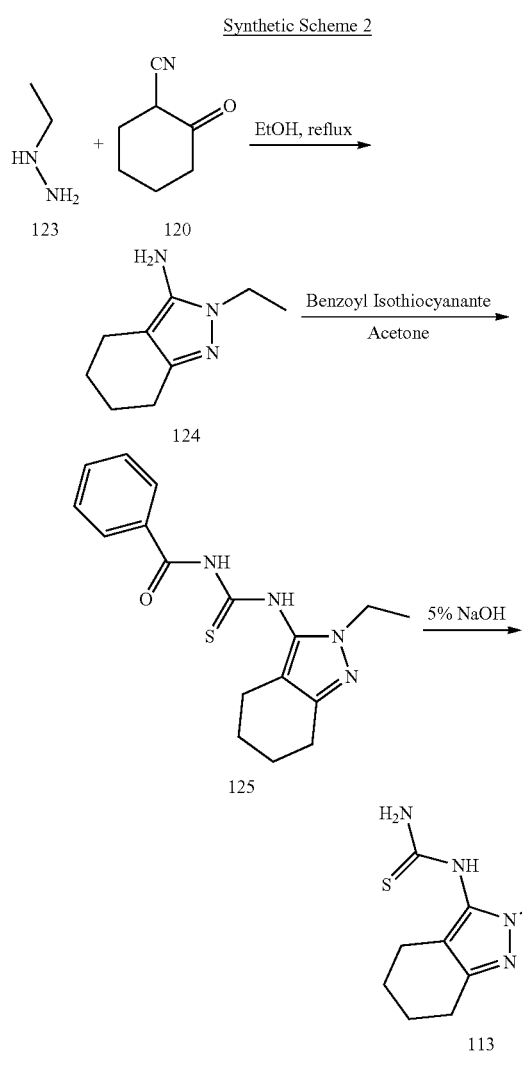

The coupling of ethylhydrazine 123 with acetonitrile 120 in ethanol under reflux gave 124. Coupling of 124 with benzoyl isothiocyanate yield the benzoyl thiourea 125 in excellent yield. Alkaline hydrolysis of 125 yielded thiourea 113.

Preparation of 2-methyl-4,5,6,7-tetrahydro-2H-indazol-3-amine 124

A solution of 2-oxocyclohexanecarbonitrile 120 (10 g, 81.2 mmol) and ethyl hydrazine 119 (3 equiv, 14.6 g) in 150 mL of absolute ethanol was refluxed for 20 hrs and was concentrated on rotavapor to dryness. The crude product was recrystallized from methanol to afford the desired product 124. (Reference for the preparation of compound 124: *J. Am. Chem. Soc.* 1959, 81, 2448-2452)

Preparation of N-(2-methyl-4,5,6,7-tetrahydro-2H-indazol-3-ylcarbamothioyl)benzamide 125

To a solution of compound 124 (5.44 g, 33.1 mmol) in 40 mL of acetone at 0° C. was added dropwise benzoyl isothiocynate (5.4 g, 33.1 mmol). The reaction mixture was gradually warmed up and stirred in an oil bath of 60° C. until TLC indicated there was no starting material remained. Concentration of the reaction mixture on rotavapor gave a yellow solid, which was further recrystallized in ethyl acetate to yield the desired product 325.

Preparation of 1-(2-methyl-4,5,6,7-tetrahydro-2H-indazol-3-yl)thiourea 113

A suspension of compound 125 (3.1 g, 9.5 mmol) in 30 mL of 5% NaOH aqueous solution was stirred in an oil bath of 90° C. for 8 hrs and cooled down to room temperature. Ice was added while stirring to the reaction mixture. The resulting suspension was filtered, and the cake was washed with cold water (10 mL×3) and further dried in vacuo to afford the desired product 113 as an off-white powder.

Synthesis of Compound 49

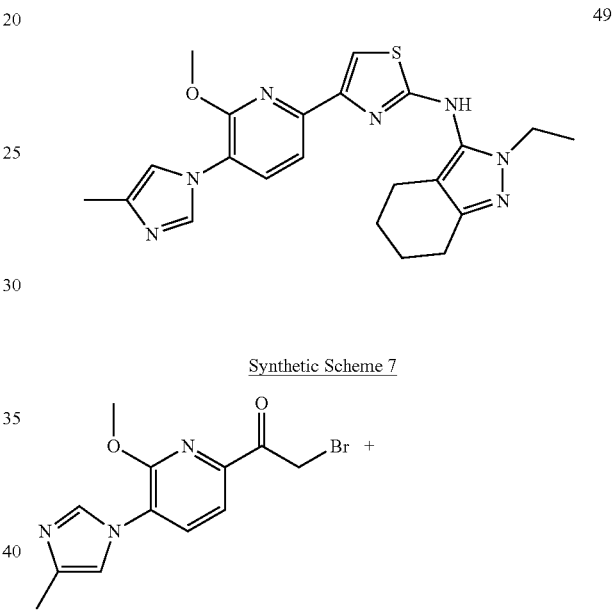

Synthetic Scheme 7

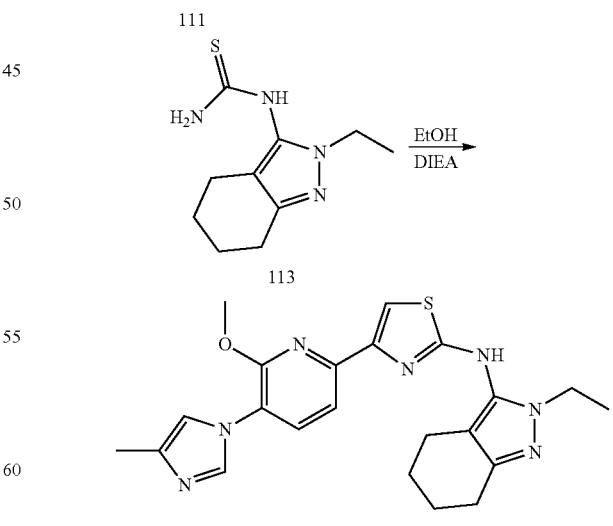

To a solution of compound 113 (538 mg, 2.4 mmol) in 8 mL of absolute ethanol was added compound 111 (744 mg, 2.4 mmol) followed by Hünig's base (4 equiv, 1.1 g) at room temperature. The reaction mixture was stirred in an oil bath of 55° C. until LCMS indicated there was a single peak product formed and no starting material remained. Removal of most of ethanol and DIEA gave the crude product that was purified by reverse-phased HPLC to yield the desired product 49, $^1$H-NMR (DMSO-d6) δ (ppm): 1.24 (t, J=7.2 Hz, 3H), 1.64-1.72 (m, 4H), 2.14 (s, 3H), 2.30-2.32 (m, 2H), 2.48-2.52 (m, 4H), 3.92 (q, J=7.2 Hz, 2H), 3.98 (s, 3H), 7.23 (brs, 1H), 7.47-7.51 (m, 2H), 7.84-7.90 (m, 2H), 9.73 (brs, 1H), $[M+H]^+=437$.

What is claimed is:

1. A compound having a structure corresponding to Formula (I):

(A)-(B)-(C)-(D)     (I)

or a pharmaceutically acceptable salt or prodrug thereof:
Wherein A is:

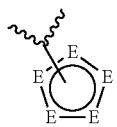

Wherein each E is independently N, NR, C, or CR$^1$, provided that two or three E's are N or NR;
N is nitrogen; C is carbon; R is hydrogen, substituted or unsubstituted alkyl, substituted or unsubstituted alkenyl, substituted or unsubstituted alkynyl, substituted or unsubstituted alkoxy, substituted or unsubstituted alkylamino, substituted or unsubstituted cycloalkyl, or substituted or unsubstituted aryl;
Each R$^1$ is independently hydrogen, substituted or unsubstituted alkyl, substituted or unsubstituted alkenyl, substituted or unsubstituted alkynyl, substituted or unsubstituted alkoxy, substituted or unsubstituted alkylamino, substituted or unsubstituted cycloalkyl, or substituted or unsubstituted aryl;
Wherein B is:

Wherein each G is independently CR$^2$;
Each R$^2$ is independently a hydrogen, halogen, substituted or unsubstituted alkyl, substituted or unsubstituted alkenyl, substituted or unsubstituted alkynyl, substituted or unsubstituted alkoxy, substituted or unsubstituted alkylamido, substituted or unsubstituted alkylamino, substituted or unsubstituted amino, substituted or unsubstituted alkylsulfide, substituted or unsubstituted alkyl sulfinyl group, or substituted or unsubstituted alkyl sulfonyl group;
Wherein B is:

a.

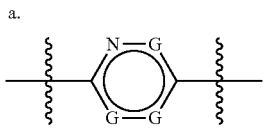

Wherein each G is independently CR$^{3a}$;
Each R$^{3a}$ is independently a hydrogen, halogen, substituted or unsubstituted alkyl, substituted or unsubstituted alkenyl, substituted or unsubstituted alkynyl, substituted or unsubstituted alkoxy, substituted or unsubstituted alkylamido, substituted or unsubstituted alkylamino, substituted or unsubstituted amino, substituted or unsubstituted alkylsulfide, substituted or unsubstituted alkyl sulfinyl group, or substituted or unsubstituted alkyl sulfonyl group;

b.

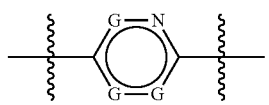

Wherein each G is independently CR$^{3b}$;
Each R$^{3b}$ is independently a hydrogen, halogen, substituted or unsubstituted alkyl, substituted or unsubstituted alkenyl, substituted or unsubstituted alkynyl, substituted or unsubstituted alkoxy, substituted or unsubstituted alkylamido, substituted or unsubstituted alkylamino, substituted or unsubstituted amino, substituted or unsubstituted alkylsulfide, substituted or unsubstituted alkyl sulfinyl group, or substituted or unsubstituted alkyl sulfonyl group; or c.

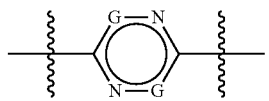

Wherein each G is independently CR$^{3c}$;
Each R$^{3c}$ is independently a hydrogen, halogen, substituted or unsubstituted alkyl, substituted or unsubstituted alkenyl, substituted or unsubstituted alkynyl, substituted or unsubstituted alkoxy, substituted or unsubstituted alkylamido, substituted or unsubstituted alkylamino, substituted or unsubstituted amino, substituted or unsubstituted alkylsulfide, substituted or unsubstituted alkyl sulfinyl group, or substituted or unsubstituted alkyl sulfonyl group; and
Wherein C is:

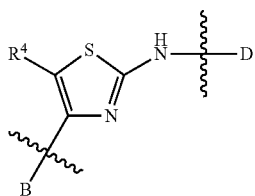

Wherein R$^4$ is hydrogen, halogen, substituted or unsubstituted alkyl, substituted or unsubstituted cycloalkyl, substituted or unsubstituted aryl, or substituted or unsubstituted alkoxy; and Wherein D is:

a.

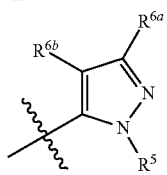

Wherein R⁵ is a hydrogen, substituted or unsubstituted alkyl, or substituted or unsubstituted cycloalkyl;
R$^{6a}$ and R$^{6b}$ are independently a hydrogen, substituted or unsubstituted alkyl, or substituted or unsubstituted cycloalkyl;

b.

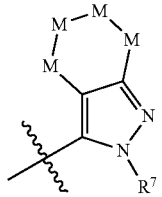

Wherein R⁷ is a hydrogen, substituted or unsubstituted alkyl, or substituted or unsubstituted cycloalkyl;
M is independently CHR⁸;
Each R⁸ is independently a hydrogen, halogen, substituted or unsubstituted alkyl, substituted or unsubstituted alkenyl, substituted or unsubstituted alkynyl, or substituted or unsubstituted alkoxy; or c.

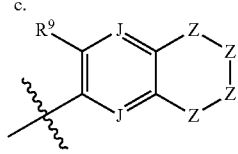

Where R⁹ is a hydrogen, halogen, or a substituted or unsubstituted alkyl;
J is independently CH or N;
Z is independently CHR¹⁰;
Each R¹⁰ is independently a hydrogen, halogen, substituted or unsubstituted alkyl, substituted or unsubstituted alkenyl, substituted or unsubstituted alkynyl, or substituted or unsubstituted alkoxy.

2. The compound of claim 1, wherein A of Formula (I) or a pharmaceutically acceptable salt thereof, is

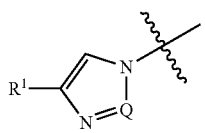

wherein Q is either CH or N.

3. The compound of claim 2, wherein R¹ is a substituted or unsubstituted C₁-C₅ alkyl.

4. The compound of claim 3, having a structure corresponding to Formula (II):

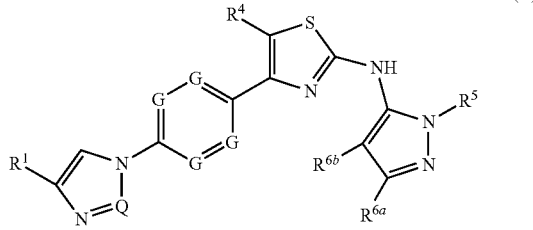

(II)

Wherein
R⁴ is hydrogen, halogen, substituted or unsubstituted alkyl, substituted or unsubstituted cycloalkyl, substituted or unsubstituted aryl, or substituted or unsubstituted alkoxy;
R⁵ is a hydrogen, substituted or unsubstituted alkyl, or substituted or unsubstituted cycloalkyl;
R$^{6a}$ and R$^{6b}$ are independently a hydrogen, substituted or unsubstituted alkyl, substituted or unsubstituted cycloalkyl;
G is independently CR$^{3c}$;
Each R$^{3c}$ is independently a hydrogen, halogen, substituted or unsubstituted alkyl, substituted or unsubstituted alkenyl, substituted or unsubstituted alkynyl, substituted or unsubstituted alkoxy, substituted or unsubstituted alkylamido, substituted or unsubstituted alkylamino, substituted or unsubstituted amino, substituted or unsubstituted alkylsulfide, substituted or unsubstituted alkyl sulfinyl group, or substituted or unsubstituted alkyl sulfonyl group; and
Q is either CH or N; or
having a structure corresponding to Formula (III):

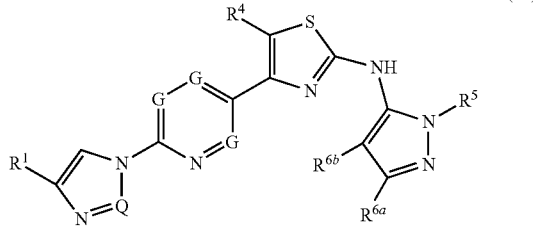

(III)

Wherein
R⁴ is hydrogen, halogen, substituted or unsubstituted alkyl, substituted or unsubstituted cycloalkyl, substituted or unsubstituted aryl, or substituted or unsubstituted alkoxy;
R⁵ is a hydrogen, a substituted or unsubstituted alkyl, or substituted or unsubstituted cycloalkyl;
R$^{6a}$ and R$^{6b}$ are independently a hydrogen, substituted or unsubstituted alkyl, substituted or unsubstituted cycloalkyl;
G is independently CR$^{3c}$;
Each R$^{3c}$ is independently a hydrogen, halogen, substituted or unsubstituted alkyl, substituted or unsubstituted alkenyl, substituted or unsubstituted alkynyl, substituted or unsubstituted alkoxy, substituted or unsubstituted alkylamido, substituted or unsubstituted alkylamino, substituted or unsubstituted amino, substituted or unsubstituted alkylsulfide, substituted or unsubstituted alkyl sulfinyl group, or substituted or unsubstituted alkyl sulfonyl group; and Q is either CH or N; or having a structure corresponding to Formula (IV):

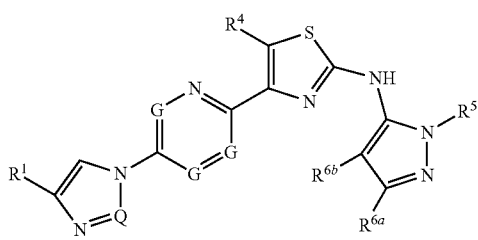

Wherein $R^4$ is hydrogen, halogen, substituted or unsubstituted alkyl, substituted or unsubstituted cycloalkyl, substituted or unsubstituted aryl, or substituted or unsubstituted alkoxy;

$R^5$ is a hydrogen, a substituted or unsubstituted alkyl, or substituted or unsubstituted cycloalkyl;

$R^{6a}$ and $R^{6b}$ are independently a hydrogen, substituted or unsubstituted alkyl, substituted or unsubstituted cycloalkyl;

G is independently $CR^{3c}$;

Each $R^{3c}$ is independently a hydrogen, halogen, substituted or unsubstituted alkyl, substituted or unsubstituted alkenyl, substituted or unsubstituted alkynyl, substituted or unsubstituted alkoxy, substituted or unsubstituted alkylamido, substituted or unsubstituted alkylamino, substituted or unsubstituted amino, substituted or unsubstituted alkylsulfide, substituted or unsubstituted alkyl sulfinyl group, or substituted or unsubstituted alkyl sulfonyl group; and Q is either CH or N; or having a structure corresponding to Formula (V):

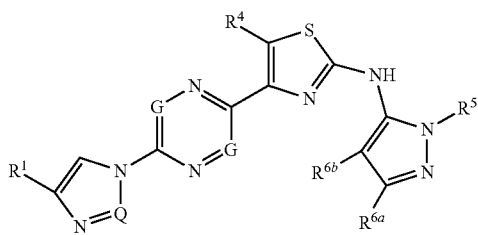

Wherein $R^4$ is hydrogen, halogen, substituted or unsubstituted alkyl, substituted or unsubstituted cycloalkyl, substituted or unsubstituted aryl, or substituted or unsubstituted alkoxy;

$R^5$ is a hydrogen, substituted or unsubstituted alkyl, or substituted or unsubstituted cycloalkyl;

$R^{6a}$ and $R^{6b}$ are independently a hydrogen, substituted or unsubstituted alkyl, substituted or unsubstituted cycloalkyl;

G is independently $CR^{3c}$;

Each $R^{3c}$ is independently a hydrogen, halogen, substituted or unsubstituted alkyl, substituted or unsubstituted alkenyl, substituted or unsubstituted alkynyl, substituted or unsubstituted alkoxy, substituted or unsubstituted alkylamido, substituted or unsubstituted alkylamino, substituted or unsubstituted amino, substituted or unsubstituted alkylsulfide, substituted or unsubstituted alkyl sulfinyl group, or substituted or unsubstituted alkyl sulfonyl group; and Q is either CH or N.

5. The compound of claim 1 wherein D is selected from a group consisting of:

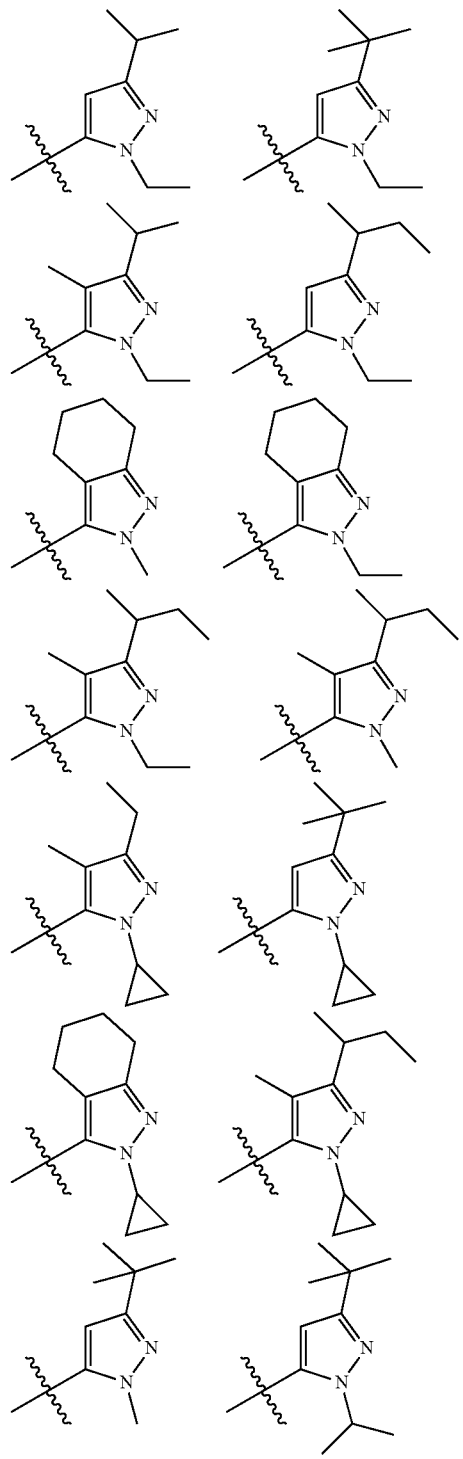

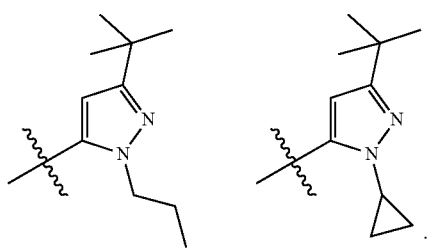 [SMILES: *c1cc(C(C)(C)C)nn1CCC ; *c1cc(C(C)(C)C)nn1C1CC1]

6. The compound of claim 4, having a structure corresponding to Formula (VI):

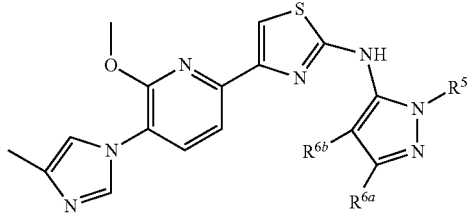
(VI)

Wherein R⁵ is a hydrogen, substituted or unsubstituted alkyl, or substituted or unsubstituted cycloalkyl; and R⁶ᵃ and R⁶ᵇ are independently a hydrogen, substituted or unsubstituted alkyl, substituted or unsubstituted cycloalkyl.

7. A compound having a structure corresponding to Formula (VII):

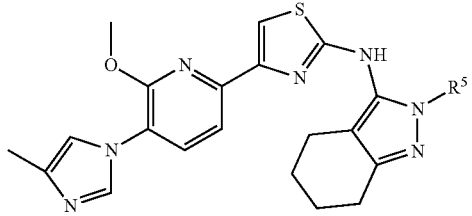
(VII)

Wherein R⁵ is a hydrogen, substituted or unsubstituted alkyl, or substituted or unsubstituted cycloalkyl.

8. The compound of claim 7, wherein said compound is selected from the group consisting of:

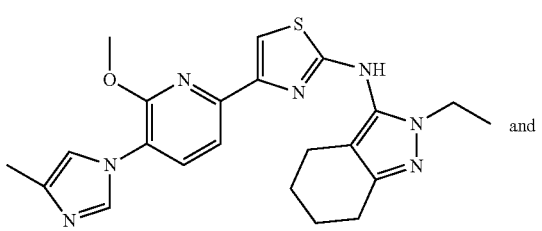
and

9. The compound of claim 6, wherein said compound is selected from the group consisting of:

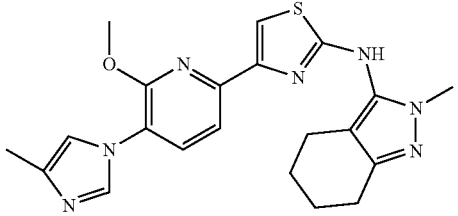

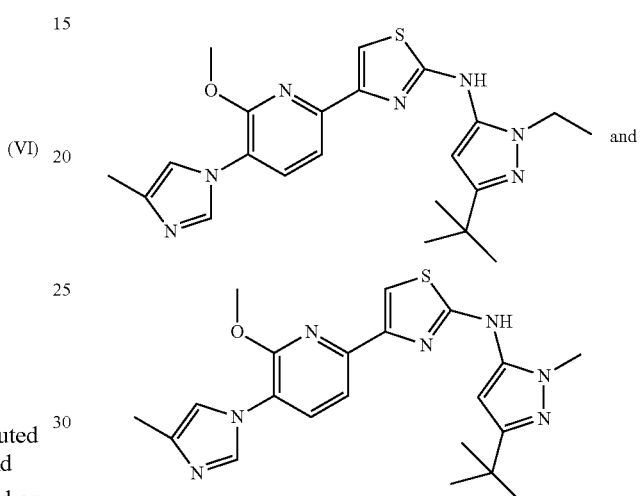
and

10. The compound of claim 4, having a structure corresponding to Formula (VIII):

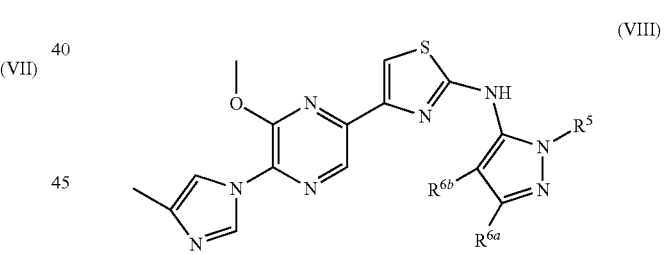
(VIII)

Wherein R⁵ is a hydrogen, substituted or unsubstituted alkyl, or substituted or unsubstituted cycloalkyl; and R⁶ᵃ and R⁶ᵇ are independently a hydrogen, substituted or unsubstituted alkyl, or substituted or unsubstituted cycloalkyl.

11. A compound having a structure corresponding to Formula (IX):

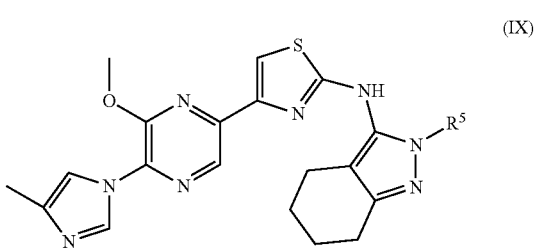
(IX)

Wherein $R^5$ is a hydrogen, substituted or unsubstituted alkyl, or substituted or unsubstituted cycloalkyl.
12. The compound of claim 11, wherein said compound is selected from the group consisting of:
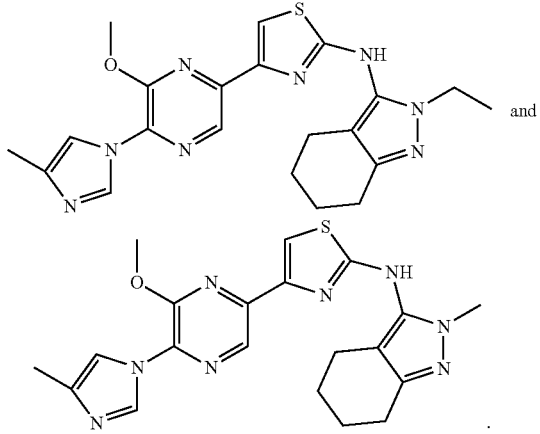
and
13. The compound of claim 10, wherein said compound is selected from the group consisting of:
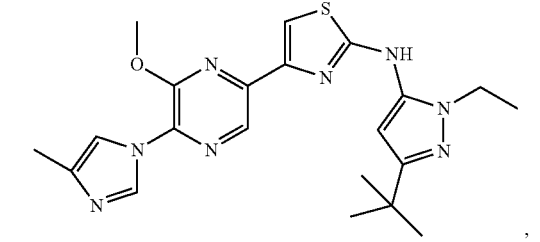
,
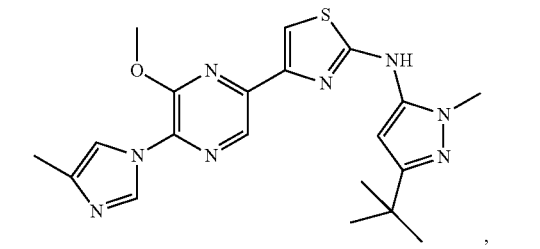
,
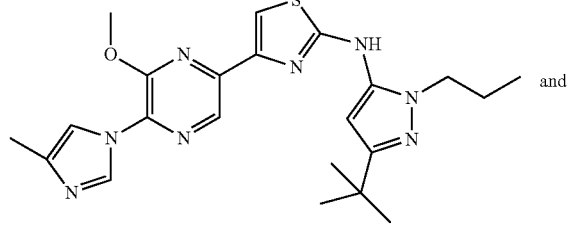
and
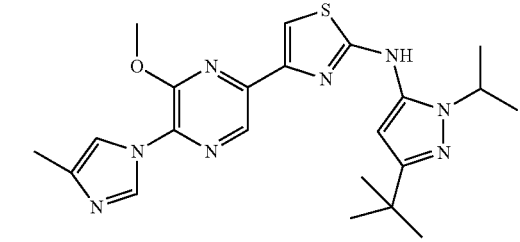
14. A compound selected from the group consisting of:
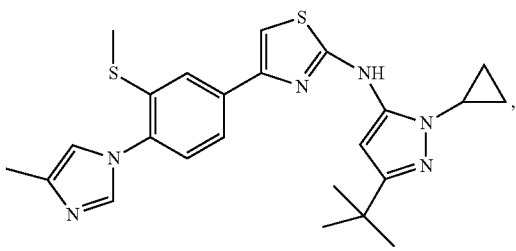
,
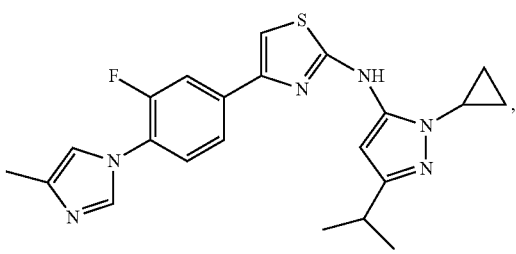
,
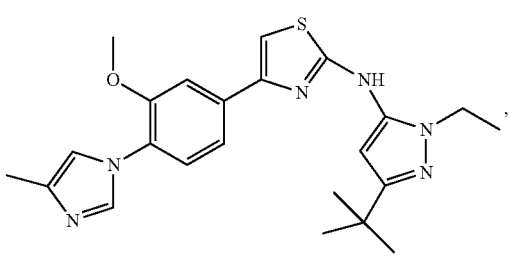
,
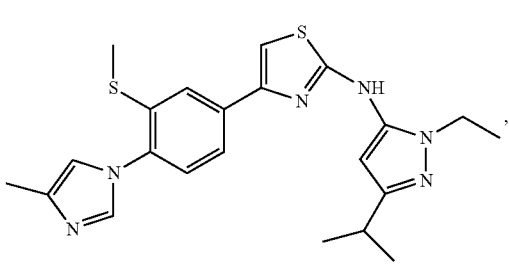
,
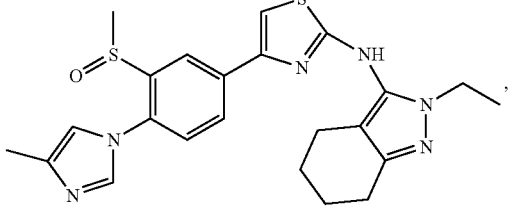
,
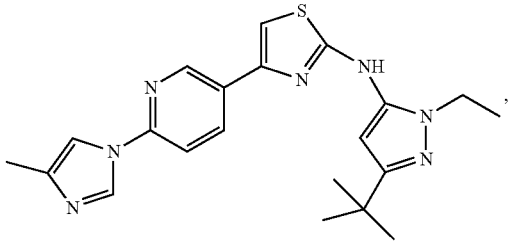
, -continued

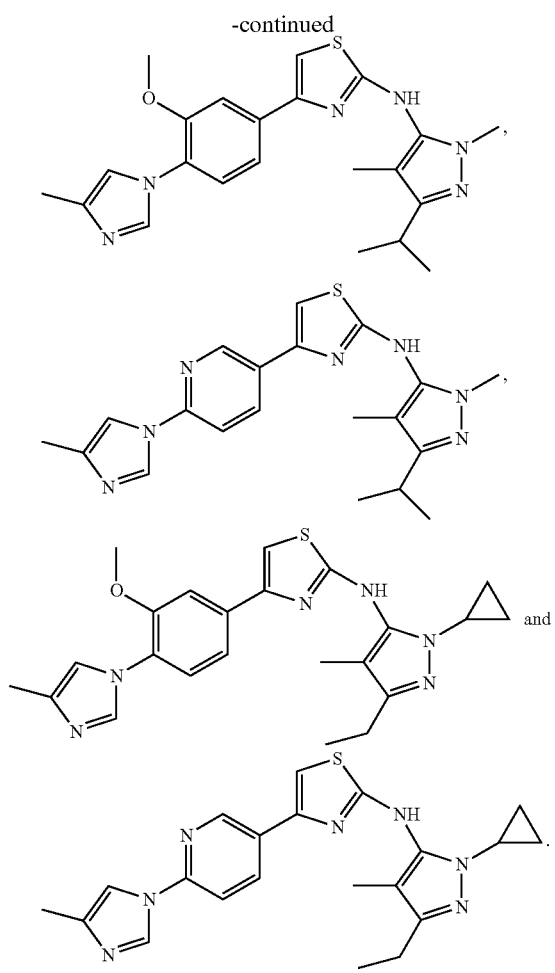

15. The compound of claim 1, wherein the unsubstituted alkyl group is methyl, ethyl, propyl, isopropyl, butyl, sec-butyl, or tert-butyl group.

16. The compound of claim 1, wherein the prodrug has structure (X) or (XI):

(X)

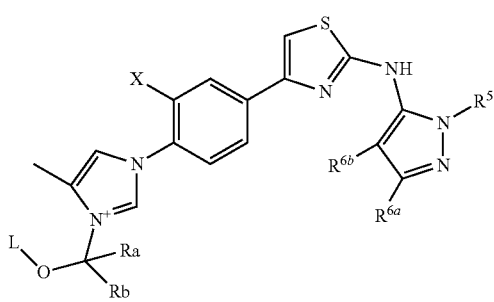

-continued (XI)

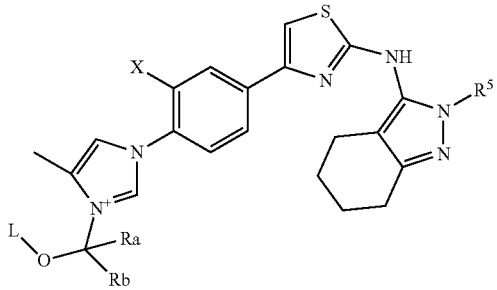

wherein:

X is a hydrogen, halogen, substituted or unsubstituted alkoxy, substituted or unsubstituted alkylsulfide, substituted or unsubstituted alkyl sulfinyl group, or substituted or unsubstituted alkyl sulfonyl group;

$R^5$ is a hydrogen, substituted or unsubstituted alkyl, or substituted or unsubstituted cycloalkyl;

$R^{6a}$ and $R^{6b}$ are independently a hydrogen, substituted or unsubstituted alkyl, or substituted or unsubstituted cycloalkyl;

Ra and Rb are a $C_{1-6}$ alkyl group; and

L is a phosphono group.

17. A method of modulating levels of a highly fibrillogenic amyloid-beta (Aβ) peptide comprising contacting a protease which proteolyzes an amyloid precursor protein (APP) carboxyl-terminal fragment (CTF) or fragment thereof with an effective amount of a compound of claim 1 so as to modulate the levels of fibrillogenic amyloid-beta (Aβ) peptides.

18. A method of inhibiting production of $A\beta_{42}$ or $A\beta_{40}$ comprising contacting a protease which proteolyzes an amyloid precursor protein (APP) carboxyl-terminal fragment (CTF) or fragment thereof with an effective amount of a compound of claim 1 so as inhibit production of $A\beta_{42}$ or $A\beta_{40}$.

19. A method of promoting production of $A\beta_{38}$ or $A\beta_{37}$ comprising contacting a protease which proteolyzes an amyloid precursor protein (APP) carboxyl-terminal fragment (CTF) or fragment thereof with an effective amount of a compound of claim 1 so as promote production of $A\beta_{38}$ or $A\beta_{37}$.

20. A method for treating Alzheimer's Disease in a subject, the method comprising administering to the subject a therapeutically effective amount of a compound of claim 1.

* * * * *